United States Patent
Mizuguchi et al.

(10) Patent No.: US 9,624,476 B2
(45) Date of Patent: Apr. 18, 2017

(54) CONDITIONALLY REPLICATING ADENOVIRUS

(71) Applicant: NATIONAL INSTITUTE OF BIOMEDICAL INNOVATION, Ibaraki-shi, Osaka (JP)

(72) Inventors: Hiroyuki Mizuguchi, Ibaraki (JP); Fuminori Sakurai, Ibaraki (JP)

(73) Assignee: NATIONAL INSTITUTE OF BIOMEDICAL INNOVATION, Ibaraki-shi, Osaka (JP)

( * ) Notice: Subject to any disclaimer, the term of this patent is extended or adjusted under 35 U.S.C. 154(b) by 0 days.

(21) Appl. No.: 15/183,661

(22) Filed: Jun. 15, 2016

(65) Prior Publication Data

US 2016/0333323 A1 Nov. 17, 2016

Related U.S. Application Data

(63) Continuation-in-part of application No. 14/240,216, filed as application No. PCT/JP2012/053814 on Feb. 17, 2012, now abandoned.

(30) Foreign Application Priority Data

Aug. 23, 2011 (JP) ................. 2011-181414

(51) Int. Cl.
| | |
|---|---|
| A61K 39/235 | (2006.01) |
| C12N 15/861 | (2006.01) |
| C12N 7/00 | (2006.01) |
| C12N 9/12 | (2006.01) |
| C12N 15/113 | (2010.01) |
| G01N 33/574 | (2006.01) |
| C12Q 1/68 | (2006.01) |
| C07K 14/005 | (2006.01) |

(52) U.S. Cl.
CPC .............. *C12N 7/00* (2013.01); *C07K 14/005* (2013.01); *C12N 9/1276* (2013.01); *C12N 15/113* (2013.01); *C12Q 1/6897* (2013.01); *C12Y 207/07049* (2013.01); *G01N 33/57492* (2013.01); *C12N 2310/141* (2013.01); *C12N 2710/10021* (2013.01); *C12N 2840/203* (2013.01); *G01N 2333/075* (2013.01); *G01N 2333/705* (2013.01)

(58) Field of Classification Search
None
See application file for complete search history.

(56) References Cited

U.S. PATENT DOCUMENTS

| | | |
|---|---|---|
| 7,951,585 B2 | 5/2011 | Ke |
| 2006/0062764 A1 | 3/2006 | Police et al. |
| 2006/0067890 A1 | 3/2006 | Fujiwara et al. |
| 2010/0047208 A1 | 2/2010 | Ke |
| 2010/0233125 A1* | 9/2010 | Tagawa ................ C12N 15/86 424/93.2 |

FOREIGN PATENT DOCUMENTS

| | | |
|---|---|---|
| JP | 2009-171861 A | 8/2009 |
| WO | WO 01/23004 A1 | 4/2001 |
| WO | WO 2005/121343 A1 | 12/2005 |
| WO | WO 2006/026331 A2 | 3/2006 |
| WO | WO 2006/036004 A1 | 4/2006 |
| WO | WO 2008/106646 A2 | 9/2008 |

OTHER PUBLICATIONS

Allard et al., "Tumor Cells Circulate in the Peripheral Blood of All Major Carcinomas but not in Healthy Subjects or Patients With Nonmalignant Diseases", Clinical Cancer Research, vol. 10, Oct. 15, 2004, pp. 6897-6904.
Chen et al., "MicroRNAs as regulators of mammalian hematopoiesis" Seminars in Immunology, vol. 17 (2005) pp. 155-165.
Chen et al., "MicroRNAs Modulate Hematopoietic Lineage Differentiation", Science, vol. 303, Jan. 2, 2004, pp. 83-86.
Cristofanilli et al., "Circulating Tumor Cells, Disease Progression, and Survival in Metastatic Breast Cancer", The New England Journal of Medicine, vol. 351, No. 8, Aug. 19, 2004, pp. 781-791.
Fujiwara et al., "Enhanced antitumor efficacy of telomerase-selective oncolytic adenoviral agent OBP-401 with docetaxel: Preclinical evaluation of chemovirotherapy", Int. J. Cancer; vol. 119 (2006) pp. 432-440.
Hui et al., "Comprehensive MicroRNA Profiling for Head and Neck Squamous Cell Carcinomas", Clin Cancer Res; vol. 16, No. 4 (2010) pp. 1129-1139.
International Search Report (Form PCT/Isa/210), dated Apr. 24, 2012, for International Application No. PCT/JP2012/053814, including English translation thereof.
Kojima et al., "A simple biological imaging system for detecting viable human circulating tumor cells", The Journal of Clinical Investigation, vol. 119, No. 10, Oct. 2009, pp. 3172-3181.
Lu et al., "Isolation of circulating epithelial and tumor progenitor cells with an invasive phenotype from breast cancer patients", Int J Cancer, vol. 126, No. 3, Feb. 1, 2010, pp. 669-683 (25 pages).

(Continued)

*Primary Examiner* — Richard Schnizer
(74) *Attorney, Agent, or Firm* — Birch, Stewart, Kolasch & Birch, LLP

(57) ABSTRACT

The object of the present invention is to provide a novel conditionally replicating adenovirus and a reagent comprising the same for cancer cell detection or for cancer diagnosis.
The present invention provides a polynucleotide, which comprises human telomerase reverse transcriptase (hTERT) promoter, E1A gene, IRES sequence and E1B gene in this order and which comprises a target sequence of a first miRNA. The present invention also provides a recombinant adenovirus, which comprises a replication cassette comprising the above polynucleotide, wherein the replication cassette is integrated into the E1 region of the adenovirus genome.

7 Claims, 8 Drawing Sheets

(56) References Cited

OTHER PUBLICATIONS

Marttila et al., "CD46 Is a Cellular Receptor for All Species B Adenoviruses except Types 3 and 7", Journal of Virology, vol. 79, No. 22, 2005, pp. 14429-14436.
Mathonnet et al., "MicroRNA Inhibition of Translation Initiation in Vitro by Targeting the Cap-Binding Complex eIF4F", Science, vol. 317, Sep. 21, 2007, pp. 1764-1767.
Mizuguchi et al., "Adenovirus vectors containing chimeric type 5 and type 35 fiber proteins exhibit altered and expanded tropism and increase the size limit of foreign genes", Gene, vol. 285, 2002, pp. 69-77.
Okegawa et al., "The Mechanism of the Growth-inhibitory Effect of Coxsackie and Adenovirus Receptor (CAR) on Human Bladder Cancer: A Functional Analysis of Car Protein Structure", Cancer Research, vol. 61, Sep. 1, 2001, pp. 6592-6600.
Pillai et al., "Inhibition of Translational Initiation by Let-7 MicroRNA in Human Cells", Science, vol. 309, Sep. 2, 2005, pp. 1573-1576.
Sakurai et al., "Development of Recombinant Adenovirus Carrying MicroRNA-regulated Gene Expression System", Journal of the Pharmaceutical Society of Japan (Yakugaku Zasshi), vol. 130, No. 11, 2010, pp. 1497-1504, including a partial English translation thereof.
Sakurai et al., "Genetic modification to improve safety of recombinant virus", Drug Delivery System, vol. 24, No. 6, 2009, pp. 572-581, including a partial English translation thereof.
Sakurai et al., "MicroRNA-regulated transgene expression systems for gene therapy and virotherapy", Frontiers in Bioscience, vol. 16, Jun. 1, 2011, pp. 2389-2401.
Schmitz et al., "Melanoma cultures show different susceptibility towards E1A-, E1B-19 kDa- and fiber-modified replication-competent adenoviruses", Gene Therapy, vol. 13 (2006) pp. 893-905.
Sieuwerts et al., "Anti-Epithelial Cell Adhesion Molecule Antibodies and the Detection of Circulating Normal-Like Breast Tumor Cells", J Natl Cancer Inst, vol. 101, Issue 1, Jan. 7, 2009, pp. 61-66.
Sugio et al., "Enhanced Safety Profiles of the Telomerase-Specific Replication-Competent Adenovirus by Incorporation of Normal Cell-Specific microRNA-Targeted Sequences", Clinical Cancer Research, vol. 17, No. 9, May 1, 2011 (Published online first Feb. 23, 2011), pp. 2807-2818.
Suzuki et al., "miR-122a-Regulated Expression of a Suicide Gene Prevents Hepatotoxicity Without Altering Antitumor Effects in Suicide Gene Therapy", Molecular Therapy, vol. 16, No. 10, Oct. 2008 (Published online Jul. 29, 2008), pp. 1719-1726.
Wang et al., "In Vitro and in Vivo Properties of Adenovirus Vectors with Increased Affinity to CD46", Journal of Virology, vol. 82, No. 21 (2008) pp. 10567-10579.
Yu et al., "Increased infectivity of adenovirus type 5 bearing type 11 or type 35 fibers to human esophageal and oral carcinoma cells", Oncology Reports, vol. 14, 2005, pp. 831-835.
Zhao et al., "MicroRNA expression profile and identification of miR-29 as a prognostic marker and pathogenetic factor by targeting CDK6 in mantle cell lymphona", Blood, vol. 115, No. 13 (2010) pp. 2630-2639.
Brown et al (Nature Medicine 12(5): 585-591, 2006).
Chen et al (Cancer Letters vol. 307, Issue 1, Aug. 1, 2011, pp. 93-103).
Wu et al (FEBS Letters 585 (2011) 1322-1330).
Wu et al (Mol. Therap. 17(12): 2058-2066, 2009).

\* cited by examiner

SEQUENCE LISTING

```
<160> NUMBER OF SEQ ID NOS: 55

<210> SEQ ID NO 1
<211> LENGTH: 455
<212> TYPE: DNA
<213> ORGANISM: Homo sapiens

<400> SEQUENCE: 1
tggcccctcc ctcgggttac cccacagcct aggccgattc gacctctctc cgctggggcc    60
ctcgctggcg tccctgcacc ctgggagcgc gagcggcgcg cgggcgggga agcgcggccc   120 agaccccgg gtccgcccgg agcagctgcg ctgtcggggc caggccgggc tcccagtgga   180
ttcgcgggca cagacgccca ggaccgcgct ccccacgtgg cggagggact ggggacccgg   240
gcacccgtcc tgcccttca ccttccagct ccgcctcctc cgcgcggacc ccgccccgtc    300
ccgacccctc ccgggtcccc ggcccagccc cctccgggcc ctcccagccc ctcccccttcc   360 tttccgcggc ccgccctct cctcgcggcg cgagtttcag gcagcgctgc gtcctgctgc    420
gcacgtggga agccctggcc ccggccaccc ccgcg                               455

<210> SEQ ID NO 2
<211> LENGTH: 899
<212> TYPE: DNA
<213> ORGANISM: Adenovirus

<400> SEQUENCE: 2
acaccgggac tgaaaatgag acatattatc tgccacggag gtgttattac cgaagaaatg    60
gccgccagtc ttttggacca gctgatcgaa gaggtactgg ctgataatct tccacctcct   120
agccattttg aaccacctac ccttcacgaa ctgtatgatt tagacgtgac ggcccccgaa   180
gatcccaacg aggaggcggt ttcgcagatt tttcccgact ctgtaatgtt ggcggtgcag   240
gaagggattg acttactcac ttttccgccg gcgcccggtt ctccggagcc gcctcaccttt   300 tcccggcagc ccgagcagcc ggagcagaga gccttgggtc cggtttctat gccaaaccttt   360 gtaccggagg tgatcgatct tacctgccac gaggctggct ttccacccag tgacgacgag   420
gatgaagagg tgaggagtt tgtgttagat tatgtggagc accccgggca cggttgcagg   480
tcttgtcatt atcaccggag gaatacgggg gacccagata ttatgtgttc gctttgctat   540
atgaggacct gtggcatgtt tgtctacagt cctgtgtctg aacctgagcc tgagcccgag   600
ccagaaccgg agcctgcaag acctacccgc cgtcctaaaa tggcgcctgc tatcctgaga   660
cgcccgacat cacctgtgtc tagagaatgc aatagtagta cggatagctg tgactccggt   720
ccttctaaca cacctcctga gatacacccg gtggtcccgc tgtgccccat taaaccagtt   780
gccgtgagag ttggtgggcg tcgccaggct gtggaatgta tcgaggactt gcttaacgag    840
cctgggcaac ctttggactt gagctgtaaa cgccccaggc cataaggtgt aaacctgtg    899
```

<210> SEQ ID NO 3
<211> LENGTH: 1823
<212> TYPE: DNA
<213> ORGANISM: Adenovirus

<400> SEQUENCE: 3

| | | | | | |
|---|---|---|---|---|---|
| ctgacctcat | ggaggcttgg | gagtgtttgg | aagattttc | tgctgtgcgt | aacttgctgg | 60 |
| aacagagctc | taacagtacc | tcttggtttt | ggaggtttct | gtgggctca | tcccaggcaa | 120 |
| agttagtctg | cagaattaag | gaggattaca | agtgggaatt | tgaagagctt | ttgaaatcct | 180 |
| gtggtgagct | gtttgattct | ttgaatctgg | gtcaccaggc | gcttttccaa | gagaaggtca | 240 |
| tcaagacttt | ggattttcc | acccggggc | gcgctgcggc | tgctgttgct | tttttgagtt | 300 |
| ttataaagga | taaatggagc | gaagaaaccc | atctgagcgg | ggggtacctg | ctggattttc | 360 |
| tggccatgca | tctgtggaga | gcggttgtga | gacacaagaa | tcgcctgcta | ctgttgtctt | 420 |
| ccgtccgccc | ggcgataata | ccgacggagg | agcagcagca | gcagcaggag | gaagccaggc | 480 |
| ggcggcggca | ggagcagagc | ccatggaacc | cgagagccgg | cctggaccct | cgggaatgaa | 540 |
| tgttgtacag | gtggctgaac | tgtatccaga | actgagacgc | attttgacaa | ttacagagga | 600 |
| tgggcagggg | ctaaagggg | taagaggga | gcggggggct | tgtgaggcta | cagaggaggc | 660 |
| taggaatcta | gcttttagct | taatgaccag | acaccgtcct | gagtgtatta | cttttcaaca | 720 |
| gatcaaggat | aattgcgcta | atgagcttga | tctgctggcg | cagaagtatt | ccatagagca | 780 |
| gctgaccact | tactggctgc | agccagggga | tgattttgag | gaggctatta | gggtatatgc | 840 |
| aaaggtggca | cttaggccag | attgcaagta | caagatcagc | aaacttgtaa | atatcaggaa | 900 |
| tgttgctac | atttctggga | acggggccga | ggtggagata | gatacggagg | ataggtggc | 960 |
| ctttagatgt | agcatgataa | atatgtggcc | gggggtgctt | ggcatggacg | gggtggttat | 1020 |
| tatgaatgta | aggtttactg | gccccaattt | tagcggtacg | gttttcctgg | ccaataccaa | 1080 |
| ccttatccta | cacggtgtaa | gcttctatgg | gtttaacaat | acctgtgtgg | aagcctggac | 1140 |
| cgatgtaagg | gttcggggct | gtgccttta | ctgctgctgg | aaggggtgg | tgtgtcgccc | 1200 |
| caaaagcagg | gcttcaatta | agaaatgcct | ctttgaaagg | tgtaccttgg | gtatcctgtc | 1260 |
| tgagggtaac | tccagggtgc | gccacaatgt | ggcctccgac | tgtggttgct | tcatgctagt | 1320 |
| gaaaagcgtg | gctgtgatta | agcataacat | ggtatgtggc | aactgcgagg | acagggcctc | 1380 |
| tcagatgctg | acctgctcgg | acggcaactg | tcacctgctg | aagaccattc | acgtagccag | 1440 |
| ccactctcgc | aaggcctggc | cagtgtttga | gcataacata | ctgacccgct | gttccttgca | 1500 |
| tttgggtaac | aggaggggg | tgttcctacc | ttaccaatgc | aatttgagtc | acactaagat | 1560 |
| attgcttgag | cccgagagca | tgtccaaggt | gaacctgaac | ggggtgtttg | acatgaccat | 1620 |
| gaagatctgg | aaggtgctga | ggtacgatga | gacccgcacc | aggtgcagac | cctgcgagtg | 1680 |
| tggcggtaaa | catattagga | accagcctgt | gatgctggat | gtgaccgagg | agctgaggcc | 1740 |
| cgatcacttg | gtgctggcct | gcacccgcgc | tgagtttggc | tctagcgatg | aagatacaga | 1800 |
| ttgaggtact | gaaatgtgtg | ggc | | | | 1823 |

<210> SEQ ID NO 4
<211> LENGTH: 605
<212> TYPE: DNA
<213> ORGANISM: Artificial
<220> FEATURE:
<223> OTHER INFORMATION: synthetic DNA

<400> SEQUENCE: 4

```
tgcatctagg gcggccaatt ccgcccctct ccctcccccc ccctaacgt tactggccga      60
agccgcttgg aataaggccg gtgtgcgttt gtctatatgt gattttccac catattgccg    120
tcttttggca atgtgagggc ccggaaacct ggccctgtct tcttgacgag cattcctagg    180
ggtctttccc ctctcgccaa aggaatgcaa ggtctgttga atgtcgtgaa ggaagcagtt    240
cctctggaag cttcttgaag acaaacaacg tctgtagcga ccctttgcag gcagcggaac    300
cccccacctg gcgacaggtg cctctgcggc caaaagccac gtgtataaga tacacctgca    360
aaggcggcac aaccccagtg ccacgttgtg agttggatag ttgtggaaag agtcaaatgg    420
ctctcctcaa gcgtattcaa caaggggctg aaggatgccc agaaggtacc ccattgtatg    480
ggatctgatc tggggcctcg gtgcacatgc tttacatgtg tttagtcgag gttaaaaaaa    540
cgtctaggcc ccccgaacca cggggacgtg gttttccttt gaaaaacacg atgataagct    600
tgcca                                                                 605
```

```
<210> SEQ ID NO 5
<211> LENGTH: 23
<212> TYPE: RNA
<213> ORGANISM: Artificial
<220> FEATURE:
<223> OTHER INFORMATION: synthetic RNA
```

<400> SEQUENCE: 5

```
uguaguguuu ccuacuuuau gga                                              23
```

```
<210> SEQ ID NO 6
<211> LENGTH: 21
<212> TYPE: RNA
<213> ORGANISM: Artificial
<220> FEATURE:
<223> OTHER INFORMATION: synthetic RNA
```

<400> SEQUENCE: 6

```
cauaaaguag aaagcacuac u                                                21
```

```
<210> SEQ ID NO 7
<211> LENGTH: 22
<212> TYPE: RNA
<213> ORGANISM: Artificial
<220> FEATURE:
<223> OTHER INFORMATION: synthetic RNA
```

<400> SEQUENCE: 7

```
uagcagcaca uaaugguuug ug                                               22
```

```
<210> SEQ ID NO 8
<211> LENGTH: 22
<212> TYPE: RNA
<213> ORGANISM: Artificial
<220> FEATURE:
<223> OTHER INFORMATION: synthetic RNA
```

<400> SEQUENCE: 8

```
caggccauau ugugcugccu ca                                               22
```

```
<210> SEQ ID NO 9
<211> LENGTH: 22
<212> TYPE: RNA
<213> ORGANISM: Artificial
<220> FEATURE:
<223> OTHER INFORMATION: synthetic RNA
```

```
<400> SEQUENCE: 9
uagcagcacg uaaauauugg cg                                          22

<210> SEQ ID NO 10
<211> LENGTH: 22
<212> TYPE: RNA
<213> ORGANISM: Artificial
<220> FEATURE:
<223> OTHER INFORMATION: synthetic RNA

<400> SEQUENCE: 10
ccaguauuaa cugugcugcu ga                                          22

<210> SEQ ID NO 11
<211> LENGTH: 22
<212> TYPE: RNA
<213> ORGANISM: Artificial
<220> FEATURE:
<223> OTHER INFORMATION: synthetic RNA

<400> SEQUENCE: 11
uagcuuauca gacugauguu ga                                          22

<210> SEQ ID NO 12
<211> LENGTH: 21
<212> TYPE: RNA
<213> ORGANISM: Artificial
<220> FEATURE:
<223> OTHER INFORMATION: synthetic RNA

<400> SEQUENCE: 12
caacaccagu cgaugggcug u                                           21

<210> SEQ ID NO 13
<211> LENGTH: 22
<212> TYPE: RNA
<213> ORGANISM: Artificial
<220> FEATURE:
<223> OTHER INFORMATION: synthetic RNA

<400> SEQUENCE: 13
ucguaccgug aguaauaaug cg                                          22

<210> SEQ ID NO 14
<211> LENGTH: 21
<212> TYPE: RNA
<213> ORGANISM: Artificial
<220> FEATURE:
<223> OTHER INFORMATION: synthetic RNA

<400> SEQUENCE: 14
cauuauuacu uuugguacgc g                                           21

<210> SEQ ID NO 15
<211> LENGTH: 23
<212> TYPE: RNA
<213> ORGANISM: Artificial
<220> FEATURE:
<223> OTHER INFORMATION: synthetic RNA

<400> SEQUENCE: 15
aacauucaac gcugucggug agu                                         23

<210> SEQ ID NO 16
```

```
<211> LENGTH: 22
<212> TYPE: RNA
<213> ORGANISM: Artificial
<220> FEATURE:
<223> OTHER INFORMATION: synthetic RNA

<400> SEQUENCE: 16
ugucaguuug ucaaauaccc ca                                              22

<210> SEQ ID NO 17
<211> LENGTH: 22
<212> TYPE: RNA
<213> ORGANISM: Artificial
<220> FEATURE:
<223> OTHER INFORMATION: synthetic RNA

<400> SEQUENCE: 17
cguguauuug acaagcugag uu                                              22

<210> SEQ ID NO 18
<211> LENGTH: 22
<212> TYPE: RNA
<213> ORGANISM: Artificial
<220> FEATURE:
<223> OTHER INFORMATION: synthetic RNA

<400> SEQUENCE: 18
gaggguuggg uggaggcucu cc                                              22

<210> SEQ ID NO 19
<211> LENGTH: 21
<212> TYPE: RNA
<213> ORGANISM: Artificial
<220> FEATURE:
<223> OTHER INFORMATION: synthetic RNA

<400> SEQUENCE: 19
agggcccccc cucaauccug u                                               21

<210> SEQ ID NO 20
<211> LENGTH: 24
<212> TYPE: RNA
<213> ORGANISM: Artificial
<220> FEATURE:
<223> OTHER INFORMATION: synthetic RNA

<400> SEQUENCE: 20
ucccugagac ccuuuaaccu guga                                            24

<210> SEQ ID NO 21
<211> LENGTH: 21
<212> TYPE: RNA
<213> ORGANISM: Artificial
<220> FEATURE:
<223> OTHER INFORMATION: synthetic RNA

<400> SEQUENCE: 21
ugagaugaag cacguagcu c                                                21

<210> SEQ ID NO 22
<211> LENGTH: 22
<212> TYPE: RNA
<213> ORGANISM: Artificial
<220> FEATURE:
<223> OTHER INFORMATION: synthetic RNA

<400> SEQUENCE: 22
```

```
ggugcagugc ugcaucucug gu                                              22
```

<210> SEQ ID NO 23
<211> LENGTH: 23
<212> TYPE: RNA
<213> ORGANISM: Artificial
<220> FEATURE:
<223> OTHER INFORMATION: synthetic RNA

<400> SEQUENCE: 23

```
guccaguuuu cccaggaauc ccu                                             23
```

<210> SEQ ID NO 24
<211> LENGTH: 22
<212> TYPE: RNA
<213> ORGANISM: Artificial
<220> FEATURE:
<223> OTHER INFORMATION: synthetic RNA

<400> SEQUENCE: 24

```
ggauuccugg aaauacuguu cu                                              22
```

<210> SEQ ID NO 25
<211> LENGTH: 23
<212> TYPE: RNA
<213> ORGANISM: Artificial
<220> FEATURE:
<223> OTHER INFORMATION: synthetic RNA

<400> SEQUENCE: 25

```
cccaguguuc agacuaccug uuc                                             23
```

<210> SEQ ID NO 26
<211> LENGTH: 22
<212> TYPE: RNA
<213> ORGANISM: Artificial
<220> FEATURE:
<223> OTHER INFORMATION: synthetic RNA

<400> SEQUENCE: 26

```
ugagguagua gguuguauag uu                                              22
```

<210> SEQ ID NO 27
<211> LENGTH: 69
<212> TYPE: DNA
<213> ORGANISM: Artificial
<220> FEATURE:
<223> OTHER INFORMATION: synthetic DNA

<400> SEQUENCE: 27

```
gcggcctcca taaagtagga aacactacac agctccataa agtaggaaac actacattat     60
aagcggtac                                                             69
```

<210> SEQ ID NO 28
<211> LENGTH: 113
<212> TYPE: DNA
<213> ORGANISM: Artificial
<220> FEATURE:
<223> OTHER INFORMATION: synthetic DNA

<400> SEQUENCE: 28

```
ggcctccata aagtaggaaa cactacacag ctccataaag taggaaacac tacattaatt     60
ccataaagta ggaaacacta caccactcca taaagtagga aacactacag tac           113
```

<210> SEQ ID NO 29
<211> LENGTH: 1307
<212> TYPE: DNA
<213> ORGANISM: Homo sapiens

<400> SEQUENCE: 29

| | | | | | |
|---|---|---|---|---|---|
| accgtccagg | gagcaggtag | ctgctgggct | ccggggacac | tttgcgttcg | ggctgggagc | 60 |
| gtgctttcca | cgacggtgac | acgcttccct | ggattggcag | ccagactgcc | ttccgggtca | 120 |
| ctgccatgga | ggagccgcag | tcagatccta | gcgtcgagcc | ccctctgagt | caggaaacat | 180 |
| tttcagacct | atggaaacta | cttcctgaaa | acaacgttct | gtcccccttg | ccgtcccaag | 240 |
| caatggatga | tttgatgctg | tccccggacg | atattgaaca | atggttcact | gaagacccag | 300 |
| gtccagatga | agctcccaga | atgccagagg | ctgctcccg | cgtggcccct | gcaccagcga | 360 |
| ctcctacacc | ggcggcccct | gcaccagccc | cctcctggcc | cctgtcatct | tctgtccctt | 420 |
| cccagaaaac | ctaccagggc | agctacggtt | tccgtctggg | cttcttgcat | tctgggacag | 480 |
| ccaagtctgt | gacttgcacg | tactcccctg | ccctcaacaa | gatgttttgc | caactggcca | 540 |
| agacctgccc | tgtgcagctg | tgggttgatt | ccacaccccc | gcccggcacc | cgcgtccgcg | 600 |
| ccatggccat | ctacaagcag | tcacagcaca | tgacggaggt | tgtgaggcgc | tgcccccacc | 660 |
| atgagcgctg | ctcagatagc | gatggtctgg | cccctcctca | gcatcttatc | cgagtggaag | 720 |
| gaaatttgcg | tgtggagtat | ttggatgaca | gaaacacttt | tcgacatagt | gtggtggtgc | 780 |
| cctatgagcc | gcctgaggtt | ggctctgact | gtaccaccat | ccactacaac | tacatgtgta | 840 |
| acagttcctg | catgggcggc | atgaaccgga | ggcccatcct | caccatcatc | acactggaag | 900 |
| actccagtgg | taatctactg | ggacggaaca | gctttgaggt | gcgtgtttgt | gcctgtcctg | 960 |
| ggagagaccg | gcgcacagag | gaagagaatc | tccgcaagaa | aggggagcct | caccacgagc | 1020 |
| tgcccccagg | gagcactaag | cgagcactgc | ccaacaacac | cagctcctct | ccccagccaa | 1080 |
| agaagaaacc | actggatgga | gaatatttca | cccttcagat | ccgtgggcgt | gagcgcttcg | 1140 |
| agatgttccg | agagctgaat | gaggccttgg | aactcaagga | tgcccaggct | gggaaggagc | 1200 |
| caggggggag | cagggctcac | tccagccacc | tgaagtccaa | aaagggtcag | tctacctccc | 1260 |
| gccataaaaa | actcatgttc | aagacagaag | ggcctgactc | agactga | | 1307 |

<210> SEQ ID NO 30
<211> LENGTH: 837
<212> TYPE: DNA
<213> ORGANISM: Homo sapiens

<400> SEQUENCE: 30

| | | | | | |
|---|---|---|---|---|---|
| gaggactccg | cgacggtccg | caccctgcgg | ccagagcggc | tttgagctcg | gctgcttccg | 60 |
| cgctaggcgc | ttttccccag | aagcaatcca | ggcgcgcccg | ctggttcttg | agcgccagga | 120 |
| aaagcccgga | gctaacgacc | ggccgctcgg | cactgcacgg | ggcccaagc | cgcagaagaa | 180 |
| ggacgacggg | agggtaatga | agctgagccc | aggtctccta | ggaaggagag | agtgcgccgg | 240 |
| agcagcgtgg | gaaagaaggg | aagagtgtcg | ttaagtttac | ggccaacggt | ggattatccg | 300 |
| ggccgctgcg | cgtctggggg | ctgcggaatg | cgcgaggaga | acaagggcat | gcccagtggg | 360 |
| ggcggcagcg | atgagggtct | ggccacgccg | gcgcggggac | tagtggagaa | ggtgcgacac | 420 |
| tcctgggaag | ccggcgcgga | tcccaacgga | gtcaaccgtt | tcgggaggcg | cgcgatccag | 480 |
| gtcatgatga | tgggcagcgc | ccgcgtggcg | gagctgctgc | tgctccacgg | cgcggagccc | 540 |
| aactgcgcag | accctgccac | tctcacccga | ccggtgcatg | atgctgcccg | ggagggcttc | 600 |

```
ctggacacgc tggtggtgct gcaccgggcc ggggcgcggc tggacgtgcg cgatgcctgg      660
ggtcgtctgc ccgtggactt ggccgaggag cggggccacc gcgacgttgc agggtacctg      720
cgcacagcca cgggggactg acgccaggtt ccccagccgc ccacaacgac tttattttct      780
tacccaattt cccaccccca cccacctaat tcgatgaagg ctgccaacgg ggagcgg         837

<210> SEQ ID NO 31
<211> LENGTH: 987
<212> TYPE: DNA
<213> ORGANISM: Homo sapiens

<400> SEQUENCE: 31
cggagagggg gagaacagac aacgggcggc ggggagcagc atggagccgg cggcggggag       60
cagcatggag ccttcggctg actggctggc acggccgcg gcccgggggtc gggtagagga      120 ggtgcgggcg ctgctggagg cggggcgct gcccaacgca ccgaatagtt acggtcggag       180
gccgatccag gtcatgatga tgggcagcgc ccgagtggcg gagctgctgc tgctccacgg      240
cgcggagccc aactgcgccg accccgccac tctcacccga cccgtgcacg acgctgcccg      300
ggagggcttc ctggacacgc tggtggtgct gcaccgggcc ggggcgcggc tggacgtgcg      360
cgatgcctgg ggccgtctgc ccgtggacct ggctgaggag ctgggccatc gcgatgtcgc      420
acggtacctg cgcgcggctg cgggggggcac cagaggcagt aaccatgccc gcatagatgc      480
cgcggaaggt ccctcagaca tccccgattg aaagaaccag agaggctctg agaaacctcg      540
ggaaacttag atcatcagtc accgaaggtc ctacagggcc acaactgccc ccgccacaac      600 ccacccccgct ttcgtagttt tcatttagaa aatagagctt ttaaaaatgt cctgccttt      660 aacgtagata taagccttcc cccactaccg taaatgtcca tttatatcat tttttatata      720
ttcttataaa aatgtaaaaa agaaaaacac cgcttctgcc ttttcactgt gttggagttt      780
tctggagtga gcactcacgc cctaagcgca cattcatgtg ggcatttctt gcgagcctcg      840
cagcctccgg aagctgtcga cttcatgaca agcattttgt gaactaggga agctcagggg      900
ggttactggc ttctcttgag tcacactgct agcaaatggc agaaccaaag ctcaaataaa      960
aataaaataa ttttcattca ttcactc                                          987

<210> SEQ ID NO 32
<211> LENGTH: 8972
<212> TYPE: DNA
<213> ORGANISM: Homo sapiens

<400> SEQUENCE: 32
gtccaagggt agccaaggat ggctgcagct tcatatgatc agttgttaaa gcaagttgag       60
gcactgaaga tggagaactc aaatcttcga caagagctag aagataattc caatcatctt      120
acaaaactgg aaactgaggc atctaatatg aaggaagtac ttaaacaact acaaggaagt      180
attgaagatg aagctatggc ttcttctgga cagattgatt tattagagcg tcttaaagag      240
cttaacttag atagcagtaa tttccctgga gtaaaactgc ggtcaaaaat gtccctccgt      300
tcttatggaa gccgggaagg atctgtatca agccgttctg agagtgcag tcctgttcct      360 atgggttcat ttccaagaag aggggtttgta atggaagca gagaaagtac tggatattta      420
gaagaacttg agaaagagag gtcattgctt cttgctgatc ttgacaaaga agaaaaggaa      480
aaagactggt attacgctca acttcagaat ctcactaaaa gaatagatag tcttccttta      540
actgaaaatt tttccttaca aacagatatg accagaaggc aattggaata tgaagcaagg      600
```

| | |
|---|---|
| caaatcagag ttgcgatgga agaacaacta ggtacctgcc aggatatgga aaaacgagca | 660 |
| cagcgaagaa tagccagaat tcagcaaatc gaaaaggaca tacttcgtat acgacagctt | 720 |
| ttacagtccc aagcaacaga agcagagagg tcatctcaga acaagcatga aaccggctca | 780 |
| catgatgctg agcggcagaa tgaaggtcaa ggagtgggag aaatcaacat ggcaacttct | 840 |
| ggtaatggtc agggttcaac tacacgaatg gaccatgaaa cagccagtgt tttgagttct | 900 |
| agtagcacac actctgcacc tcgaaggctg acaagtcatc tgggaaccaa ggtgaaatg | 960 |
| gtgtattcat tgttgtcaat gcttggtact catgataagg atgatatgtc gcgaactttg | 1020 |
| ctagctatgt ctagctccca agacagctgt atatccatgc gacagtctgg atgtcttcct | 1080 |
| ctcctcatcc agcttttaca tggcaatgac aaagactctg tattgttggg aaattcccgg | 1140 |
| ggcagtaaag aggctcgggc cagggccagt gcagcactcc acaacatcat tcactcacag | 1200 |
| cctgatgaca agagaggcag gcgtgaaatc cgagtccttc atcttttgga acagatacgc | 1260 |
| gcttactgtg aaacctgttg ggagtggcag gaagctcatg aaccaggcat ggaccaggac | 1320 |
| aaaaatccaa tgccagctcc tgttgaacat cagatctgtc ctgctgtgtg tgttctaatg | 1380 |
| aaactttcat ttgatgaaga gcatagacat gcaatgaatg aactagggggg actacaggcc | 1440 |
| attgcagaat tattgcaagt ggactgtgaa atgtacgggc ttactaatga ccactacagt | 1500 |
| attacactaa gacgatatgc tggaatggct ttgacaaact tgacttttgg agatgtagcc | 1560 |
| aacaaggcta cgctatgctc tatgaaaggc tgcatgagag cacttgtggc ccaactaaaa | 1620 |
| tctgaaagtg aagacttaca gcaggttatt gcaagtgttt tgaggaattt gtcttggcga | 1680 |
| gcagatgtaa atagtaaaaa gacgttgcga gaagttggaa gtgtgaaagc attgatggaa | 1740 |
| tgtgctttag aagttaaaaa ggaatcaacc ctcaaaagcg tattgagtgc cttatggaat | 1800 |
| ttgtcagcac attgcactga gaataaagct gatatatgtg ctgtagatgg tgcacttgca | 1860 |
| tttttggttg gcactcttac ttaccggagc cagacaaaca ctttagccat tattgaaagt | 1920 |
| ggaggtggga tattacggaa tgtgtccagc ttgatagcta caaatgagga ccacaggcaa | 1980 |
| atcctaagag agaacaactg tctacaaact ttattacaac acttaaaatc tcatagtttg | 2040 |
| acaatagtca gtaatgcatg tggaactttg tggaatctct cagcaagaaa tcctaaagac | 2100 |
| caggaagcat tatgggacat gggggcagtt agcatgctca agaacctcat tcattcaaag | 2160 |
| cacaaaatga ttgctatggg aagtgctgca gctttaagga atctcatggc aaataggcct | 2220 |
| gcgaagtaca aggatgccaa tattatgtct cctggctcaa gcttgccatc tcttcatgtt | 2280 |
| aggaaacaaa aagcccctaga agcagaatta gatgctcagc acttatcaga aactttttgac | 2340 |
| aatatagaca atttaagtcc caaggcatct catcgtagta agcagagaca caagcaaagt | 2400 |
| ctctatggtg attatgtttt tgacaccaat cgacatgatg ataataggtc agacaatttt | 2460 |
| aatactggca acatgactgt cctttcacca tatttgaata ctacagtgtt acccagctcc | 2520 |
| tcttcatcaa gaggaagctt agatagttct cgttctgaaa aagatagaag tttggagaga | 2580 |
| gaacgcggaa ttggtctagg caactaccat ccagcaacag aaaatccagg aacttcttca | 2640 |
| aagcgaggtt tgcagatctc caccactgca gcccagattg ccaaagtcat ggaagaagtg | 2700 |
| tcagccattc atacctctca ggaagacaga agttctgggt ctaccactga attacattgt | 2760 |
| gtgacagatg agagaaatgc acttagaaga agctctgctg cccatacaca ttcaaacact | 2820 |
| tacaatttca ctaagtcgga aaattcaaat aggacatgtt ctatgcctta tgccaaatta | 2880 |
| gaatacaaga gatcttcaaa tgatagttta aatagtgtca gtagtagtga tggttatggt | 2940 |
| aaaagaggtc aaatgaaacc ctcgattgaa tcctattctg aagatgatga agtaagttt | 3000 |

```
tgcagttatg gtcaataccc agccgaccta gcccataaaa tacatagtgc aaatcatatg    3060
gatgataatg atggagaact agatacacca ataaattata gtcttaaata ttcagatgag    3120
cagttgaact ctggaaggca aagtccttca cagaatgaaa gatgggcaag acccaaacac    3180
ataatagaag atgaaataaa acaaagtgag caaagacaat caaggaatca aagtacaact    3240
tatcctgttt atactgagag cactgatgat aaacacctca agttccaacc acattttgga    3300
cagcaggaat gtgtttctcc atacaggtca cggggagcca atggttcaga acaaatcga    3360 gtgggttcta atcatggaat taatcaaaat gtaagccagt cttttgtgtca agaagatgac    3420 tatgaagatg ataagcctac caattatagt gaacgttact ctgaagaaga acagcatgaa    3480
gaagaagaga gaccaacaaa ttatagcata aaatataatg aagagaaacg tcatgtggat    3540
cagcctattg attatagttt aaaatatgcc acagatattc cttcatcaca gaaacagtca    3600
ttttcattct caaagagttc atctggacaa agcagtaaaa ccgaacatat gtcttcaagc    3660
agtgagaata cgtccacacc ttcatctaat gccaagaggc agaatcagct ccatccaagt    3720
tctgcacaga gtagaagtgg tcagcctcaa aaggctgcca cttgcaaagt ttcttctatt    3780
aaccaagaaa caatcagac ttattgtgta gaagatactc caatatgttt ttcaagatgt    3840
agttcattat catctttgtc atcagctgaa gatgaaatag gatgtaatca gacgacacag    3900
gaagcagatt ctgctaatac cctgcaaata gcagaaataa aagaaagat tggaactagg    3960 tcagctgaag atcctgtgag cgaagttcca gcagtgtcac agcaccctag aaccaaatcc    4020
agcagactgc agggttctag tttatcttca gaatcagcca ggcacaaagc tgttgaattt    4080
tcttcaggag cgaaatctcc ctccaaaagt ggtgctcaga cacccaaaag tccacctgaa    4140
cactatgttc aggagacccc actcatgttt agcagatgta cttctgtcag ttcacttgat    4200
agttttgaga gtcgttcgat tgccagctcc gttcagagtg aaccatgcag tggaatggta    4260
agtggcatta taagccccag tgatcttcca gatagccctg acaaaccat gccaccaagc    4320 agaagtaaaa cacctccacc acctcctcaa acagctcaaa ccaagcgaga agtacctaaa    4380
aataaagcac ctactgctga aaagagagag agtggaccta agcaagctgc agtaaatgct    4440
gcagttcaga gggtccaggt tcttccagat gctgatactt tattacattt tgccacggaa    4500
agtactccag atggatttc ttgttcatcc agcctgagtg ctctgagcct cgatgagcca    4560
tttatacaga aagatgtgga attaagaata atgcctccag ttcaggaaaa tgacaatggg    4620
aatgaaacag aatcagagca gcctaaagaa tcaaatgaaa accaagagaa agaggcagaa    4680
aaaactattg attctgaaaa ggacctatta gatgattcag atgatgatga tattgaaata    4740
ctagaagaat gtattatttc tgccatgcca acaaagtcat cacgtaaagc aaaaaagcca    4800
gcccagactg cttcaaaatt acctccacct gtggcaagga accaagtca gctgcctgtg    4860 tacaaacttc taccatcaca aaacaggttg caaccccaaa agcatgttag ttttacaccg    4920
ggggatgata tgccacgggt gtattgtgtt aagggacac ctataaactt ttccacagct    4980
acatctctaa gtgatctaac aatcgaatcc cctccaaatg agttagctgc tggagaagga    5040
gttagaggag gagcacagtc aggtgaattt gaaaaacgag ataccattcc tacagaaggc    5100
agaagtacag atgaggctca aggaggaaaa acctcatctg taaccatacc tgaattggat    5160
gacaataaag cagaggaagg tgatattctt gcagaatgca ttaattctgc tatgcccaaa    5220
gggaaaagtc acaagccttt ccgtgtgaaa aagataatgg accaggtcca gcaagcatct    5280
gcgtcgtctt ctgcacccaa caaaaatcag ttagatggta agaaaaagaa accaacttca    5340
```

```
ccagtaaaac ctataccaca aaatactgaa tataggacac gtgtaagaaa aaatgcagac    5400
tcaaaaaata atttaaatgc tgagagagtt ttctcagaca acaaagattc aaagaaacag    5460
aatttgaaaa ataattccaa ggacttcaat gataagctcc caaataatga agatagagtc    5520
agaggaagtt ttgcttttga ttcacctcat cattacacgc ctattgaagg aactccttac    5580
tgtttttcac gaaatgattc tttgagttct ctagattttg atgatgatga tgttgacctt    5640
tccagggaaa aggctgaatt aagaaaggca aagaaaaata aggaatcaga ggctaaagtt    5700
accagccaca cagaactaac ctccaaccaa caatcagcta ataagacaca agctattgca    5760
aagcagccaa taaatcgagg tcagcctaaa cccatacttc agaaacaatc cacttttccc    5820
cagtcatcca aagacatacc agacagaggg gcagcaactg atgaaaagtt acagaatttt    5880
gctattgaaa atactccagt ttgctttttct cataattcct ctctgagttc tctcagtgac    5940
attgaccaag aaaacaacaa taaagaaaat gaacctatca aagagactga gcccctgac     6000 tcacagggag aaccaagtaa acctcaagca tcaggctatg ctcctaaatc atttcatgtt    6060
gaagataccc cagtttgttt ctcaagaaac agttctctca gttctcttag tattgactct    6120
gaagatgacc tgttgcagga atgtataagc tccgcaatgc caaaaaagaa aaagccttca    6180
agactcaagg gtgataatga aaaacatagt cccagaaata tgggtggcat attaggtgaa    6240
gatctgacac ttgatttgaa agatatacag agaccagatt cagaacatgg tctatcccct    6300
gattcagaaa attttgattg gaaagctatt caggaaggtg caaattccat agtaagtagt    6360
ttacatcaag ctgctgctgc tgcatgttta tctagacaag cttcgtctga ttcagattcc    6420
atcctttccc tgaaatcagg aatctctctg ggatcaccat ttcatcttac acctgatcaa    6480
gaagaaaaac cctttacaag taataaaggc ccacgaattc taaaaccagg ggagaaaagt    6540
acattggaaa ctaaaaagat agaatctgaa agtaaaggaa tcaaggagg aaaaaaagtt    6600 tataaaagtt tgattactgg aaaagttcga tctaattcag aaatttcagg ccaaatgaaa    6660 cagcccttc aagcaaacat gccttcaatc tctcgaggca ggacaatgat tcatattcca    6720
ggagttcgaa atagctcctc aagtacaagt cctgtttcta aaaaaggccc accccttaag    6780
actccagcct ccaaaagccc tagtgaaggt caaacagcca ccacttctcc tagaggagcc    6840
aagccatctg tgaaatcaga attaagccct gttgccaggc agacatccca aataggtggg    6900
tcaagtaaag caccttctag atcaggatct agagattcga ccccttcaag acctgcccag    6960
caaccattaa gtagacctat acagtctcct ggccgaaact caatttcccc tggtagaaat    7020
ggaataagtc ctccctaacaa attatctcaa cttccaagga catcatcccc tagtactgct    7080
tcaactaagt cctcaggttc tggaaaaatg tcatatacat ctccaggtag acagatgagc    7140
caacagaacc ttaccaaaca aacaggttta tccaagaatg ccagtagtat tccaagaagt    7200
gagtctgcct ccaaaggact aaatcagatg aataatggta atggagccaa taaaaaggta    7260
gaactttcta gaatgtcttc aactaaatca agtggaagtg aatctgatag atcagaaaga    7320
cctgtattag tacgccagtc aactttcatc aaagaagctc caagcccaac cttaagaaga    7380
aaattggagg aatctgcttc atttgaatct cttttctcca t catctagacc agcttctccc    7440
actaggtccc aggcacaaac tccagttttta agtccttccc ttcctgatat gtctctatcc    7500
acacattcgt ctgttcaggc tggtggatgg cgaaaactcc cacctaatct cagtcccact    7560
atagagtata atgatggaag accagcaaag cgccatgata ttgcacggtc tcattctgaa    7620
agtccttcta gacttccaat caataggtca ggaacctgga acgtgagca cagcaaacat     7680 tcatcatccc ttcctcgagt aagcacttgg agaagaactg gaagttcatc ttcaattctt    7740
```

```
tctgcttcat cagaatccag tgaaaaagca aaaagtgagg atgaaaaaca tgtgaactct   7800
atttcaggaa ccaaacaaag taagaaaac caagtatccg caaaaggaac atggagaaaa   7860
ataaaagaaa atgaattttc tcccacaaat agtacttctc agaccgtttc ctcaggtgct   7920
acaaatggtg ctgaatcaaa gactctaatt tatcaaatgg cacctgctgt ttctaaaaca   7980
gaggatgttt gggtgagaat tgaggactgt cccattaaca atcctagatc tggaagatct   8040
cccacaggta atactccccc ggtgattgac agtgtttcag aaaaggcaaa tccaaacatt   8100
aaagattcaa aagataatca ggcaaaacaa atgtgggta atggcagtgt tcccatgcgt   8160
accgtgggtt tggaaaatcg cctgaactcc tttattcagg tggatgcccc tgaccaaaaa   8220
ggaactgaga taaaccagg acaaaataat cctgtccctg tatcagagac taatgaaagt   8280
tctatagtgg aacgtacccc attcagttct agcagctcaa gcaaacacag ttcacctagt   8340
gggactgttg ctgccagagt gactcctttt aattacaacc caagccctag gaaaagcagc   8400
gcagatagca cttcagctcg gccatctcag atcccaactc cagtgaataa caacacaaag   8460
aagcgagatt ccaaaactga cagcacagaa tccagtggaa cccaaagtcc taagcgccat   8520
tctgggtctt accttgtgac atctgtttaa aagagaggaa gaatgaaact aagaaaattc   8580
tatgttaatt acaactgcta tatagacatt ttgtttcaaa tgaaactttA AAAGACTGAA   8640
aaattttgta ataggtttg attcttgtta gagggttttt gttctggaag ccatatttga   8700
tagtatactt tgtcttcact ggtcttattt tgggaggcac tcttgatggt taggaaaaaa   8760
atagtaaagc caagtatgtt tgtacagtat gttttacatg tatttaaagt agcacccatc   8820
ccaacttcct ttaattattg cttgtcttaa aataatgaac actacagata gaaaatatga   8880
tatattgctg ttatcaatca tttctagatt ataaactgac taaacttaca tcagggaaaa   8940
attggtattt atgcaaaaaa aaatgttttt gt                                 8972

<210> SEQ ID NO 33
<211> LENGTH: 5711
<212> TYPE: DNA
<213> ORGANISM: Homo sapiens

<400> SEQUENCE: 33
agctcgctga gacttcctgg accccgcacc aggctgtggg gtttctcaga taactgggcc     60
cctgcgctca ggaggccttc accctctgct ctgggtaaag ttcattggaa cagaaagaaa    120
tggatttatc tgctcttcgc gttgaagaag tacaaaatgt cattaatgct atgcagaaaa    180
tcttagagtg tcccatctgt ctggagttga tcaaggaacc tgtctccaca agtgtgacc    240 acatattttg caattttgc atgctgaaac ttctcaacca gaagaaaggg ccttcacagt    300 gtccttatg taagaatgat ataaccaaaa ggagcctaca agaagtacg agatttagtc    360 aacttgttga agagctattg aaaatcattt gtgcttttca gcttgacaca ggtttggagt    420
atgcaaacag ctataatttt gcaaaaaagg aaaataactc tcctgaacat ctaaaagatg    480
aagtttctat catccaaagt atgggctaca gaaaccgtgc caaaagactt ctacagagtg    540
aacccgaaaa tccttccttg caggaaacca gtctcagtgt ccaactctct aaccttggaa    600
ctgtgagaac tctgaggaca aagcagcgga tacaacctca aaagacgtct gtctacattg    660
aattgggatc tgattcttct gaagataccg ttaataagc aacttattgc agtgtgggag    720
atcaagaatt gttacaaatc acccctcaag gaaccaggga tgaaatcagt ttggattctg    780
caaaaaaggc tgcttgtgaa ttttctgaga cggatgtaac aaatactgaa catcatcaac    840
```

```
ccagtaataa tgatttgaac accactgaga agcgtgcagc tgagaggcat ccagaaaagt    900
atcagggtag ttctgtttca aacttgcatg tggagccatg tggcacaaat actcatgcca    960
gctcattaca gcatgagaac agcagtttat tactcactaa agacagaatg aatgtagaaa   1020
aggctgaatt ctgtaataaa agcaaacagc ctggcttagc aaggagccaa cataacagat   1080
gggctggaag taaggaaaca tgtaatgata ggcggactcc cagcacagaa aaaaaggtag   1140
atctgaatgc tgatcccctg tgtgagagaa aagaatggaa taagcagaaa ctgccatgct   1200
cagagaatcc tagagatact gaagatgttc cttggataac actaaatagc agcattcaga   1260
aagttaatga gtggttttcc agaagtgatg aactgttagg ttctgatgac tcacatgatg   1320
gggagtctga atcaaatgcc aaagtagctg atgtattgga cgttctaaat gaggtagatg   1380
aatattctgg ttcttcagag aaaatagact tactggccag tgatcctcat gaggctttaa   1440
tatgtaaaag tgaaagagtt cactccaaat cagtagagag taatattgaa gacaaaatat   1500
ttgggaaaac ctatcggaag aaggcaagcc tcccaacttt aagccatgta actgaaaatc   1560
taattatagg agcatttgtt actgagccac agataataca agagcgtccc ctcacaaata   1620
aattaaagcg taaaggaga cctacatcag gccttcatcc tgaggatttt atcaagaaag   1680
cagatttggc agttcaaaag actcctgaaa tgataaatca gggaactaac caaacggagc   1740
agaatggtca gtgatgaat attactaata gtggtcatga gaataaaaca aaaggtgatt   1800
ctattcagaa tgagaaaaat cctaacccaa tagaatcact cgaaaagaa tctgctttca   1860
aaacgaaagc tgaacctata agcagcagta aagcaatat ggaactcgaa ttaaatatcc   1920
acaattcaaa agcacctaaa aagaataggc tgaggaggaa gtcttctacc aggcatattc   1980
atgcgcttga actagtagtc agtagaaatc taagcccacc taattgtact gaattgcaaa   2040
ttgatagttg ttctagcagt gaagagataa agaaaaaaa gtacaaccaa atgccagtca   2100
ggcacagcag aaacctacaa ctcatggaag gtaaagaacc tgcaactgga gccaagaaga   2160
gtaacaagcc aaatgaacag acaagtaaaa gacatgacag cgatactttc ccagagctga   2220
agttaacaaa tgcacctggt tcttttacta agtgttcaaa taccagtgaa cttaaagaat   2280
ttgtcaatcc tagccttcca agagaagaaa agaagagaa actagaaaca gttaaagtgt   2340
ctaataatgc tgaagacccc aaagatctca tgttaagtgg agaaagggtt ttgcaaactg   2400
aaagatctgt agagagtagc agtatttcat tggtacctgg tactgattat ggcactcagg   2460
aaagtatctc gttactggaa gttagcactc tagggaaggc aaaaacagaa ccaaataaat   2520
gtgtgagtca gtgtgcagca tttgaaaacc ccaagggact aattcatggt tgttccaaag   2580
ataatagaaa tgacacagaa ggctttaagt atccattggg acatgaagtt aaccacagtc   2640
gggaaacaag catagaaatg gaagaaagtg aacttgatgc tcagtatttg cagaatacat   2700
tcaaggtttc aaagcgccag tcatttgctc cgttttcaaa tccaggaaat gcagaagagg   2760
aatgtgcaac attctctgcc cactctgggt ccttaaagaa acaaagtcca aaagtcactt   2820
ttgaatgtga acaaaaggaa gaaaatcaag gaaagaatga gtctaatatc aagcctgtac   2880
agacagttaa tatcactgca ggctttcctg tggttggtca gaaagataag ccagttgata   2940
atgccaaatg tagtatcaaa ggaggctcta ggttttgtct atcatctcag ttcagaggca   3000
acgaaactgg actcattact ccaaataaac atggactttt acaaaaccca tatcgtatac   3060
caccactttt tcccatcaag tcatttgtta aaactaaatg taagaaaaat ctgctagagg   3120
aaaactttga ggaacattca atgtcacctg aagagaaat gggaaatgag aacattccaa   3180
gtacagtgag cacaattagc cgtaataaca ttagagaaaa tgttttttaaa gaagccagct   3240
```

-continued

```
caagcaatat taatgaagta ggttccagta ctaatgaagt gggctccagt attaatgaaa   3300
taggttccag tgatgaaaac attcaagcag aactaggtag aaacagaggg ccaaaattga   3360
atgctatgct tagattaggg gttttgcaac ctgaggtcta taaacaaagt cttcctggaa   3420
gtaattgtaa gcatcctgaa ataaaaaagc aagaatatga agaagtagtt cagactgtta   3480
atacagattt ctctccatat ctgatttcag ataacttaga acagcctatg ggaagtagtc   3540
atgcatctca ggtttgttct gagacacctg atgacctgtt agatgatggt gaaataaagg   3600
aagatactag ttttgctgaa aatgacatta aggaaagttc tgctgttttt agcaaaagcg   3660
tccagaaagg agagcttagc aggagtccta gcccttttcac ccatacacat ttggctcagg   3720
gttaccgaag aggggccaag aaattagagt cctcagaaga gaacttatct agtgaggatg   3780
aagagcttcc ctgcttccaa cacttgttat ttggtaaagt aaacaatata ccttctcagt   3840
ctactaggca tagcaccgtt gctaccgagt gtctgtctaa aacacagag gagaatttat   3900 tatcattgaa gaatagctta aatgactgca gtaaccaggt aatattggca aaggcatctc   3960
aggaacatca ccttagtgag gaaacaaaat gttctgctag cttgttttct tcacagtgca   4020
gtgaattgga agacttgact gcaaatacaa acacccagga tcctttcttg attggttctt   4080
ccaaacaaat gaggcatcag tctgaaagcc agggagttgg tctgagtgac aaggaattgg   4140
tttcagatga tgaagaaaga ggaacgggct tggaagaaaa taatcaagaa gagcaaagca   4200
tggattcaaa cttaggtgaa gcagcatctg ggtgtgagag tgaaacaagc gtctctgaag   4260
actgctcagg gctatcctct cagagtgaca ttttaaccac tcagcagagg gataccatgc   4320
aacataacct gataaagctc cagcaggaaa tggctgaact agaagctgtg ttagaacagc   4380
atgggagcca gccttctaac agctaccctt ccatcataag tgactcttct gcccttgagg   4440
acctgcgaaa tccagaacaa agcacatcag aaaaagcagt attaacttca cagaaaagta   4500
gtgaataccc tataagccag aatccagaag gcctttctgc tgacaagttt gaggtgtctg   4560
cagatagttc taccagtaaa aataaagaac caggagtgga aaggtcatcc ccttctaaat   4620
gcccatcatt agatgatagg tggtacatgc acagttgctc tgggagtctt cagaatagaa   4680
actacccatc tcaagaggag ctcattaagg ttgttgatgt ggaggagcaa cagctggaag   4740
agtctgggcc acacgatttg acggaaacat cttacttgcc aaggcaagat ctagagggaa   4800
ccccttacct ggaatctgga atcagcctct tctctgatga ccctgaatct gatccttctg   4860
aagacagagc cccagagtca gctcgtgttg gcaacatacc atcttcaacc tctgcattga   4920
aagttcccca attgaaagtt gcagaatctg cccagagtcc agctgctgct catactactg   4980
atactgctgg gtataatgca atggaagaaa gtgtgagcag ggagaagcca gaattgacag   5040
cttcaacaga aagggtcaac aaaagaatgt ccatggtggt gtctggcctg accccagaag   5100
aatttatgct cgtgtacaag tttgccagaa acaccacat cactttaact aatctaatta   5160
ctgaagagac tactcatgtt gttatgaaaa cagatgctga gtttgtgtgt gaacggacac   5220
tgaaatattt tctaggaatt gcgggaggaa aatgggtagt tagctatttc tgggtgaccc   5280
agtctattaa agaaagaaaa atgctgaatg agcatgattt tgaagtcaga ggagatgtgg   5340
tcaatggaag aaaccaccaa ggtccaaagc gagcaagaga atcccaggac agaaagatct   5400 tcaggggggct agaaatctgt tgctatgggc ccttcaccaa catgcccaca gatcaactgg   5460
aatggatggt acagctgtgt ggtgcttctg tggtgaagga gctttcatca ttcacccttg   5520
gcacaggtgt ccacccaatt gtggttgtgc agccagatgc ctggacagag gacaatggct   5580
```

| | |
|---|---|
| tccatgcaat tgggcagatg tgtgaggcac ctgtggtgac ccgagagtgg gtgttggaca | 5640 |
| gtgtagcact ctaccagtgc caggagctgg acacctacct gatacccag atcccccaca | 5700 |
| gccactactg a | 5711 |

<210> SEQ ID NO 34
<211> LENGTH: 2680
<212> TYPE: DNA
<213> ORGANISM: Homo sapiens

<400> SEQUENCE: 34

| | |
|---|---|
| ggttatcctg aatacatgtc taacaatttt ccttgcaacg ttagctgttg tttttcactg | 60 |
| tttccaaagg atcaaaattg cttcagaaat tggagacata tttgatttaa aaggaaaaac | 120 |
| ttgaacaaat ggacaatatg tctattacga atacaccaac aagtaatgat gcctgtctga | 180 |
| gcattgtgca tagtttgatg tgccatagac aaggtggaga gagtgaaaca tttgcaaaaa | 240 |
| gagcaattga agtttggta aagaagctga aggagaaaaa agatgaattg gattctttaa | 300 |
| taacagctat aactacaaat ggagctcatc ctagtaaatg tgttaccata cagagaacat | 360 |
| tggatgggag gcttcaggtg gctggtcgga aaggatttcc tcatgtgatc tatgcccgtc | 420 |
| tctggaggtg gcctgatctt cacaaaaatg aactaaaaca tgttaaatat tgtcagtatg | 480 |
| cgtttgactt aaaatgtgat agtgtctgtg tgaatccata tcactacgaa cgagttgtat | 540 |
| cacctggaat tgatctctca ggattaacac tgcagagtaa tgctccatca agtatgatgg | 600 |
| tgaaggatga atatgtgcat gactttgagg acagccatc gttgtccact gaaggacatt | 660 |
| caattcaaac catccagcat ccaccaagta atcgtgcatc gacagagaca tacagcaccc | 720 |
| cagctctgtt agccccatct gagtctaatg ctaccagcac tgccaacttt cccaacattc | 780 |
| ctgtggcttc cacaagtcag cctgccagta tactgggggg cagccatagt gaaggactgt | 840 |
| tgcagatagc atcagggcct cagccaggac agcagcagaa tggatttact ggtcagccag | 900 |
| ctacttacca tcataacagc actaccacct ggactggaag taggactgca ccatacacac | 960 |
| ctaatttgcc tcaccaccaa acggccatc ttcagcacca cccgcctatg ccgccccatc | 1020 |
| ccggacatta ctggcctgtt cacaatgagc ttgcattcca gcctcccatt tccaatcatc | 1080 |
| ctgctcctga gtattggtgt tccattgctt actttgaaat ggatgttcag gtaggagaga | 1140 |
| catttaaggt tccttcaagc tgccctattg ttactgttga tggatacgtg gacccttctg | 1200 |
| gaggagatcg cttttgtttg ggtcaactct ccaatgtcca caggacagaa gccattgaga | 1260 |
| gagcaaggtt gcacataggc aaaggtgtgc agttggaatg taaaggtgaa ggtgatgttt | 1320 |
| gggtcaggtg ccttagtgac cacgcggtct ttgtacagag ttactactta gacagagaag | 1380 |
| ctgggcgtgc acctggagat gctgttcata agatctaccc aagtgcatat ataaaggtct | 1440 |
| ttgatttgcg tcagtgtcat cgacagatgc agcagcaggc ggctactgca caagctgcag | 1500 |
| cagctgccca ggcagcagcc gtggcaggaa acatccctgg cccaggatca gtaggtggaa | 1560 |
| tagctccagc tatcagtctg tcagctgctg ctggaattgg tgttgatgac cttcgtcgct | 1620 |
| tatgcatact caggatgagt tttgtgaaag gctggggacc ggattaccca agacagagca | 1680 |
| tcaaagaaac accttgctgg attgaaattc acttacaccg ggccctccag ctcctagacg | 1740 |
| aagtacttca taccatgccg attgcagacc cacaaccttt agactgaggt cttttaccgt | 1800 |
| tggggccctt aaccttatca ggatggtgga ctacaaaata caatcctgtt tataatctga | 1860 |
| agatatattt cactttctt ctgctttatc ttttcataaa gggttgaaaa tgtgtttgct | 1920 |
| gccttgctcc tagcagacag aaactggatt aaaacaattt ttttttcctc ttcagaactt | 1980 |

```
gtcaggcatg gctcagagct tgaagattag gagaaacaca ttcttattaa ttcttcacct    2040
gttatgtatg aaggaatcat tccagtgcta gaaaatttag ccctttaaaa cgtcttagag    2100 cctttatct gcagaacatc gatatgtata tcattctaca gaataatcca gtattgctga    2160 tttaaaggc agagaagttc tcaaagttaa ttcacctatg ttattttgtg tacaagttgt    2220
tattgttgaa catacttcaa aaataatgtg ccatgtgggt gagttaattt taccaagagt    2280
aactttactc tgtgtttaaa aatgaagtta ataatgtatt gtaatctttc atccaaaata    2340
ttttttgcaa gttatattag tgaagatggt ttcaattcag attgtcttgc aacttcagtt    2400
ttatttttgc caaggcaaaa aactcttaat ctgtgtgtat attgagaatc ccttaaaatt    2460
accagacaaa aaaatttaaa attacgtttg ttattcctag tggatgactg ttgatgaagt    2520
atacttttcc cctgttaaac agtagttgta ttcttctgta tttctaggca caaggttggt    2580
tgctaagaag cctataagag gaatttcttt tccttcattc atagggaaag gttttgtatt    2640
ttttaaaaca ctaaaagcag cgtcactcta cctaatgtct                          2680
```

<210> SEQ ID NO 35
<211> LENGTH: 1095
<212> TYPE: DNA
<213> ORGANISM: Homo sapiens

<400> SEQUENCE: 35

```
tccccgctct gctctgtccg gtcacaggac ttttgccct ctgttcccgg gtccctcagg      60
cggccaccca gtgggcacac tcccaggcgg cgctccggcc ccgcgctccc tccctctgcc    120
tttcattccc agctgtcaac atcctggaag ctttgaagct caggaaagaa gagaaatcca    180
ctgagaacag tctgtaaagg tccgtagtgc tatctcatc cagacggtgg aagggagaga    240
aagagaaaga aggtatccta ggaataccctg cctgcttaga ccctctataa aagctctgtg    300
catcctgcca ctgaggactc cgaagaggta gcagtcttct gaaagacttc aactgtgagg    360
acatgtcgtt cagatttggc caacatctca tcaagccctc tgtagtgttt ctcaaaacag    420
aactgtcctt cgctcttgtg aataggaaac ctgtggtacc aggacatgtc cttgtgtgcc    480
cgctgcggcc agtggagcgc ttccatgacc tgcgtcctga tgaagtggcc gatttgtttc    540
agacgaccca gagagtcggg acagtggtgg aaaaacattt ccatgggacc tctctcacct    600
tttccatgca ggatggcccc gaagccggac agactgtgaa gcacgttcac gtccatgttc    660
ttcccaggaa ggctggagac tttcacagga atgacagcat ctatgaggag ctccagaaac    720
atgacaagga ggactttcct gcctcttgga gatcagagga ggaaatggca gcagaagccg    780
cagctctgcg ggtctacttt cagtgacaca gatgttttc agatcctgaa ttccagcaaa    840
agagctattg ccaaccagtt tgaagaccgc ccccccgcct ctccccaaga ggaactgaat    900
cagcatgaaa atgcagtttc ttcatctcac catcctgtat tcttcaacca gtgatccccc    960
acctcggtca ctccaactcc cttaaaatac ctagacctaa acggctcaga caggcagatt   1020
tgaggtttcc ccctgtctcc ttattcggca gccttatgat taaacttcct tctctgctgc   1080
aaaaaaaaaa aaaaa                                                   1095
```

<210> SEQ ID NO 36
<211> LENGTH: 2234
<212> TYPE: DNA
<213> ORGANISM: Homo sapiens

<400> SEQUENCE: 36

| | |
|---|---:|
| aggggacgca gcgaaaccgg ggcccgcgcc aggccagccg ggacggacgc cgatgcccgg | 60 |
| ggctgcgacg gctgcagagc gagctgccct cggaggccgg cgtggggaag atggcccagt | 120 |
| ccaccgccac ctcccctgat gggggcacca cgtttgagca cctctggagc tctctggaac | 180 |
| cagacagcac ctacttcgac cttcccagt caagccgggg gaataatgag gtggtgggcg | 240 |
| gaacggattc cagcatggac gtcttccacc tggagggcat gactacatct gtcatggccc | 300 |
| agttcaatct gctgagcagc accatggacc agatgagcag ccgcgcggcc tcggccagcc | 360 |
| cctacacccc agagcacgcc gccagcgtgc ccacccactc gccctacgca caacccagct | 420 |
| ccaccttcga caccatgtcg ccggcgcctg tcatcccctc caacaccgac taccccggac | 480 |
| cccaccactt tgaggtcact ttccagcagt ccagcacggc caagtcagcc acctggacgt | 540 |
| actccccgct cttgaagaaa ctctactgcc agatcgccaa gacatgcccc atccagatca | 600 |
| aggtgtccac cccgccaccc ccaggcactg ccatccgggc catgcctgtt tacaagaaag | 660 |
| cggagcacgt gaccgacgtc gtgaaacgct gccccaacca cgagctcggg agggacttca | 720 |
| acgaaggaca gtctgctcca gccagccacc tcatccgcgt ggaaggcaat aatctctcgc | 780 |
| agtatgtgga tgaccctgtc accggcaggc agagcgtcgt ggtgccctat gagccaccac | 840 |
| aggtggggac ggaattcacc accatcctgt acaacttcat gtgtaacagc agctgtgtag | 900 |
| ggggcatgaa ccggcggccc atcctcatca tcatcaccct ggagatgcgg gatgggcagg | 960 |
| tgctgggccg ccggtccttt gagggccgca tctgcgcctg tcctggccgc gaccgaaaag | 1020 |
| ctgatgagga ccactaccgg gagcagcagg ccctgaacga gagctccgcc aagaacgggg | 1080 |
| ccgccagcaa gcgtgccttc aagcagagcc ccctgccgt ccccgccctt ggtgccggtg | 1140 |
| tgaagaagcg gcggcatgga gacgaggaca cgtactacct tcaggtgcga ggccgggaga | 1200 |
| actttgagat cctgatgaag ctgaaagaga gcctggagct gatggagttg gtgccgcagc | 1260 |
| cactggtgga ctcctatcgg cagcagcagc agctcctaca gaggccgagt cacctacagc | 1320 |
| ccccgtccta cgggccggtc ctctcgccca tgaacaaggt gcacggggc atgaacaagc | 1380 |
| tgccctccgt caaccagctg gtgggccagc ctccccgca cagttcggca gctacaccca | 1440 |
| acctgggcc cgtgggcccc gggatgctca caaccatgg ccacgcagtg ccagccaacg | 1500 |
| gcgagatgag cagcagccac agcgcccagt ccatggtctc ggggtcccac tgcactccgc | 1560 |
| cacccccta ccacgccgac cccagcctcg tcagtttttt aacaggattg gggtgtccaa | 1620 |
| actgcatcga gtatttcacc tcccaagggt tacagagcat ttaccacctg cagaacctga | 1680 |
| ccattgagga cctgggggcc ctgaagatcc ccgagcagta ccgcatgacc atctggcggg | 1740 |
| gcctgcagga cctgaagcag ggccacgact acagcaccgc gcagcagctg ctccgctcta | 1800 |
| gcaacgcggc caccatctcc atcggcggct caggggaact gcagcgccag cgggtcatgg | 1860 |
| aggccgtgca cttccgcgtg cgccacacca tcaccatccc caaccgcggc ggcccaggcg | 1920 |
| gcggccctga cgagtgggcg gacttcggct tcgacctgcc cgactgcaag gcccgcaagc | 1980 |
| agcccatcaa ggaggagttc acggaggccg agatccactg agggcctcgc ctggctgcag | 2040 |
| cctcgccac cgcccagaga cccaagctgc ctcccctctc cttcctgtgt gtccaaaact | 2100 |
| gcctcaggag gcaggaccctt cgggctgtgc ccggggaaag gcaaggtccg gcccatcccc | 2160 |
| aggcacctca caggccccag gaaaggccca gccaccgaag ccgcctgtgg acagcctgag | 2220 |
| tcacctgcag aacc | 2234 |

<210> SEQ ID NO 37
<211> LENGTH: 4344

<212> TYPE: DNA
<213> ORGANISM: Homo sapiens

<400> SEQUENCE: 37

```
atggcctcgg ctggtaacgc cgccgagccc caggaccgcg gcggcggcgg cagcggctgt    60
atcggtgccc cgggacggcc ggctggaggc gggaggcgca gacggacggg ggggctgcgc   120
cgtgctgccg cgccggaccg ggactatctg caccggccca gctactgcga cgccgccttc   180
gctctggagc agatttccaa ggggaaggct actggccgga aagcgccact gtggctgaga   240
gcgaagtttc agagactctt atttaaactg ggttgttaca ttcaaaaaaa ctgcggcaag   300
ttcttggttg tgggcctcct catatttggg gccttcgcgg tgggattaaa agcagcgaac   360
ctcgagacca acgtggagga gctgtgggtg aagttggag gacgagtaag tcgtgaatta   420
aattatactc gccagaagat tggagaagag gctatgttta atcctcaact catgatacag   480
acccctaaag aagaaggtgc taatgtcctg accacagaag cgctcctaca cacctggac   540
tcggcactcc aggccagccg tgtccatgta tacatgtaca acaggcagtg gaaattggaa   600
catttgtgtt acaaatcagg agagcttatc acagaaacag gttacatgga tcagataata   660
gaatatcttt acccttgttt gattattaca cctttggact gcttctggga aggggcgaaa   720
ttacagtctg ggacagcata cctcctaggt aaacctcctt tgcggtggac aaacttcgac   780
cctttggaat tcctggaaga gttaaagaaa ataaactatc aagtggacag ctggaggaa   840
atgctgaata aggctgaggt tggtcatggt tacatggacc gcccctgcct caatccggcc   900
gatccagact gccccgccac agcccccaac aaaaattcaa ccaaacctct tgatatggcc   960
cttgttttga atggtggatg tcatggctta tccagaaagt atatgcactg gcaggaggag  1020
ttgattgtgg gtggcacagt caagaacagc actggaaaac tcgtcagcgc ccatgccctg  1080
cagaccatgt tccagttaat gactcccaag caaatgtacg agcacttcaa ggggtacgag  1140
tatgtctcac acatcaactg gaacgaggac aaagcggcag ccatcctgga ggcctggcag  1200
aggacatatg tggaggtggt tcatcagagt gtcgcacaga actccactca aaaggtgctt  1260
tccttcacca ccacgaccct ggacgacatc ctgaaatcct tctctgacgt cagtgtcatc  1320
cgcgtggcca gcggctactt actcatgctc gcctatgcct gtctaaccat gctgcgctgg  1380
gactgctcca gtcccagggg tgccgtgggg ctggctggcg tcctgctggt tgcactgtca  1440
gtggctgcag gactgggcct gtgctcattg atcggaattt cctttaacgc tgcaacaact  1500
caggttttgc catttctcgc tcttggtgtt ggtgtggatg atgttttctt tctggcccac  1560
gccttcagtg aaacaggaca gaataaaaga atccctttg aggacaggac cggggagtgc  1620
ctgaagcgca caggagccag cgtggccctc acgtccatca gcaatgtcac agccttcttc  1680
atggccgcgt taatcccaat tcccgctctg cgggcgttct ccctccaggc agcggtagta  1740
gtggtgttca attttgccat ggttctgctc atttttcctg caattctcag catggattta  1800
tatcgacgcg aggacaggag actggatatt ttctgctgtt ttacaagccc ctgcgtcagc  1860
agagtgattc aggttgaacc tcaggcctac accgacacac acgacaatac ccgctacagc  1920
cccccacctc cctacagcag ccacagcttt gcccatgaaa cgcagattac catgcagtcc  1980
actgtccagc tccgcacgga gtacgacccc cacacgcacg tgtactacac caccgctgag  2040
ccgcgctccg agatctctgt gcagcccgtc accgtgacac aggacaccct cagctgccag  2100
agcccagaga gcaccagctc cacaagggac ctgctctccc agttctccga ctccagcctc  2160
cactgcctcg agcccccctg tacgaagtgg acactctcat cttttgctga gaagcactat  2220
```

```
gctcctttcc tcttgaaacc aaaagccaag gtagtggtga tcttccttt  tctgggcttg  2280 ctggggtca  gcctttatgg caccacccga gtgagagacg ggctggacct tacggacatt   2340
gtacctcggg aaaccagaga atatgacttt attgctgcac aattcaaata cttttctttc   2400
tacaacatgt atatagtcac ccagaaagca gactacccga atatccagca cttactttac   2460
gacctacaca ggagtttcag taacgtgaag tatgtcatgt tggaagaaaa caaacagctt   2520
cccaaaatgt ggctgcacta cttcagagac tggcttcagg gacttcagga tgcatttgac   2580
agtgactggg aaaccgggaa aatcatgcca aacaattaca agaatggatc agacgatgga   2640
gtccttgcct acaaactcct ggtgcaaacc ggcagccgcg ataagcccat cgacatcagc   2700
cagttgacta acagcgtct  ggtggatgca gatggcatca ttaatcccag cgctttctac   2760
atctacctga cggcttgggt cagcaacgac cccgtcgcgt atgctgcctc ccaggccaac   2820
atccggccac accgaccaga atgggtccac gacaaagccg actacatgcc tgaaacaagg   2880
ctgagaatcc cggcagcaga gcccatcgag tatgcccagt ccctttctta cctcaacggg   2940
ttgcgggaca cctcagactt tgtggaggca attgaaaaag taaggaccat ctgcagcaac   3000
tatacgagcc tggggctgtc cagttacccc aacggctacc ccttcctctt ctgggagcag   3060
tacatcggcc tccgccactg gctgctgctg ttcatcagcg tggtgttggc ctgcacattc   3120
ctcgtgtgcg ctgtcttcct tctgaacccc tggacggccg ggatcattgt gatggtcctg   3180
gcgctgatga cggtcgagct gttcggcatg atgggcctca tcggaatcaa gctcagtgcc   3240
gtgcccgtgg tcatcctgat cgcttctgtt ggcataggag tggagttcac cgttcacgtt   3300
gctttggcct ttctgacggc catcggcgac aagaaccgca gggctgtgct tgccctggag   3360
cacatgtttg cacccgtcct ggatggcgcc gtgtccactc tgctgggagt gctgatgctg   3420
gcgggatctg agttcgactt cattgtcagg tatttctttg ctgtgctggc gatcctcacc   3480
atcctcggcg ttctcaatgg gctggttttg cttcccgtgc ttttgtcttt ctttggacca   3540
tatcctgagg tgtctccagc caacggcttg aaccgcctgc ccacaccctc ccctgagcca   3600
ccccccagcg tggtccgctt cgccatgccg cccggccaca cgcacagcgg gtctgattcc   3660
tccgactcgg agtatagttc ccagacgaca gtgtcaggcc tcagcgagga gcttcggcac   3720
tacgaggccc agcagggcgc gggaggccct gcccaccaag tgatcgtgga agccacagaa   3780
aaccccgtct tcgcccactc cactgtggtc catcccgaat ccaggcatca cccaccctcg   3840 aaccccgagac agcagcccca cctggactca gggtccctgc ctcccggacg gcaaggccag   3900
cagccccgca gggaccccc  cagagaaggc ttgtggccac ccctctacag accgcgcaga   3960
gacgcttttg aaatttctac tgaagggcat tctggcccta gcaatagggc ccgctggggc   4020
cctcgcgggg cccgttctca aaccctcgg  aacccagcgt ccactgccat gggcagctcc   4080
gtgcccggct actgccagcc catcaccact gtgacggctt ctgcctccgt gactgtcgcc   4140
gtgcacccgc cgcctgtccc tgggcctggg cggaaccccc gaggggggact ctgcccaggc   4200 taccctgaga ctgaccacgg cctgtttgag gaccccacg  tgcctttcca cgtccggtgt   4260
gagaggaggg attcgaaggt ggaagtcatt gagctgcagg acgtggaatg cgaggagagg   4320
ccccggggaa gcagctccaa ctga                                        4344
```

<210> SEQ ID NO 38
<211> LENGTH: 4740
<212> TYPE: DNA
<213> ORGANISM: Homo sapiens

<400> SEQUENCE: 38

```
ttccggtttt tctcagggga cgttgaaatt attttgtaa cgggagtcgg gagaggacgg     60
ggcgtgcccc gcgtgcgcgc gcgtcgtcct ccccggcgct cctccacagc tcgctggctc    120
ccgccgcgga aaggcgtcat gccgcccaaa acccccgaa aaacggccgc caccgccgcc     180
gctgccgccg cggaaccccc ggcaccgccg ccgccgcccc ctcctgagga ggacccagag    240
caggacagcg gcccggagga cctgcctctc gtcaggcttg agtttgaaga aacagaagaa    300
cctgatttta ctgcattatg tcagaaatta aagataccag atcatgtcag agagagagct    360
tggttaactt gggagaaagt ttcatctgtg gatggagtat gggaggtta tattcaaaag    420 aaaaaggaac tgtggggaat ctgtatcttt attgcacgag ttgacctaga tgagatgtcg    480
ttcactttac tgagctacag aaaaacatac gaaatcagtg tccataaatt ctttaactta    540
ctaaaagaaa ttgataccag taccaaagtt gataatgcta tgtcaagact gttgaagaag    600
tatgatgtat tgtttgcact cttcagcaaa ttggaaagga catgtgaact tatatatttg    660
acacaaccca gcagttcgat atctactgaa ataaattctg cattggtgct aaaagtttct    720
tggatcacat ttttattagc taaaggggaa gtattacaaa tggaagatga tctggtgatt    780
tcatttcagt taatgctatg tgtccttgac tatttttatta aactctcacc tcccatgttg    840
ctcaaagaac catataaaac agctgttata cccattaatg gttcacctcg aacacccagg    900
cgaggtcaga acaggagtgc acggatagca aaacaactag aaaatgatac aagaattatt    960
gaagttctct gtaaagaaca tgaatgtaat atagatgagg tgaaaaatgt ttatttcaaa   1020 aatttttatac cttttatgaa ttctcttgga cttgtaacat ctaatggact tccagaggtt   1080 gaaaatctttt ctaaacgata cgaagaaatt tatcttaaaa ataaagatct agatcgaaga   1140 ttattttgg atcatgataa aactcttcag actgattcta tagacagttt tgaaacacag   1200
agaacaccac gaaaaagtaa ccttgatgaa gaggtgaata taattcctcc acacactcca   1260
gttaggactg ttatgaacac tatccaacaa ttaatgatga ttttaaattc tgcaagtgat   1320
caaccttcag aaaatctgat ttcctatttt aacaactgca cagtgaatcc aaaagaaagt   1380
atactgaaaa gagtgaagga tataggatac atctttaaag agaaatttgc taaagctgtg   1440
ggacagggtt gtgtcgaaat tggatcacag cgatacaaac ttggagttcg cttgtattac   1500
cgagtaatgg aatccatgct taaatcagaa gaagaacgat tatccattca aaatttttagc   1560 aaacttctga tgacaacat ttttcatatg tctttattgg cgtgcgctct tgaggttgta   1620
atggccacat atagcagaag tacatctcag aatcttgatt ctggaacaga tttgtctttc   1680
ccatggattc tgaatgtgct taattttaaaa gcctttgatt tttacaaagt gatcgaaagt   1740
tttatcaaag cagaaggcaa cttgacaaga gaaatgataa acatttaga acgatgtgaa   1800 catcgaatca tggaatccct tgcatggctc tcagattcac cttttatttga tcttattaaa   1860 caatcaaagg accgagaagg accaactgat caccttgaat ctgcttgtcc tcttaatctt   1920
cctctccaga taatcacac tgcagcagat atgtatcttt ctcctgtaag atctccaaag   1980
aaaaaaggtt caactacgcg tgtaaattct actgcaaatg cagagacaca agcaacctca   2040
gccttccaga cccagaagcc attgaaatct acctctcttt cactgtttta taaaaaagtg   2100
tatcggctag cctatctccg gctaaataca cttttgtgaac gccttctgtc tgagcaccca   2160
gaattagaac atatcatctg gaccctttttc cagcacaccc tgcagaatga gtatgaactc   2220
atgagagaca ggcatttgga ccaaattatg atgtgttcca tgtatggcat atgcaaagtg   2280
aagaatatag accttaaatt caaaatcatt gtaacagcat acaaggatct tcctcatgct   2340
```

```
gttcaggaga cattcaaacg tgttttgatc aaagaagagg agtatgattc tattatagta    2400
ttctataact cggtcttcat gcagagactg aaaacaaata ttttgcagta tgcttccacc    2460
aggcccccta ccttgtcacc aatacctcac attcctcgaa gcccttacaa gtttcctagt    2520
tcacccttac ggattcctgg agggaacatc tatatttcac ccctgaagag tccatataaa    2580
atttcagaag gtctgccaac accaacaaaa atgactccaa gatcaagaat cttagtatca    2640
attggtgaat cattcgggac ttctgagaag ttccagaaaa taaatcagat ggtatgtaac    2700
agcgaccgtg tgctcaaaag aagtgctgaa ggaagcaacc ctcctaaacc actgaaaaaa    2760
ctacgctttg atattgaagg atcagatgaa gcagatggaa gtaaacatct cccaggagag    2820
tccaaatttc agcagaaact ggcagaaatg acttctactc gaacacgaat gcaaaagcag    2880
aaaatgaatg atagcatgga tacctcaaac aaggaagaga atgaggatc tcaggacctt    2940 ggtggacact gtgtacacct ctggattcat tgtctctcac agatgtgact gtataacttt    3000
cccaggttct gtttatggcc acatttaata tcttcagctc ttttttgtgga tataaaatgt    3060 gcagatgcaa ttgtttgggt gagtcctaag ccacttgaaa tgttagtcat tgttatttat    3120
acaagattga aaatcttgtg taaatcctgc catttaaaaa gttgtagcag attgtttcct    3180
cttccaaagt aaaattgctg tgctttatgg atagtaagaa tggccctaga gtgggagtcc    3240
tgataaccca ggcctgtctg actactttgc cttcttttgt agcatatagg tgatgtttgc    3300
tcttgttttt attaatttat atgtatattt ttttaattta acatgaacac ccttagaaaa    3360
tgtgtcctat ctatcttcca aatgcaattt gattgactgc ccattcacca aaattatcct    3420
gaactcttct gcaaaatgg atattattag aaattagaaa aaaattacta attttacaca    3480 ttagattta ttttactatt ggaatctgat atactgtgtg cttgttttat aaaattttgc    3540
ttttaattaa ataaaagctg gaagcaaagt ataaccatat gatactatca tactactgaa    3600
acagatttca tacctcagaa tgtaaagaa cttactgatt attttcttca tccaacttat    3660
gtttttaaat gaggattatt gatagtactc ttggtttta taccattcag atcactgaat    3720
ttataaagta cccatctagt acttgaaaaa gtaaagtgtt ctgccagatc ttaggtatag    3780
aggaccctaa cacagtatat cccaagtgca ctttctaatg tttctgggtc ctgaagaatt    3840
aagatacaaa ttaattttac tccataaaca gactgttaat tataggagcc ttaattttt    3900 tttcatagag atttgtctaa ttgcatctca aaattattct gccctcctta atttgggaag    3960
gtttgtgttt tctctggaat ggtacatgtc ttccatgtat cttttgaact ggcaattgtc    4020
tatttatctt ttattttttt aagtcagtat ggtctaacac tggcatgttc aaagccacat    4080
tatttctagt ccaaaattac aagtaatcaa gggtcattat gggttaggca ttaatgtttc    4140
tatctgattt tgtgcaaaag cttcaaatta aaacagctgc attagaaaaa gaggcgcttc    4200
tcccctcccc tacacctaaa ggtgtattta aactatcttg tgtgattaac ttatttagag    4260
atgctgtaac ttaaaatagg ggatatttaa ggtagcttca gctagctttt aggaaaatca    4320
ctttgtctaa ctcagaatta tttttaaaaa gaaatctggt cttgttagaa aacaaaattt    4380
tattttgtgc tcatttaagt ttcaaactta ctattttgac agttattttg ataacaatga    4440
cactagaaaa cttgactcca tttcatcatt gtttctgcat gaatatcata caaatcagtt    4500 agttttagg tcaagggctt actatttctg ggtcttttgc tactaagttc acattagaat    4560
tagtgccaga attttaggaa cttcagagat cgtgtattga gatttcttaa ataatgcttc    4620
agatattatt gctttattgc ttttttgtat tggttaaaac tgtacattta aaattgctat    4680
gttactattt tctacaatta atagtttgtc tattttaaaa taaattagtt gttaagagtc    4740
```

<210> SEQ ID NO 39
<211> LENGTH: 4608
<212> TYPE: DNA
<213> ORGANISM: Homo sapiens

<400> SEQUENCE: 39

```
atggagaata gtcttagatg tgtttgggta cccaagctgg cttttgtact cttcggagct      60
tccttgctca gcgcgcatct tcaagtaacc ggttttcaaa ttaaagcttt cacagcactg     120
cgcttcctct cagaaccttc tgatgccgtc acaatgcggg aggaaatgt cctcctcgac      180
tgctccgcgg agtccgaccg aggagttcca gtgatcaagt ggaagaaaga tggcattcat     240
ctggccttgg aatggatga aaggaagcag caactttcaa atgggtctct gctgatacaa      300
aacatacttc attccagaca ccacaagcca gatgagggac tttaccaatg tgaggcatct     360
ttaggagatt ctggctcaat tattagtcgg acagcaaaag ttgcagtagc aggaccactg     420
aggttccttt cacagacaga atctgtcaca gccttcatgg agacacagt gctactcaag      480
tgtgaagtca ttggggagcc catgccaaca atccactggc agaagaacca acaagacctg    540
actccaatcc caggtgactc ccgagtggtg gtcttgccct ctggagcatt gcagatcagc    600
cgactccaac cgggggacat tggaatttac cgatgctcag ctcgaaatcc agccagctca    660
agaacaggaa atgaagcaga agtcagaatt ttatcagatc caggactgca tagacagctg    720
tattttctgc aaagaccatc caatgtagta gccattgaag gaaagatgc tgtcctggaa     780
tgttgtgttt ctggctatcc tccaccaagt tttacctggt tacgaggcga ggaagtcatc    840
caactcaggt ctaaaaagta ttctttattg ggtggaagca acttgcttat ctccaatgtg    900
acagatgatg acagtggaat gtatacctgt gttgtcacat ataaaaatga gaatattagt    960
gcctctgcag agctcacagt cttggttccg ccatggtttt taaatcatcc ttccaacctg   1020
tatgcctatg aaagcatgga tattgagttt gaatgtacag tctctggaaa gcctgtgccc   1080
actgtgaatt ggatgaagaa tggagatgtg gtcattccta gtgattattt tcagatagtg   1140
ggaggaagca acttacggat acttggggtg gtgaagtcag atgaaggctt ttatcaatgt   1200
gtggctgaaa atgaggctgg aaatgcccag accagtgcac agctcattgt ccctaagcct   1260
gcaatcccaa gctccagtgt cctcccttcg gctcccagag atgtggtccc tgtcttggtt   1320
ccagccgat ttgtccgtct cagctggcgc ccacctgcag aagcgaaagg aacattcaa    1380
actttcacgg tcttttcctc cagagaaggt gacaacaggg aacgagcatt gaatacaaca   1440
cagcctgggt cccttcagct cactgtggga aacctgaagc cagaagccat gtacacctt   1500
cgagttgtgg cttacaatga atggggaccg ggagagagtt ctcaacccat caaggtggcc    1560
acacagcctg agttgcaagt tccagggcca gtagaaaacc tgcaagctgt atctacctca    1620
cctacctcaa ttcttattac ctgggaaccc ctgcctatg caaacggtcc agtccaaggt    1680
tacagattgt tctgcactga ggtgtccaca ggaaaagaac agaatataga ggttgatgga    1740
ctatcttata aactggaagg cctgaaaaaa ttcaccgaat atagtcttcg attcttagct    1800
tataatcgct atggtccggg cgtctctact gatgatataa cagtggttac actttctgac    1860
gtgccaagtg ccccgcctca gaacgtctcc ctggaagtgg tcaattcaag aagtatcaaa    1920
gttagctggc tgcctcctcc atcaggaaca caaaatggat ttattaccgg ctataaaatt    1980
cgacacagaa agacgacccg cagggtgag atggaaacac tggagccaaa caacctctgg    2040
tacctattca caggactgga gaaggaagt cagtacagtt ccaggtgtc agccatgaca    2100
```

```
gtcaatggta ctggaccacc ttccaactgg tatactgcag agactccaga gaatgatcta    2160
gatgaatctc aagttcctga tcaaccaagc tctcttcatg tgaggcccca gactaactgc    2220
atcatcatga gttggactcc tcccttgaac ccaaacatcg tggtgcgagg ttatattatc    2280
ggttatggcg ttgggagccc ttacgctgag acagtgcgtg tggacagcaa gcagcgatat    2340
tattccattg agaggttaga gtcaagttcc cattatgtaa tctccctaaa agcttttaac    2400
aatgccggag aaggagttcc tctttatgaa agtgccacca ccaggtctat aaccgatccc    2460
actgacccag ttgattatta cctttgcttt gatgatttcc ccacctcggt cccagatctc    2520
tccaccccca tgctcccacc agtaggtgta caggctgtgg ctcttaccca tgatgctgtg    2580
agggtcagct gggcagacaa ctctgtccct aagaaccaaa agacgtctga ggtgcgactt    2640
tacaccgtcc ggtggagaac cagcttttct gcaagtgcaa atacaagtc agaagacaca    2700 acatctctaa gttacacagc aacaggcctc aaaccaaaca caatgtatga attctcggtc    2760
atggtaacaa aaaacagaag gtccagtact tggagcatga ctgcacatgc caccacgtat    2820
gaagcagccc ccacctctgc tcccaaggac tttacagtca ttactaggga agggaagcct    2880
cgtgccgtca ttgtgagttg gcagcctccc ttggaagcca atgggaaaat tactgcttac    2940
atcttatttt atacctttgga caagaacatc ccaattgatg actggattat ggaaacaatc    3000
agtggtgata ggcttactca tcaaatcatg gatctcaacc ttgatactat gtattacttt    3060
cgaattcaag cacgaaattc aaaaggagtg gggccactct ctgatcccat cctcttcagg    3120
actctgaaag tggaacaccc tgacaaaatg gctaatgacc aaggtcgtca tggagatgga    3180
ggttattggc cagttgatac taatttgatt gatagaagca ccctaaatga ccgccaatt    3240 ggacaaatgc accccccgca tggcagtgtc actcctcaga agaacagcaa cctgcttgtg    3300
atcattgtgg tcaccgttgg tgtcatcaca gtgctggtag tggtcatcgt ggctgtgatt    3360 tgcaccgac gctcttcagc ccagcagaga aagaaacggg ccacccacag tgctggcaaa    3420
aggaagggca gccagaagga cctccgaccc cctgatcttt ggatccatca tgaagaaatg    3480
gagatgaaaa atattgaaaa gccatctggc actgaccctg caggaaggga ctctcccatc    3540
caaagttgcc aagacctcac accagtcagc cacagccagt cagaaaccca actgggaagc    3600
aaaagcacct ctcattcagg tcaagacact gaggaagcag ggagctctat gtccactctg    3660
gagaggtcgc tggctgcacg ccgagccccc cgggccaagc tcatgattcc catggatgcc    3720
cagtccaaca atcctgctgt cgtgagcgcc atcccggtgc aacgctaga aagtgcccag    3780 tacccaggaa tcctcccgtc tcccacctgt ggatatcccc acccgcagtt cactctccgg    3840
cctgtgccat tcccaacact ctcagtggac cgaggtttcg gagcaggaag aagtcagtca    3900
gtgagtgaag gaccaactac ccaacaacca cctatgctgc ccccatctca gcctgagcat    3960
tctagcagcg aggaggcacc aagcagaacc atccccacag cttgtgttcg accaactcac    4020
ccactccgca gctttgctaa tccttttgcta cctccaccaa tgagtgcaat agaaccgaaa    4080
gtcccttaca caccactttt gtctcagcca gggcccactc ttcctaagac ccatgtgaaa    4140
acagcctccc ttgggttggc tggaaaagca agatcccctt gcttcctgt gtctgtgcca    4200 acagcccctg aagtgtctga ggagagccac aaaccaacag aggattcagc caatgtgtat    4260
gaacaggatg atctgagtga acaaatggca agtttggaag gactcatgaa gcagcttaat    4320
gccatcacag gctcagcctt ttaacatgta tttctgaatg gatgaggtga attttccggg    4380
aactttgcag cataccaatt acccataaac agcacacctg tgtccaagaa ctctaaccag    4440
tgtacaggtc acccatcagg accactcagt taaggaagat cctgaagcag ttcagaagga    4500
```

-continued

| | | |
|---|---|---|
| ataagcattc cttctttcac aggcatcagg aattgtcaaa tgatgattat gagttcccta | 4560 | |
| aacaaaagca aagatgcatt ttcactgcaa tgtcaaagtt tagctgct | 4608 | |

<210> SEQ ID NO 40
<211> LENGTH: 8959
<212> TYPE: DNA
<213> ORGANISM: Homo sapiens

<400> SEQUENCE: 40

| | | |
|---|---|---|
| ccccagcctc cttgccaacg ccccctttcc ctctcccccct cccgctcggc gctgaccccc | 60 | |
| catccccacc cccgtgggaa cactgggagc ctgcactcca cagaccctct ccttgcctct | 120 | |
| tccctcacct cagcctccgc tcccgccct cttcccggcc cagggcgccg gcccacccctt | 180 | |
| ccctccgccg cccccccggcc gcggggagga catggccgcg cacaggccgg tggaatgggt | 240 | |
| ccaggccgtg gtcagccgct tcgacgagca gcttccaata aaaacaggac agcagaacac | 300 | |
| acataccaaa gtcagtactg agcacaacaa ggaatgtcta atcaatattt ccaaatacaa | 360 | |
| gttttctttg gttataagcg gcctcactac tatttttaaag aatgttaaca atatgagaat | 420 | |
| atttggagaa gctgctgaaa aaaatttata tctctctcag ttgattatat tggatacact | 480 | |
| ggaaaaatgt cttgctgggc aaccaaagga cacaatgaga ttagatgaaa cgatgctggt | 540 | |
| caaacagttg ctgccagaaa tctgccattt tcttcacacc tgtcgtgaag gaaccagca | 600 | |
| tgcagctgaa cttcggaatt ctgcctctgg ggttttattt tctctcagct gcaacaactt | 660 | |
| caatgcagtc tttagtcgca tttctaccag gttacaggaa ttaactgttt gttcagaaga | 720 | |
| caatgttgat gttcatgata tagaattgtt acagtatatc aatgtggatt gtgcaaaatt | 780 | |
| aaaacgactc ctgaaggaaa cagcatttaa atttaaagcc ctaaagaagg ttgcgcagtt | 840 | |
| agcagttata aatagcctgg aaaaggcatt ttggaactgg gtagaaaatt atccagatga | 900 | |
| atttacaaaa ctgtaccaga tcccacagac tgatatggct gaatgtgcag aaaagctatt | 960 | |
| tgacttggtg gatggttttg ctgaaagcac caaacgtaaa gcagcagttt ggccactaca | 1020 | |
| aatcattctc cttatcttgt gtccagaaat aatccaggat atatccaaag acgtggttga | 1080 | |
| tgaaaacaac atgaataaga agttatttct ggacagtcta cgaaaagctc ttgctggcca | 1140 | |
| tggaggaagt aggcagctga cagaaagtgc tgcaattgcc tgtgtcaaac tgtgtaaagc | 1200 | |
| aagtacttac atcaattggg aagataactc tgtcattttc ctacttgttc agtccatggt | 1260 | |
| ggttgatctt aagaacctgc ttttaatcc aagtaagcca ttctcaagag gcagtcagcc | 1320 | |
| tgcagatgtg gatctaatga ttgactgcct tgtttcttgc tttcgtataa gccctcacaa | 1380 | |
| caaccaacac tttaagatct gcctggctca gaattcacct tctacatttc actatgtgct | 1440 | |
| ggtaaattca ctccatcgaa tcatcaccaa ttccgcattg gattggtggc taagattga | 1500 | |
| tgctgtgtat tgtcactcgg ttgaacttcg aaatatgttt ggtgaaacac ttcataaagc | 1560 | |
| agtgcaaggt tgtggagcac acccagcaat acgaatggca ccgagtctta catttaaaga | 1620 | |
| aaaagtaaca agccttaaat ttaaagaaaa acctacagac ctggagacaa gaagctataa | 1680 | |
| gtatcttctc ttgtccatgg tgaaactaat tcatgcagat ccaaagctct tgctttgtaa | 1740 | |
| tccaagaaaa cagggggccg aaacccaagg cagtacagca gaattaatta cagggctcgt | 1800 | |
| ccaactggtc cctcagtcac acatgccaga gattgctcag gaagcaatgg aggctctgct | 1860 | |
| ggttcttcat cagttagata gcattgattt gtggaatcct gatgctcctg tagaaacatt | 1920 | |
| ttgggagatt agctcacaaa tgcttttttta catctgcaag aaattaacta gtcatcaaat | 1980 | |

```
gcttagtagc acagaaattc tcaagtggtt gcgggaaata ttgatctgca ggaataaatt    2040
tcttcttaaa aataagcagg cagatagaag ttcctgtcac tttctccttt tttacggggt    2100
aggatgtgat attccttcta gtggaaatac cagtcaaatg tccatggatc atgaagaatt    2160
actacgtact cctggagcct ctctccggaa gggaaaaggg aactcctcta tggatagtgc    2220
agcaggatgc agcggaaccc ccccaatttg ccgacaagcc cagaccaaac tagaagtggc    2280
cctgtacatg tttctgtgga accctgacac tgaagctgtt ctggttgcca tgtcctgttt    2340
ccgccacctc tgtgaggaag cagatatccg gtgtggggtg gatgaagtgt cagtgcataa    2400
cctcttgccc aactataaca cattcatgga gtttgcctct gtcagcaata tgatgtcaac    2460
aggaagagca gcacttcaga aaagagtgat ggcactgctg aggcgcattg agcatcccac    2520
tgcaggaaac actgaggctt gggaagatac acatgcaaaa tgggaacaag caacaaagct    2580
aatccttaac tatccaaaag ccaaaatgga agatggccag gctgctgaaa gccttcacaa    2640
gaccattgtt aagaggcgaa tgtcccatgt gagtggagga ggatccatag atttgtctga    2700
cacagactcc ctacaggaat ggatcaacat gactggcttc ctttgtgccc ttggaggagt    2760
gtgcctccag cagagaagca attctggcct ggcaacctat agcccaccca tgggtccagt    2820
cagtgaacgt aagggttcta tgatttcagt gatgtcttca gagggaaacg cagatacacc    2880
tgtcagcaaa tttatggatc ggctgttgtc cttaatggtg tgtaaccatg agaaagtggg    2940
acttcaaata cggaccaatg ttaaggatct ggtgggtcta gaattgagtc ctgctctgta    3000
tccaatgcta tttaacaaat tgaagaatac catcagcaag tttttttgact cccaaggaca    3060 ggttttattg actgatacca atactcaatt tgtagaacaa accatagcta taatgaagaa    3120
cttgctagat aatcatactg aaggcagctc tgaacatcta gggcaagcta gcattgaaac    3180
aatgatgtta aatctggtca ggtatgttcg tgtgcttggg aatatggtcc atgcaattca    3240
aataaaaacg aaactgtgtc aattagttga agtaatgatg gcaaggagag atgacctctc    3300
attttgccaa gagatgaaat ttaggaataa gatggtagaa tacctgacag actgggttat    3360
gggaacatca aaccaagcag cagatgatga tgtaaaatgt cttacaagag atttggacca    3420
ggcaagcatg gaagcagtag tttcacttct agctggtctc cctctgcagc ctgaagaagg    3480
agatggtgtg gaattgatgg aagccaaatc acagttattt cttaaatact tcacattatt    3540
tatgaacctt ttgaatgact gcagtgaagt tgaagatgaa agtgcgcaaa caggtggcag    3600
gaaacgtggc atgtctcgga ggctggcatc actgaggcac tgtacggtcc ttgcaatgtc    3660
aaacttactc aatgccaacg tagacagtgg tctcatgcac tccataggct taggttacca    3720
caaggatctc cagacaagag ctacatttat ggaagttctg acaaaaatcc ttcaacaagg    3780
cacagaattt gacacacttg cagaaacagt attggctgat cggtttgaga gattggtgga    3840
actggtcaca atgatgggtg atcaaggaga actccctata gcgatggctc tggccaatgt    3900
ggttccttgt tctcagtggg atgaactagc tcgagttctg gttactctgt ttgattctcg    3960
gcatttactc taccaactgc tctggaacat gttttctaaa gaagtagaat tggcagactc    4020
catgcagact ctcttccgag gcaacagctt ggccagtaaa ataatgacat tctgtttcaa    4080
ggtatatggt gctacctatc tacaaaaact cctggatcct ttattacgaa ttgtgatcac    4140
atcctctgat tggcaacatg ttagctttga agtggatcct accaggttag aaccatcaga    4200
gagccttgag gaaaaccagc ggaacctcct tcagatgact gaaaagttct tccatgccat    4260
catcagttcc tcctcagaat tccccccctca acttcgaagt gtgtgccact gtttatacca    4320
ggtggttagc cagcgtttcc ctcagaacag catcggtgca gtaggaagtg ccatgttcct    4380
```

```
cagatttatc aatcctgcca ttgtctcacc gtatgaagca gggattttag ataaaaagcc    4440
accacctaga atcgaaaggg gcttgaagtt aatgtcaaag atacttcaga gtattgccaa    4500
tcatgttctc ttcacaaaag aagaacatat gcggcctttc aatgattttg tgaaaagcaa    4560
ctttgatgca gcacgcaggt ttttccttga tatagcatct gattgtccta caagtgatgc    4620
agtaaatcat agtctttcct tcataagtga cggcaatgtg cttgctttac atcgtctact    4680
ctggaacaat caggagaaaa ttgggcagta tctttccagc aacagggatc ataaagctgt    4740
tggaagacga cctttgata agatggcaac acttcttgca tacctgggtc ctccagagca    4800
caaacctgtg gcagatacac actggtccag ccttaacctt accagttcaa gtttgagga    4860
atttatgact aggcatcagg tacatgaaaa agaagaattc aaggctttga aaacgttaag    4920
tattttctac caagctggga cttccaaagc tgggaatcct attttttatt atgttgcacg    4980
gaggttcaaa actggtcaaa tcaatggtga tttgctgata taccatgtct tactgacttt    5040
aaagccatat tatgcaaagc catatgaaat tgtagtggac cttacccata ccgggcctag    5100
caatcgcttt aaaacagact ttctctctaa gtggtttgtt gttttttcctg gctttgctta    5160
cgacaacgtc tccgcagtct atatctataa ctgtaactcc tgggtcaggg agtacaccaa    5220
gtatcatgag cggctgctga ctggcctcaa aggtagcaaa aggcttgttt tcatagactg    5280
tcctgggaaa ctggctgagc acatagagca tgaacaacag aaactacctg ctgccacctt    5340
ggctttagaa gaggacctga aggtattcca caatgctctc aagctagctc acaaagacac    5400
caaagttttct attaaagttg gttcactgc tgtccaagta acttcagcag agcgaacaaa    5460
agtcctaggg caatcagtct ttctaaatga catttattat gcttcggaaa ttgaagaaat    5520
ctgcctagta gatgagaacc agttcacctt aaccattgca aaccagggca cgccgctcac    5580
cttcatgcac caggagtgtg aagccattgt ccagtctatc attcatatcc ggacccgctg    5640
ggaactgtca cagcccgact ctatccccca acacaccaag attcggccaa agatgtccc    5700
tgggacactg ctcaatatcg cattacttaa tttaggcagt tctgacccga gtttacggtc    5760
agctgcctat aatcttctgt gtgccttaac ttgtaccttt aatttaaaaa tcgagggcca    5820
gttactagag acatcaggtt tatgtatccc tgccaacaac accctctta ttgtctctat    5880
tagtaagaca ctggcagcca atgagccaca cctcacgtta gaattttttgg aagagtgtat    5940
ttctggattt agcaaatcta gtattgaatt gaaacacctt tgtttggaat acatgactcc    6000
atggctgtca aatctagttc gttttttgcaa gcataatgat gatgccaaac gacaaagagt    6060
tactgctatt cttgacaagc tgataacaat gaccatcaat gaaaaacaga tgtacccatc    6120
tattcaagca aaaatatggg gaagccttgg gcagattaca gatctgcttg atgttgtact    6180
agacagtttc atcaaaacca gtgcaacagg tggcttggga tcaataaaag ctgaggtgat    6240
ggcagatact gctgtagctt tggcttctgg aaatgtgaaa ttggtttcaa gcaaggttat    6300
tggaaggatg tgcaaaataa ttgacaagac atgcttatct ccaactccta ctttagaaca    6360
acatcttatg tgggatgata ttgctatttt agcacgctac atgctgatgc tgtccttcaa    6420
caattccctt gatgtggcag ctcatcttcc ctacctcttc cacgttgtta ctttcttagt    6480
agccacaggt ccgctctccc ttagagcttc cacacatgga ctggtcatta atatcattca    6540
ctctctgtgt acttgttcac agcttcattt tagtgaagag accaagcaag ttttgagact    6600
cagtctgaca gagttctcat acccaaatt ttacttgctg tttggcatta gcaaagtcaa    6660
gtcagctgct gtcattgcct tccgttccag ttaccgggac aggtcattct ctcctggctc    6720
```

```
ctatgagaga gagactttg cttttgacatc cttggaaaca gtcacagaag ctttgttgga    6780
gatcatggag gcatgcatga gagatattcc aacgtgcaag tggctggacc agtggacaga    6840
actagctcaa agatttgcat tccaatataa tccatccctg caaccaagag ctcttgttgt    6900
ctttgggtgt attagcaaac gagtgtctca tgggcagata agcagataa tccgtattct     6960
tagcaaggca cttgagagtt gcttaaaagg acctgacact tacaacagtc aagttctgat    7020
agaagctaca gtaatagcac taaccaaatt acagccactt cttaataagg actcgcctct    7080
gcacaaagcc ctcttttggg tagctgtggc tgtgctgcag cttgatgagg tcaacttgta    7140
ttcagcaggt accgcacttc ttgaacaaaa cctgcatact ttagatagtc tccgtatatt    7200
caatgacaag agtccagagg aagtatttat ggcaatccgg aatcctctgg agtggcactg    7260
caagcaaatg gatcattttg ttggactcaa tttcaactct aactttaact ttgcattggt    7320
tggacacctt ttaaaagggt acaggcatcc ttcacctgct attgttgcaa gaacagtcag    7380
aattttacat acactactaa ctctggttaa caaacacaga aattgtgaca aatttgaagt    7440
gaatacacag agcgtggcct acttagcagc tttacttaca gtgtctgaag aagttcgaag    7500
tcgctgcagc ctaaaacata gaaagtcact tcttcttact gatatttcaa tggaaaatgt    7560
tcctatggat acatatccca ttcatcatgg tgacccttcc tataggacac taaaggagac    7620
tcagccatgg tcctctccca aaggttctga aggatacctt gcagccacct atccaactgt    7680
cggccagacc agtccccgag ccaggaaatc catgagcctg acatggggc aaccttctca     7740
ggccaacact aagaagttgc ttggaacaag gaaaagtttt gatcacttga tatcagacac    7800
aaaggctcct aaaaggcaag aaatggaatc agggatcaca acaccccca aaatgaggag    7860
agtagcagaa actgattatg aaatggaaac tcagaggatt tcctcatcac aacagcaccc    7920
acatttacgt aaagtttcag tgtctgaatc aaatgttctc ttggatgaag aagtacttac    7980
tgatccgaag atccaggcgc tgcttcttac tgttctagct acactggtaa aatataccac    8040
agatgagttt gatcaacgaa ttctttatga atacttagca gaggccagtg ttgtgtttcc    8100
caaagtcttt cctgttgtgc ataatttgtt ggactctaag atcaacaccc tgttatcatt    8160
gtgccaagat ccaaatttgt taaatccaat ccatggaatt gtgcagagtg tggtgtacca    8220
tgaagaatcc ccaccacaat accaaacatc ttacctgcaa agttttggtt ttaatggctt    8280
gtggcggttt gcaggaccgt tttcaaagca aacacaaatt ccagactatg ctgagcttat    8340
tgttaagttt cttgatgcct tgattgacac gtacctgcct ggaattgatg aagaaaccag    8400
tgaagaatcc ctcctgactc ccacatctcc ttaccctcct gcactgcaga gccagcttag    8460
tatcactgcc aaccttaacc tttctaattc catgacctca cttgcaactt cccagcattc    8520
cccaggaatc gacaaggaga acgttgaact ctcccctacc actggccact gtaacagtgg    8580
acgaactcgc cacggatccg caagccaagt gcagaagcaa agaagcgctg gcagtttcaa    8640
acgtaatagc attaagaaga tcgtgtgaag cttgcttgct ttcttttta aaatcaactt     8700
aacatgggct cttcactagt gaccccttcc ctgtccttgc cctttccccc catgttgtaa    8760
tgctgcactt cctgttttat aatgaaccca tccggtttgc catgttgcca gatgatcaac    8820
tcttcgaagc cttgcctaaa tttaatgctg ccttttcttt aacttttttt cttctacttt    8880
tggcgtgtat ctggtatatg taagtgttca gaacaactgc aaagaaagtg ggaggtcagg    8940
aaacttttaa ctgagaaat                                                 8959
```

<210> SEQ ID NO 41
<211> LENGTH: 2257

<212> TYPE: DNA
<213> ORGANISM: Homo sapiens

<400> SEQUENCE: 41

```
acggcagccg tcagggaccg tcccccaact cccctttccg ctcaggcagg gtcctcgcgg         60
cccatgctgg ccgctgggga cccgcgcagc ccagaccgtt cccgggccgg ccagccggca        120
ccatggtggc cctgaggcct gtgcagcaac tccagggggg ctaaagggct cagagtgcag        180
gccgtggggc gcgagggtcc cgggcctgag ccccgcgcca tggccggggc catcgcttcc        240
cgcatgagct tcagctctct caagaggaag caacccaaga cgttcaccgt gaggatcgtc        300
accatggacg ccgagatgga gttcaattgc gagatgaagt ggaaagggaa ggacctcttt        360
gatttggtgt gccggactct ggggctccga gaaacctggt tctttggact gcagtacaca        420
atcaaggaca cagtggcctg gctcaaaatg gacaagaagg tactggatca tgatgtttca        480
aaggaagaac cagtcacctt tcacttcttg gccaaatttt atcctgagaa tgctgaagag        540
gagctggttc aggagatcac acaacattta ttcttcttac aggtaaagaa gcagatttta        600
gatgaaaaga tctactgccc tcctgaggct tctgtgctcc tggcttctta cgccgtccag        660
gccaagtatg gtgactacga ccccagtgtt cacaagcggg attttttggc ccaagaggaa        720
ttgcttccaa aagggtaat aaatctgtat cagatgactc cggaaatgtg ggaggagaga         780
attactgctt ggtacgcaga gcaccgaggc cgagccaggg atgaagctga atggaatat        840
ctgaagatag ctcaggacct ggagatgtac ggtgtgaact actttgcaat ccggaataaa        900
aagggcacag agctgctgct tggagtggat gccctgggc ttcacattta tgaccctgag         960
aacagactga cccccaagat ctccttcccg tggaatgaaa tccgaaacat ctcgtacagt       1020
gacaaggagt ttactattaa accactggat aagaaaattg atgtcttcaa gtttaactcc       1080
tcaaagcttc gtgttaataa gctgattctc cagctatgta tcgggaacca tgatctattt       1140
atgaggagaa ggaaagccga ttctttggaa gttcagcaga tgaaagccca ggccagggag       1200
gagaaggcta gaaagcagat ggagcggcag cgcctcgctc gagagaagca gatgagggag       1260
gaggctgaac gcacgaggga tgagttggag aggaggctgc tgcagatgaa agaagaagca       1320
acaatggcca acgaagcact gatgcggtct gaggagacag ctgacctgtt ggctgaaaag       1380
gcccagatca ccgaggagga ggcaaaactt ctggcccaga aggccgcaga ggctgagcag       1440
gaaatgcagc gcatcaaggc cacagcgatt cgcacggagg aggagaagcg cctgatggag       1500
cagaaggtgc tggaagccga ggtgctggca ctgaagatgg ctgaggagtc agagaggagg       1560
gccaaagagg cagatcagct gaagcaggac ctgcaggaag cacgcgaggc ggagcgaaga       1620
gccaagcaga agctcctgga gattgccacc aagcccacgt accgcccat gaacccaatt        1680
ccagcaccgt tgcctcctga catgccaagc ttcaacctca ttggtgacag cctgtctttc       1740
gacttcaaag atactgacat gaagcggctt tccatggaga tagagaaaga aaaagtggaa       1800
tacatggaaa agagcaagca tctgcaggag cagctcaatg aactcaagac agaaatcgag       1860
gccttgaaac tgaaagagag ggagacagct ctggatattc tgcacaatga aactccgac        1920
agggggtggca gcagcaagca caataccatt aaaaagctca ccttgcagag cgccaagtcc       1980
cgagtggcct tctttgaaga gctctagcag gtgacccagc cacccaggaa cctgccactt       2040
ctcctgctac cgggaccgcg ggatggacca gatatcaaga gagccatcca tagggagctg       2100
gctgggggtt tccgtgggag ctccagaact ttccccagct gagtgaagag cccagccct         2160
cttatgtgca attgccttga actacgaccc tgtagagatt tctctcatgg cgttctagtt       2220
```

```
ctctgacctg agtctttgtt ttaagaagta tttgtct                             2257
```

<210> SEQ ID NO 42
<211> LENGTH: 2969
<212> TYPE: DNA
<213> ORGANISM: Homo sapiens

<400> SEQUENCE: 42

```
ccaggcagct ggggtaagga gttcaaggca gcgcccacac ccgggggctc tccgcaaccc      60
gaccgcctgt ccgctccccc acttcccgcc ctccctccca cctactcatt cacccaccca     120
cccacccaga gccgggacgg cagcccaggc gccggcccc cgccgtctcc tcgccgcgat      180
cctggacttc ctcttgctgc aggacccggc ttccacgtgt gtcccggagc cggcgtctca     240
gcacacgctc cgctccgggc ctgggtgcct acagcagcca gagcagcagg gagtccggga     300
cccgggcggc atctgggcca gttaggcgc cgccgaggcc agcgctgaac gtctccaggg      360
ccggaggagc cgcggggcgt ccgggtctga gccgcagcaa atgggctccg acgtgcggga     420
cctgaacgcg ctgctgcccg ccgtcccctc cctgggtggc ggcggcggct gtgccctgcc     480
tgtgagcggc gcggcgcagt gggcgccggt gctggacttt gcgcccccgg gcgcttcggc     540
ttacgggtcg ttgggcggcc ccgcgccgcc accggctccg ccgccacccc cgccgccgcc     600
gcctcactcc ttcatcaaac aggagccgag ctggggcggc gcggagccgc acgaggagca     660
gtgcctgagc gccttcactg tccacttttc cggccagttc actggcacag ccggagcctg     720
tcgctacggg cccttcggtc ctcctccgcc cagccaggcg tcatccggcc aggccaggat     780
gtttcctaac gcgccctacc tgcccagctg cctcgagagc cagcccgcta ttcgcaatca     840
gggttacagc acggtcacct tcgacgggac gcccagctac ggtcacacgc cctcgcacca     900
tgcggcgcag ttccccaacc actcattcaa gcatgaggat cccatgggcc agcagggctc     960
gctgggtgag cagcagtact cggtgccgcc cccggtctat ggctgccaca cccccaccga    1020
cagctgcacc ggcagccagg cttttgctgct gaggacgccc tacagcagtg acaatttata    1080
ccaaatgaca tcccagcttg aatgcatgac ctggaatcag atgaacttag gagccacctt    1140
aaagggccac agcacagggt acgagagcga taaccacaca acgcccatcc tctgcggagc    1200
ccaatacaga atacacacgc acggtgtctt cagaggcatt caggatgtgc gacgtgtgcc    1260
tggagtagcc ccgactcttg tacggtcggc atctgagacc agtgagaaac gcccccttcat   1320
gtgtgcttac ccaggctgca ataagagata ttttaagctg tcccacttac agatgcacag    1380
caggaagcac actggtgaga aaccatacca gtgtgacttc aaggactgtg aacgaaggtt    1440
ttctcgttca gaccagctca aaagacacca aaggagacat acaggtgtga accattcca    1500
gtgtaaaact tgtcagcgaa agttctcccg gtccgaccac ctgaagaccc acaccaggac   1560
tcatacaggt gaaaagccct tcagctgtcg gtggccaagt tgtcagaaaa agtttgcccg    1620
gtcagatgaa ttagtccgcc atcacaacat gcatcagaga acatgacca aactccagct     1680
ggcgctttga ggggtctccc tcggggaccg ttcagtgtcc caggcagcac agtgtgtgaa    1740
ctgctttcaa gtctgactct ccactcctcc tcactaaaaa ggaaacttca gttgatcttc   1800
ttcatccaac ttccaagaca agataccggt gcttctggaa actaccaggt gtgcctggaa    1860
gagttggtct ctgccctgcc tacttttagt tgactcacag gccctggaga agcagctaac    1920
aatgtctggt tagttaaaag cccattgcca tttggtgtgg attttctact gtaagaagag    1980
ccatagctga tcatgtcccc ctgacccttc ccttcttttt ttatgctcgt tttcgctggg    2040
gatggaatta ttgtaccatt ttctatcatg gaatatttat aggccagggc atgtgtatgt    2100
```

-continued

```
gtctgctaat gtaaactttg tcatggtttc catttactaa cagcaacagc aagaaataaa    2160
tcagagagca aggcatcggg ggtgaatctt gtctaacatt cccgaggtca gccaggctgc    2220
taacctggaa agcaggatgt agttctgcca ggcaacttt aaagctcatg catttcaagc    2280
agctgaagaa aaaatcagaa ctaaccagta cctctgtata gaaatctaaa agaattttac    2340
cattcagtta attcaatgtg aacactggca cactgctctt aagaaactat gaagatctga    2400
gatttttttg tgtatgtttt tgactctttt gagtggtaat catatgtgtc tttatagatg    2460 tacataccte cttgcacaaa tggaggggaa ttcatttca tcactgggag tgtccttagt    2520
gtataaaaac catgctggta tatggcttca agttgtaaaa atgaaagtga ctttaaaaga    2580
aaatagggga tggtccagga tctccactga taagactgtt tttaagtaac ttaaggacct    2640
ttgggtctac aagtatatgt gaaaaaaatg agacttactg ggtgaggaaa tccattgttt    2700
aaagatggtc gtgtgtgtgt gtgtgtgtgt gtgtgtgtgt gtgttgtgtt gtgttttgtt    2760
ttttaaggga gggaatttat tatttaccgt tgcttgaaat tactgtgtaa atatatgtct    2820
gataatgatt tgctctttga caactaaaat taggactgta taagtactag atgcatcact    2880
gggtgttgat cttacaagat attgatgata acacttaaaa ttgtaacctg cattttcac    2940 tttgctctca attaaagtct attcaaaag                                       2969
```

```
<210> SEQ ID NO 43
<211> LENGTH: 69
<212> TYPE: DNA
<213> ORGANISM: Artificial
<220> FEATURE:
<223> OTHER INFORMATION: synthetic DNA

<400> SEQUENCE: 43
ggcctccata aagtaggaaa cactacacag ctccataaag taggaaacac tacattaatt    60
aagcggtac                                                             69

<210> SEQ ID NO 44
<211> LENGTH: 61
<212> TYPE: DNA
<213> ORGANISM: Artificial
<220> FEATURE:
<223> OTHER INFORMATION: synthetic DNA

<400> SEQUENCE: 44
cgcttaatta atgtagtgtt tcctacttta tggagctgtg tagtgtttcc tactttatgg    60
a                                                                     61

<210> SEQ ID NO 45
<211> LENGTH: 54
<212> TYPE: DNA
<213> ORGANISM: Artificial
<220> FEATURE:
<223> OTHER INFORMATION: synthetic DNA

<400> SEQUENCE: 45
tccataaagt aggaaacact acaggactcc ataaagtagg aaacactaca gtac           54

<210> SEQ ID NO 46
<211> LENGTH: 52
<212> TYPE: DNA
<213> ORGANISM: Artificial
<220> FEATURE:
<223> OTHER INFORMATION: synthetic DNA
```

```
<400> SEQUENCE: 46
tgtagtgttt cctactttat ggagtcctgt agtgtttcct actttatgga at              52

<210> SEQ ID NO 47
<211> LENGTH: 573
<212> TYPE: DNA
<213> ORGANISM: Adenovirus

<400> SEQUENCE: 47
ttatggactg gaataaaccc tccacctaac tgtcaaattg tggaaaacac taatacaaat      60
gatggcaaac ttactttagt attagtaaaa aacggagggc ttgttaatgg ctacgtgtct    120
ctagttggtg tatcagacac tgtgaaccaa atgttcacac aaaagacagc aaacatccaa    180
ttaagattat attttgactc ttctggaaat ctattaactg atgaatcaga cttaaaaatt    240
ccacttaaaa ataaatcttc tacagcgacc agtgaaactg tagccagcag caaagccttt    300
atgccaagta ctacagctta tcccttcaac accactacta gggatagtga aaactacatt    360
catggaatat gttactacat gactagttat gatagaagtc tatttccctt gaacatttct    420
ataatgctaa acagccgtat gatttcttcc aatgttgcct atgccataca atttgaatgg    480
aatctaaatg caagtgaatc tccagaaagc aacatagcta cgctgaccac atcccccttt    540
ttcttttctt acattacaga agacgacaac taa                                  573

<210> SEQ ID NO 48
<211> LENGTH: 270
<212> TYPE: DNA
<213> ORGANISM: Adenovirus

<400> SEQUENCE: 48
ggagttctta ctcttaagtg tttaaccccca ctaacaacca caggcggatc tctacagcta     60
aaagtgggag ggggacttac agtggatgac actgatggta ccttacaaga aaacatacgt    120
gctacagcac ccattactaa aataatcac tctgtagaac tatccattgg aaatggatta     180
gaaactcaaa acaataaact atgtgccaaa ttgggaaatg ggttaaaatt taacaacggt    240
gacatttgta taaggatag tattaacacc                                       270

<210> SEQ ID NO 49
<211> LENGTH: 843
<212> TYPE: DNA
<213> ORGANISM: Adenovirus

<400> SEQUENCE: 49
ggagttctta ctcttaagtg tttaaccccca ctaacaacca caggcggatc tctacagcta     60
aaagtgggag ggggacttac agtggatgac actgatggta ccttacaaga aaacatacgt    120
gctacagcac ccattactaa aataatcac tctgtagaac tatccattgg aaatggatta     180
gaaactcaaa acaataaact atgtgccaaa ttgggaaatg ggttaaaatt taacaacggt    240
gacatttgta taaggatag tattaacacc ttatggactg gaataaaccc tccacctaac     300
tgtcaaattg tggaaaacac taatacaaat gatggcaaac ttactttagt attagtaaaa    360
aacggagggc ttgttaatgg ctacgtgtct ctagttggtg tatcagacac tgtgaaccaa    420
atgttcacac aaaagacagc aaacatccaa ttaagattat attttgactc ttctggaaat    480
ctattaactg atgaatcaga cttaaaaatt ccacttaaaa ataaatcttc tacagcgacc    540
agtgaaactg tagccagcag caaagccttt atgccaagta ctacagctta tcccttcaac    600
accactacta gggatagtga aaactacatt catggaatat gttactacat gactagttat    660
```

```
gatagaagtc tatttccctt gaacatttct ataatgctaa acagccgtat gatttcttcc      720
aatgttgcct atgccataca atttgaatgg aatctaaatg caagtgaatc tccagaaagc      780
aacatagcta cgctgaccac atcccccttt ttcttttctt acattacaga agacgacaac      840
taa                                                                   843
```

<210> SEQ ID NO 50
<211> LENGTH: 975
<212> TYPE: DNA
<213> ORGANISM: Artificial
<220> FEATURE:
<223> OTHER INFORMATION: synthetic DNA

<400> SEQUENCE: 50

```
atgaagcgcg caagaccgtc tgaagatacc ttcaaccccg tgtatccata tgacacggaa       60
accggtcctc caactgtgcc ttttcttact cctccctttg tatcccccaa tgggtttcaa      120
gagagtcccc ctggagttct tactcttaag tgtttaaccc cactaacaac cacaggcgga      180
tctctacagc taaagtggg aggggacttc acagtggatg acactgatgg taccttacaa      240
gaaaacatac gtgctacagc acccattact aaaaataatc actctgtaga actatccatt      300
ggaaatggat tagaaactca aaacaataaa ctatgtgcca aattgggaaa tgggttaaaa      360
tttaacaacg gtgacatttg tataaaggat agtattaaca ccttatggac tggaataaac      420
cctccaccta actgtcaaat tgtggaaaac actaatacaa atgatggcaa acttacttta      480
gtattagtaa aaaacggagg gcttgttaat ggctacgtgt ctctagttgg tgtatcagac      540
actgtgaacc aaatgttcac acaaagaca gcaaacatcc aattaagatt atattttgac      600
tcttctggaa atctattaac tgatgaatca gacttaaaaa ttccacttaa aaataaatct      660
tctacagcga ccagtgaaac tgtagccagc agcaaagcct ttatgccaag tactacagct      720
tatcccttca acaccactac tagggatagt gaaaactaca ttcatggaat atgttactac      780
atgactagtt atgatagaag tctatttccc ttgaacattt ctataatgct aaacagccgt      840
atgatttctt ccaatgttgc ctatgccata caatttgaat ggaatctaaa tgcaagtgaa      900
tctccagaaa gcaacatagc tacgctgacc acatccccct ttttcttttc ttacattaca      960
gaagacgaca actaa                                                       975
```

<210> SEQ ID NO 51
<211> LENGTH: 35324
<212> TYPE: DNA
<213> ORGANISM: Artificial Sequence
<220> FEATURE:
<223> OTHER INFORMATION: synthetic DNA

<400> SEQUENCE: 51

```
tatattattg atgatgcctt attttggatt gaagccaata tgataatgag ggggtggagt       60
ttgtgacgtg gcgcggggcg tgggaacggg gcgggtgacg tagtagtgtg gcggaagtgt      120
gatgttgcaa gtgtggcgga acacatgtaa gcgacggatg tggcaaaagt gacgtttttg      180
gtgtgcgccg gtgtacacag gaagtgacaa ttttcgcgcg gttttaggcg gatgttgtag      240
taaatttggg cgtaaccgag taagatttgg ccattttcgc gggaaaactg aataagagga      300
agtgaaatct gaataatttt gtgttactca tagcgcgtaa tctctagcat cgtaactata      360
acggtcctaa ggtagcgaaa gctcagatct cccgatcccc tatggtgcac tctcagtaca      420
atctgctctg atgccgcata gttaagccag tatctgctcc ctgcttgtgt gttggaggtc      480
```

```
gctgagtagt gcgcgagcaa aatttaagct acaacaaggc aaggcttgac cgacaattct    540
agcctcgacg cgttggcccc tccctcgggt taccccacag cctaggccga ttcgacctct    600
ctccgctggg gccctcgctg gcgtccctgc accctgggag cgcgagcggc gcgcgggcgg    660
ggaagcgcgg cccagacccc cgggtccgcc cggagcagct cgcgctgtcg ggccaggccg    720
ggctcccagt ggattcgcgg gcacagacgc ccaggaccgc gctcccacg tggcggaggg     780
actggggacc cggcacccg tcctgcccct tcaccttcca gctccgcctc ctccgcgcgg     840
accccgcccc gtcccgaccc ctcccgggtc cccggcccag cccctccgg gccctcccag     900
cccctcccct tccttccgc ggccccgccc tctcctcgcg gcgcgagttt caggcagcgc     960
tgcgtcctgc tgcgcacgtg ggaagccctg gccccggcca ccccgcgat agatctcgag    1020
aattcacgcg aattcggctt acaccgggac tgaaaatgag acatattatc tgccacggag    1080
gtgttattac cgaagaaatg gccgccagtc ttttggacca gctgatcgaa gaggtactgg    1140
ctgataatct tccacctcct agccattttg aaccacctac ccttcacgaa ctgtatgatt    1200
tagacgtgac ggcccccgaa gatcccaacg aggaggcggt ttcgcagatt tttcccgact    1260
ctgtaatgtt ggcggtgcag gaagggattg acttactcac ttttccgccg gcgcccggtt    1320
ctccggagcc gcctcacctt tcccggcagc ccgagcagcc ggagcagaga gccttgggtc    1380
cggtttctat gccaaacctt gtaccggagg tgatcgatct tacctgccac gaggctggct    1440
ttccacccag tgacgacgag gatgaagagg gtgaggagt tgtgttagat tatgtggagc    1500
accccgggca cggttgcagg tcttgtcatt atcaccggag gaatacgggg gacccagata    1560
ttatgtgttc gctttgctat atgaggacct gtggcatgtt tgtctacagt cctgtgtctg    1620
aacctgagcc tgagcccgag ccagaaccgg agcctgcaag acctacccgc cgtcctaaaa    1680
tggcgcctgc tatcctgaga cgcccgacat cacctgtgtc tagagaatgc aatagtagta    1740
cggatagctg tgactccggt ccttctaaca cacctcctga gatacacccg gtggtcccgc    1800
tgtgccccat taaaccagtt gccgtgagag ttggtgggcg tcgccaggct gtggaatgta    1860
tcgaggactt gcttaacgag cctgggcaac ctttggactt gagctgtaaa cgccccaggc    1920
cataaggtgt aaacctgtga agccgaattc gcgtcgagca tgcatctagg gcggccaatt    1980
ccgcccctct cccccccccc cctctccctc cccccccccc taacgttact ggccgaagcc    2040
gcttggaata aggccggtgt gcgtttgtct atatgttatt ttccaccata ttgccgtctt    2100
ttggcaatgt gagggcccgg aaacctggcc ctgtcttctt gacgagcatt cctaggggtc    2160
tttcccctct cgccaaagga atgcaaggtc tgttgaatgt cgtgaaggaa gcagttcctc    2220
tggaagcttc ttgaagacaa acaacgtctg tagcgaccct ttgcaggcag cggaaccccc    2280
cacctggcga caggtgcctc tgcggccaaa agccacgtgt ataagataca cctgcaaagg    2340
cggcacaacc ccagtgccac gttgtgagtt ggatagttgt ggaaagagtc aaatggctct    2400
cctcaagcgt attcaacaag gggctgaagg atgcccagaa ggtaccccat tgtatgggat    2460
ctgatctggg gcctcggtgc acatgcttta catgtgttta gtcgaggtta aaaaaacgtc    2520
taggcccccc gaaccacggg gacgtggttt tcctttgaaa aacacgatga taagcttgcc    2580
acaacccggg atcctctaga gtcgaaattc ggcttctgac ctcatggagg cttgggagtg    2640
tttggaagat ttttctgctg tgcgtaactt gctggaacag agctctaaca gtacctcttg    2700
gttttggagg tttctgtggg gctcatccca ggcaaagtta gtctgcagaa ttaaggagga    2760
ttacaagtgg gaatttgaag agcttttgaa atcctgtggt gagctgtttg attctttgaa    2820
tctgggtcac caggcgcttt tccaagagaa ggtcatcaag actttggatt tttccacacc    2880
```

```
ggggcgcgct gcggctgctg ttgctttttt gagttttata aaggataaat ggagcgaaga    2940
aacccatctg agcgggggt acctgctgga ttttctggcc atgcatctgt ggagagcggt     3000
tgtgagacac aagaatcgcc tgctactgtt gtcttccgtc cgcccggcga taataccgac    3060
ggaggagcag cagcagcagc aggaggaagc caggcggcgg cggcaggagc agagcccatg    3120
gaacccgaga gccggcctgg accctcggga atgaatgttg tacaggtggc tgaactgtat    3180
ccagaactga gacgcatttt gacaattaca gaggatgggc aggggctaaa gggggtaaag    3240
agggagcggg gggcttgtga ggctacagag gaggctagga atctagcttt tagcttaatg    3300
accagacacc gtcctgagtg tattactttt caacagatca aggataattg cgctaatgag    3360
cttgatctgc tggcgcagaa gtattccata gagcagctga ccacttactg gctgcagcca    3420
ggggatgatt ttgaggaggc tattagggta tatgcaaagg tggcacttag ccagattgc     3480 aagtacaaga tcagcaaact tgtaaatatc aggaattgtt gctacatctc tgggaacggg    3540
gccgaggtgg agatagatac ggaggatagg gtggccttta gatgtagcat gataaatatg    3600
tggccggggg tgcttggcat ggacggggtg gttattatga atgtaaggtt tactggcccc    3660
aattttagcg gtacggtttt cctggccaat accaaccttta tcctacacgg tgtaagcttc   3720
tatgggttta caataccctg tgtggaagcc tggaccgatg taagggttcg gggctgtgcc    3780
ttttactgct gctggaaggg ggtggtgtgt cgccccaaaa gcagggcttc aattaagaaa    3840
tgcctctttg aaaggtgtac cttgggtatc ctgtctgagg gtaactccag ggtgcgccac    3900
aatgtggcct ccgactgtgg ttgcttcatg ctagtgaaaa gcgtggctgt gattaagcat    3960
aacatggtat gtggcaactg cgaggacagg gcctctcaga tgctgacctg ctcggacggc    4020
aactgtcacc tgctgaagac cattcacgta gccagccact ctcgcaaggc ctggccagtg    4080
tttgagcata acatactgac ccgctgttcc ttgcatttgg gtaacaggag gggggtgttc    4140
ctaccttacc aatgcaatttt gagtcacact aagatattgc ttgagcccga gagcatgtcc    4200
aaggtgaacc tgaacggggt gttgacatg accatgaaga tctggaaggt gctgaggtac     4260
gatgagaccc gcaccaggtg cagaccctgc gagtgtggcg gtaaacatat taggaaccag    4320
cctgtgatgc tggatgtgac cgaggagctg aggcccgatc acttggtgct ggcctgcacc    4380
cgcgctgagt ttggctctag cgatgaagat acagattgag gtactgaaat atgtgggcaa    4440
gccgaatttc gacccgggcg gcctagcgtt tctagcgttt aaacgggccc tctagactcg    4500
agcggcctcc ataaagtagg aaacactaca cagctcccata agtaggaaa cactacatta    4560 attccataaa gtaggaaaca ctacaggact ccataaagta ggaaacacta cagtaccaag    4620
cttaagttta aaccgctgat tagcctcgac tgtgccttct agttgccagc catctgttgt    4680 ttgccctcc cccgtgcctt ccttgaccct ggaaggtgcc actcccactg tcctttccta     4740
ataaaatgag gaaattgcat cgcattgtct gagtaggtgt cattctattc tggggggtgg    4800
ggtggggcag gacagcaagg gggaggattg gaagacaat gcaggcatg ctggggatgc      4860 ggtgggctct atggcttctg aggcggaaag aaccagcaga tctgcagatc tgaattcatc    4920
tatgtcgggt gcggagaaag aggtaatgaa atggcatcga ctcgaagatc tgggcgtggt    4980
taagggtggg aaagaatata aaggtgggg gtcttatgta gttttgtatc tgttttgcag    5040
cagccgccgc cgccatgagc accaactcgt ttgatggaag cattgtgagc tcatatttga    5100
caacgcgcat gcccccatgg gccggggtgc gtcagaatgt gatgggctcc agcattgatg    5160
gtcgccccgt cctgccgca aactctacta ccttgaccta cgagaccgtg tctggaacgc     5220
```

```
cgttggagac tgcagcctcc gccgccgctt cagccgctgc agccaccgcc cgcgggattg    5280
tgactgactt tgcttcctg agcccgcttg caagcagtgc agcttccgt tcatccgccc      5340 gcgatgacaa gttgacggct cttttggcac aattggattc tttgacccgg gaacttaatg   5400
tcgtttctca gcagctgttg gatctgcgcc agcaggtttc tgccctgaag gcttcctccc   5460
ctcccaatgc ggtttaaaac ataaataaaa aaccagactc tgtttggatt tggatcaagc   5520
aagtgtcttg ctgtctttat ttaggggttt tgcgcgcgcg gtaggcccgg gaccagcggt   5580
ctcggtcgtt gagggtcctg tgtattttt ccaggacgtg gtaaaggtga ctctggatgt    5640
tcagatacat gggcataagc ccgtctctgg ggtggaggta gcaccactgc agagcttcat   5700 gctgcgggt ggtgttgtag atgatccagt cgtagcagga gcgctgggcg tggtgcctaa    5760
aaatgtcttt cagtagcaag ctgattgcca ggggcaggcc cttggtgtaa gtgtttacaa   5820
agcggttaag ctgggatggg tgcatacgtg gggatatgag atgcatcttg gactgtattt   5880
ttaggttggc tatgttccca gccatatccc tccggggatt catgttgtgc agaaccacca   5940
gcacagtgta tccggtgcac ttgggaaatt tgtcatgtag cttagaagga aatgcgtgga   6000
agaacttgga gacgcccttg tgacctccaa gattttccat gcattcgtcc ataatgatgg   6060
caatgggccc acgggcggcg gcctgggcga agatatttct gggatcacta acgtcatagt   6120
tgtgttccag gatgagatcg tcataggcca tttttacaaa gcgcgggcgg agggtgccag   6180
actgcggtat aatggttcca tccggcccag gggcgtagtt accctcacag atttgcattt   6240
cccacgcttt gagttcagat gggggatca tgtctacctg cggggcgatg aagaaaacgg    6300
tttccggggt aggggagatc agctgggaag aaagcaggtt cctgagcagc tgcgacttac   6360
cgcagccggt gggcccgtaa atcacaccta ttaccggctg caactggtag ttaagagagc   6420
tgcagctgcc gtcatccctg agcaggggg ccacttcgtt aagcatgtcc ctgactcgca    6480
tgttttccct gaccaaatcc gccagaaggc gctcgccgcc cagcgatagc agttcttgca   6540
aggaagcaaa gttttcaac ggtttgagac cgtccgccgt aggcatgctt ttgagcgttt    6600
gaccaagcag ttccaggcgg tcccacagct cggtcacctg ctctacggca tctcgatcca   6660
gcatatctcc tcgtttcgcg ggttggggcg gctttcgctg tacggcagta gtcggtgctc   6720
gtccagacgg gccagggtca tgtctttcca cgggcgcagg gtcctcgtca gcgtagtctg   6780
ggtcacggtg aagggtgcg ctccgggctg cgcgctggcc agggtgcgct tgaggctggt    6840
cctgctggtg ctgaagcgct gccggtcttc gccctgcgcg tcggccaggt agcatttgac   6900
catggtgtca tagtccagcc cctccgcggc gtggcccttg gcgcgcagct tgcccttgga   6960
ggaggcgccg cacgagggc agtgcagact tttgagggcg tagagcttgg gcgcgagaaa    7020
taccgattcc ggggagtagg catccgcgcc gcaggcccg cagacggtct cgcattccac    7080
gagccaggtg agctctggcc gttcgggtc aaaaccagg tttcccccat gcttttgat      7140 gcgtttctta cctctggttt ccatgagccg gtgtccacgc tcggtgacga aaaggctgtc   7200 cgtgtcccg tatacagact tgagaggcct gtcctcgagc ggtgttccgc ggtcctcctc    7260
gtatagaaac tcggaccact ctgagacaaa ggctcgcgtc caggccagca cgaaggaggc   7320
taagtgggag gggtagcgt cgttgtccac taggggtcc actcgctcca gggtgtgaag    7380
acacatgtcg ccctcttcgg catcaaggaa ggtgattggt ttgtaggtgt aggccacgtg   7440
accgggtgtt cctgaagggg gctataaaa ggggtgggg gcgcgttcgt cctcactctc     7500
ttccgcatcg ctgtctgcga gggccagctg ttggggtgag tactccctct gaaaagcggg   7560
catgacttct gcgctaagat tgtcagtttc caaaaacgag gaggatttga tattcacctg   7620
```

```
gcccgcggtg atgcctttga gggtggccgc atccatctgg tcagaaaaga caatcttttt    7680
gttgtcaagc ttggtggcaa acgacccgta gagggcgttg dacagcaact tggcgatgga    7740
gcgcagggtt tggttttttgt cgcgatcggc gcgctccttg ccgcgatgt ttagctgcac    7800 gtattcgcgc gcaacgcacc gccattcggg aaagacggtg gtgcgctcgt cgggcaccag    7860
gtgcacgcgc caaccgcggt tgtgcagggt gacaaggtca acgctggtgg ctacctctcc    7920
gcgtaggcgc tcgttggtcc agcagaggcg ccgcccttg cgcgagcaga atggcggtag    7980
ggggtctagc tgcgtctcgt ccggggggtc tgcgtccacg gtaaagaccc cgggcagcag    8040
gcgcgcgtcg aagtagtcta tcttgcatcc ttgcaagtct agcgcctgct gccatgcgcg    8100
ggcggcaagc gcgcgctcgt atgggttgag tgggggaccc catggcatgg ggtgggtgag    8160
cgcggaggcg tacatgccgc aaatgtcgta aacgtagagg ggctctctga gtattccaag    8220
atatgtaggg tagcatcttc caccgcggat gctggcgcgc acgtaatcgt atagttcgtg    8280
cgagggagcg aggaggtcgg gaccgaggtt gctacgggcg ggctgctctg ctcggaagac    8340
tatctgcctg aagatggcat gtgagttgga tgatatggtt ggacgctgga agacgttgaa    8400
gctggcgtct gtgagaccta ccgcgtcacg cacgaaggag gcgtaggagt cgcgcagctt    8460
gttgaccagc tcggcggtga cctgcacgtc tagggcgcag tagtccaggg tttccttgat    8520
gatgtcatac ttatcctgtc cctttttttt ccacagctcg cggttgagga caaactcttc    8580
gcggtctttc cagtactctt ggatcggaaa cccgtcggcc tccgaacggt aagagcctag    8640
catgtagaac tggttgacgg cctggtaggc gcagcatccc ttttctacgg gtagcgcgta    8700
tgcctgcgcg gccttccgga gcgaggtgtg ggtgagcgca aaggtgtccc tgaccatgac    8760
tttgaggtac tggtatttga agtcagtgtc gtcgcatccg ccctgctccc agagcaaaaa    8820
gtccgtgcgc tttttggaac gcggatttgg cagggcgaag gtgacatcgt tgaagagtat    8880
ctttcccgcg cgaggcataa agttgcgtgt gatgcggaag ggtcccggca cctcggaacg    8940
gttgttaatt acctgggcgg cgagcacgat ctcgtcaaag ccgttgatgt tgtggcccac    9000
aatgtaaagt tccaagaagc gcgggatgcc cttgatggaa ggcaattttt taagttcctc    9060
gtaggtgagc tcttcagggg agctgagccc gtgctctgaa agggcccagt ctgcaagatg    9120
agggttggaa gcgacgaatg agctccacag gtcacgggcc attagcattt gcaggtggtc    9180
gcgaaaggtc ctaaactggc gacctatggc cattttttct ggggtgatgc agtagaaggt    9240
aagcgggtct tgttcccagc ggtcccatcc aaggttcgcg gctaggtctc gcgcggcagt    9300
cactagaggc tcatctccgc cgaacttcat gaccagcatg aagggcacga gctgcttccc    9360
aaaggccccc atccaagtat aggtctctac atcgtaggtg acaaagagac gctcggtgcg    9420
aggatgcgag ccgatcggga agaactggat ctcccgccac caattggagg agtggctatt    9480
gatgtggtga agtagaagt ccctgcgacg ggccgaacac tcgtgctggc ttttgtaaaa    9540
acgtgcgcag tactggcagc ggtgcacggg ctgtacatcc tgcacgaggt tgacctgacg    9600
accgcgcaca aggaagcaga gtgggaattt gagcccctcg cctggcgggt ttggctggtg    9660
gtcttctact tcggctgctt gtccttgacc gtctggctgc tcgaggggag ttacggtgga    9720
tcggaccacc acgccgcgcg agcccaaagt ccagatgtcc gcgcgcggcg gtcggagctt    9780
gatgacaaca tcgcgcagat gggagctgtc catggtctgg agctccgcg gcgtcaggtc    9840 aggcgggagc tcctgcaggt ttacctcgca tagacgggtc agggcgcggg ctagatccag    9900
gtgataccta atttccaggg gctggttggt ggcggcgtcg atggcttgca agaggccgca    9960
```

-continued

```
tccccgcggc gcgactacgg taccgcgcgg cgggcggtgg gccgcggggg tgtccttgga    10020
tgatgcatct aaaagcggtg acgcgggcga gcccccggag gtaggggggg ctccggaccc    10080
gccgggagag ggggcagggg cacgtcggcg ccgcgcgcgg gcaggagctg gtgctgcgcg    10140
cgtaggttgc tggcgaacgc gacgacgcgg cggttgatct cctgaatctg gcgcctctgc    10200
gtgaagacga cgggcccggt gagcttgaac ctgaaagaga gttcgacaga atcaatttcg    10260
gtgtcgttga cggcggcctg gcgcaaaatc tcctgcacgt ctcctgagtt gtcttgatag    10320
gcgatctcgg ccatgaactg ctcgatctct tcctcctgga gatctccgcg tccggctcgc    10380
tccacggtgg cggcgaggtc gttggaaatg cgggccatga gctgcgagaa ggcgttgagg    10440
cctccctcgt tccagacgcg gctgtagacc acgcccccctt cggcatcgcg ggcgcgcatg    10500
accacctgcg cgagattgag ctccacgtgc cgggcgaaga cggcgtagtt cgcaggcgc    10560
tgaaagaggt agttgagggt ggtggcggtg tgttctgcca cgaagaagta cataacccag    10620
cgtcgcaacg tggattcgtt gatatccccc aaggcctcaa ggcgctccat ggcctcgtag    10680
aagtccacgg cgaagttgaa aaactgggag ttgcgcgccg acacggttaa ctcctcctcc    10740
agaagacgga tgagctcggc gacagtgtcg cgcacctcgc gctcaaaggc tacaggggcc    10800
tcttcttctt cttcaatctc ctcttccata agggcctccc cttcttcttc ttctggcggc    10860
ggtgggggag ggggacacg gcggcgacga cggcgcaccg ggaggcggtc gacaaagcgc    10920
tcgatcatct ccccgcggcg acggcgcatg gtctcggtga cggcgcggcc gttctcgcgg    10980
gggcgcagtt ggaagacgcc gcccgtcatg tcccggttat gggttggcgg ggggctgcca    11040
tgcggcaggg atacggcgct aacgatgcat ctcaacaatt gttgtgtagg tactccgccg    11100
ccgagggacc tgagcgagtc cgcatcgacc ggatcggaaa acctctcgag aaaggcgtct    11160
aaccagtcac agtcgcaagg taggctgagc accgtggcgg gcggcagcgg gcggcggtcg    11220
gggttgtttc tggcggaggt gctgctgatg atgtaattaa agtaggcggt cttgagacgg    11280
cggatggtcg acagaagcac catgtccttg ggtccggcct gctgaatgcg caggcggtcg    11340
gccatgcccc aggcttcgtt ttgacatcgg cgcaggtctt tgtagtagtc ttgcatgagc    11400
cttttctaccg gcacttcttc ttctcccttcc tcttgtcctg catctcttgc atctatcgct    11460
gcggcggcgg cggagtttgg ccgtaggtgg cgccctcttc ctcccatgcg tgtgaccccg    11520
aagcccctca tcggctgaag cagggctagg tcggcgacaa cgcgctcggc taatatggcc    11580
tgctgcacct gcgtgagggt agactggaag tcatccatgt ccacaaagcg gtggtatgcg    11640
cccgtgttga tggtgtaagt gcagttggcc ataacggacc agttaacggt ctggtgaccc    11700
ggctgcgaga gctcggtgta cctgagacgc gagtaagccc tcgagtcaaa tacgtagtcg    11760
ttgcaagtcc gcaccaggta ctggtatccc accaaaaagt gcggcggcgg ctggcggtag    11820
aggggccagc gtagggtggc cggggctccg ggggcgagat cttccaacat aaggcgatga    11880
tatccgtaga tgtacctgga catccaggta atgccggcgg cggtggtgga ggcgcgcgga    11940
aagtcgcgga cgcggttcca gatgttgcgc agcggcaaaa agtgctccat ggtcgggacg    12000
ctctggccgg tcaggcgcgc gcaatcgttg acgctctagc gtgcaaaagg agagcctgta    12060
agcgggcact cttccgtggt ctggtggata aattcgcaag ggtatcatgg cggacgaccg    12120
gggttcgagc cccgtatccg gccgtccgcc gtgatccatg cggttaccgc ccgcgtgtcg    12180
aacccaggtg tgcgacgtca gacaacgggg gagtgctcct tttggcttcc ttccaggcgc    12240
ggcggctgct gcgctagctt ttttggccac tggccgcgcg cagcgtaagc ggttaggctg    12300
gaaagcgaaa gcattaagtg gctcgctccc tgtagccgga gggttatttt ccaagggttg    12360
```

```
agtcgcggga cccccggttc gagtctcgga ccggccggac tgcggcgaac gggggtttgc   12420
ctccccgtca tgcaagaccc cgcttgcaaa ttcctccgga aacagggacg agccccttt    12480 ttgcttttcc cagatgcatc cggtgctgcg gcagatgcgc cccctcctc agcagcggca    12540 agagcaagag cagcggcaga catgcagggc accctcccct cctcctaccg cgtcaggagg   12600
ggcgacatcc gcggttgacg cggcagcaga tggtgattac gaaccccgc ggcgccgggc    12660 ccggcactac ctggacttgg aggagggcga gggcctggcg cggctaggag cgccctctcc   12720
tgagcggcac ccaagggtgc agctgaagcg tgatacgcgt gaggcgtacg tgccgcggca   12780
gaacctgttt cgcgaccgcg agggagagga gcccgaggag atgcgggatc gaaagttcca   12840
cgcagggcgc gagctgcggc atggcctgaa tcgcgagcgg ttgctgcgcg aggaggactt   12900
tgagcccgac gcgcgaaccg ggattagtcc cgcgcgcgca cacgtggcgg ccgccgacct   12960
ggtaaccgca tacgagcaga cggtgaacca ggagattaac tttcaaaaaa gctttaacaa   13020
ccacgtgcgt acgcttgtgg cgcgcgagga ggtggctata ggactgatgc atctgtggga   13080
ctttgtaagc gcgctggagc aaaacccaaa tagcaagccg ctcatggcgc agctgttcct   13140
tatagtgcag cacagcaggg acaacgaggc attcagggat gcgctgctaa acatagtaga   13200
gcccgagggc cgctggctgc tcgatttgat aaacatcctg cagagcatag tggtgcagga   13260
gcgcagcttg agcctggctg acaaggtggc cgccatcaac tattccatgc ttagcctggg   13320
caagttttac gcccgcaaga tataccatac cccttacgtt cccatagaca aggaggtaaa   13380
gatcgagggg ttctacatgc gcatggcgct gaaggtgctt accttgagcg acgacctggg   13440
cgtttatcgc aacgagcgca tccacaaggc cgtgagcgtg agccggcggc gcgagctcag   13500
cgaccgcgag ctgatgcaca gcctgcaaag ggccctggct ggcacgggca gcggcgatag   13560
agaggccgag tcctactttg acgcgggcgc tgacctgcgc tgggccccaa gccgacgcgc   13620
cctggaggca gctggggccg gacctggggct ggcggtggca cccgcgcgcg ctggcaacgt   13680
cggcggcgtg gaggaatatg acgaggacga tgagtacgag ccagaggacg gcgagtacta   13740
agcggtgatg tttctgatca gatgatgcaa gacgcaacgg acccggcggt gcgggcggcg   13800
ctgcagagcc agccgtccgg ccttaactcc acggacgact ggcgcaggt catgaccgc     13860 atcatgtcgc tgactgcgcg caatcctgac gcgttccggc agcagccgca ggccaaccgg   13920
ctctccgcaa ttctggaagc ggtggtcccg gcgcgcgcaa accccacgca cgagaaggtg   13980
ctggcgatcg taaacgcgct ggccgaaaac agggccatcc ggcccgacga ggccggcctg   14040
gtctacgacg cgctgcttca gcgcgtggct cgttacaaca gcggcaacgt gcagaccaac   14100
ctggaccggc tggtggggga tgtgcgcgag gccgtggcgc agcgtgagcg cgcgcagcag   14160
cagggcaacc tgggctccat ggttgcacta aacgccttcc tgagtacaca gcccgccaac   14220
gtgccgcggg gacaggagga ctacaccaac tttgtgagcg cactgcggct aatggtgact   14280
gagacaccgc aaagtgaggt gtaccagtct gggccagact attttttcca gaccagtaga   14340
caaggcctgc agaccgtaaa cctgagccag gctttcaaaa acttgcaggg gctgtggggg   14400
gtgcgggctc ccacaggcga ccgcgcgacc gtgtctagct tgctgacgcc caactcgcgc   14460
ctgttgctgc tgctaatagc gcccttcacg gacagtggca gcgtgtcccg gacacatac    14520 ctaggtcact tgctgacact gtaccgcgag gccataggtc aggcgcatgt ggacgagcat   14580
actttccagg agattacaag tgtcagccgc gcgctggggc aggaggacac gggcagcctg   14640
gaggcaaccc taaactacct gctgaccaac cggcggcaga agatcccctc gttgcacagt   14700
```

```
ttaaacagcg aggaggagcg cattttgcgc tacgtgcagc agagcgtgag ccttaacctg    14760
atgcgcgacg gggtaacgcc cagcgtggcg ctggacatga ccgcgcgcaa catggaaccg    14820
ggcatgtatg cctcaaaccg gccgtttatc aaccgcctaa tggactactt gcatcgcgcg    14880
gccgccgtga accccgagta tttcaccaat gccatcttga acccgcactg gctaccgccc    14940
cctggtttct acaccggggg attcgaggtg cccgagggta cgatggatt cctctgggac     15000 gacatagacg acagcgtgtt ttccccgcaa ccgcagaccc tgctagagtt gcaacagcgc    15060
gagcaggcag aggcggcgct gcgaaaggaa agcttccgca ggccaagcag cttgtccgat    15120
ctaggcgctg cggccccgcg gtcagatgct agtagcccat ttccaagctt gatagggtct    15180
cttaccagca ctcgcaccac ccgcccgcgc ctgctgggcg aggaggagta cctaaacaac    15240
tcgctgctgc agccgcagcg cgaaaaaaac ctgcctccgg catttcccaa caacgggata    15300
gagagcctag tggacaagat gagtagatgg aagacgtacg cgcaggagca cagggacgtg    15360
ccaggcccgc gcccgcccac ccgtcgtcaa aggcacgacc gtcagcgggg tctggtgtgg    15420
gaggacgatg actcggcaga cgacagcagc gtcctggatt tgggagggag tggcaacccg    15480
tttgcgcacc ttcgcccag gctggggaga atgtttaaa aaaaaaaaa gcatgatgca       15540 aaataaaaaa ctcaccaagg ccatggcacc gagcgttggt tttcttgtat tcccttagt     15600 atgcggcgcg cggcgatgta tgaggaaggt cctcctccct cctacgagag tgtggtgagc    15660
gcggcgccag tggcggcggc gctgggttct cccttcgatg ctcccctgga cccgccgttt    15720
gtgcctccgc ggtacctgcg gcctaccggg gggagaaaca gcatccgtta ctctgagttg    15780 gcaccctat tcgacaccac ccgtgtgtac ctggtggaca caagtcaac ggatgtggca      15840 tccctgaact accagaacga ccacagcaac tttctgacca cggtcattca aaacaatgac    15900
tacagcccgg gggaggcaag cacacagacc atcaatcttg acgaccggtc gcactggggc    15960
ggcgacctga aaccatcct gcataccaac atgccaaatg tgaacgagtt catgtttacc     16020
aataagttta aggcgcgggt gatggtgtcg cgcttgccta ctaaggacaa tcaggtggag    16080
ctgaaatacg agtgggtgga gttcacgctg cccgagggca actactccga gaccatgacc    16140
atagacctta tgaacaacgc gatcgtggag cactacttga agtgggcag acagaacggg    16200 gttctggaaa gcgacatcgg ggtaaagttt gacacccgca acttcagact ggggtttgac    16260
cccgtcactg tgtcttgtcat gcctgggggta tatacaaacg aagccttcca tccagacatc    16320
attttgctgc caggatgcgg ggtggacttc acccacagcc gctgagcaa cttgttgggc    16380 atccgcaagc ggcaaccctt ccaggagggc tttaggatca cctacgatga tctgagggt     16440 ggtaacattc ccgcactgtt ggatgtggac gcctaccagg cgagcttgaa agatgacacc    16500
gaacagggcg ggggtggcgc aggcggcagc aacagcagtg gcagcggcgc ggaagagaac    16560
tccaacgcgg cagccgcggc aatgcagccg gtggaggaca tgaacgatca tgccattcgc    16620
ggcgacacct ttgccacacg ggctgaggag aagcgcgctg aggccgaagc agcggccgaa    16680
gctgccgccc ccgctgcgca acccgaggtc gagaagcctc agaagaaacc ggtgatcaaa    16740
cccctgacag aggacagcaa gaaacgcagt tacaacctaa taagcaatga cagcaccttc    16800
acccagtacc gcagctggta ccttgcatac aactacggcg accctcagac cggaatccgc    16860
tcatggaccc tgctttgcac tcctgacgta acctgcggct cggagcaggt ctactggtcg    16920
ttgccagaca tgatgcaaga ccccgtgacc ttccgctcca cgcgccagat cagcaacttt    16980
ccggtggtgg cgccgagct gttgcccgtg cactccaaga gcttctacaa cgaccaggcc    17040
gtctactccc aactcatccg ccagtttacc tctctgaccc acgtgttcaa tcgctttccc    17100
```

```
gagaaccaga ttttggcgcg cccgccagcc cccaccatca ccaccgtcag tgaaaacgtt   17160
cctgctctca cagatcacgg gacgctaccg ctgcgcaaca gcatcggagg agtccagcga   17220
gtgaccatta ctgacgccag acgccgcacc tgccctacg tttacaaggc cctgggcata    17280
gtctcgccgc gcgtcctatc gagccgcact ttttgagcaa gcatgtccat ccttatatcg   17340
cccagcaata acacaggctg gggcctgcgc ttcccaagca agatgtttgg cggggccaag   17400
aagcgctccg accaacaccc agtgcgcgtg cgcgggcact accgcgcgcc ctggggcgcg   17460
cacaaacgcg gccgcactgg gcgcaccacc gtcgatgacg ccatcgacgc ggtggtggag   17520
gaggcgcgca actacacgcc cacgccgcca ccagtgtcca cagtggacgc ggccattcag   17580
accgtggtgc gcggagcccg cgctatgct aaaatgaaga acggcggag gcgcgtagca     17640 cgtcgccacc gccgccgacc cggcactgcc gcccaacgcg cggcggcggc cctgcttaac   17700
cgcgcacgtc gcaccggccg acgggcggcc atgcgggccg ctcgaaggct ggccgcgggt   17760
attgtcactg tgccccccag gtccaggcga cgagcggccg ccgcagcagc gcggccatt    17820 agtgctatga ctcagggtcg caggggcaac gtgtattggg tgcgcgactc ggttagcggc   17880
ctgcgcgtgc ccgtgcgcac ccgccccccg cgcaactaga ttgcaagaaa aaactactta   17940
gactcgtact gttgtatgta tccagcggcg gcggcgcgca acgaagctat gtccaagcgc   18000
aaaatcaaag aagagatgct ccaggtcatc gcgccggaga tctatggccc ccgaagaag    18060 gaagagcagg attacaagcc ccgaaagcta aagcgggtca aaagaaaaa gaaagatgat    18120 gatgatgaac ttgacgacga ggtggaactg ctgcacgcta ccgcgcccag gcgacgggta   18180
cagtggaaag gtcgacgcgt aaaacgtgtt ttgcgacccg gcaccaccgt agtctttacg   18240
cccggtgagc gctccacccg cacctacaag gcgcgtgtatg atgaggtgta cggcgacgag  18300
gacctgcttg agcaggccaa cgagcgcctc ggggagtttg cctacggaaa gcggcataag   18360
gacatgctgg cgttgccgct ggacgagggc aacccaacac ctagcctaaa gcccgtaaca   18420
ctgcagcagg tgctgcccgc gcttgcaccg tccgaagaaa agcgcggcct aaagcgcgag   18480
tctggtgact tggcacccac cgtgcagctg atggtaccca agcgccagcg actggaagat   18540
gtcttggaaa aaatgaccgt ggaacctggg ctggagcccg aggtccgcgt gcggccaatc   18600
aagcaggtgg cgccgggact gggcgtgcag accgtggacg ttcagatacc cactaccagt   18660
agcaccagta ttgccaccgc cacagagggc atggagacac aaacgtcccc ggttgcctca   18720
gcggtggcgg atgccgcggt gcaggcggtc gctgcggccg cgtccaagac ctctacggag   18780
gtgcaaacgg acccgtggat gttcgcgtt tcagcccccc ggcgcccgcg ccgttcgagg    18840
aagtacggcg ccgccagcgc gctactgccc gaatatgccc tacatccttc cattgcgcct   18900 accccccggct atcgtggcta cacctaccgc cccagaagac gagcaactac ccgacgccga   18960
accaccactg gaacccgccg ccgccgtcgc cgtcgccagc ccgtgctggc cccgatttcc   19020
gtgcgcaggg tggctcgcga aggaggcagg accctggtgc tgccaacagc gcgctaccac   19080
cccagcatcg tttaaaagcc ggtctttgtg gttcttgcag atatggccct cacctgccgc   19140
ctccgtttcc cggtgccggg attccgagga agaatgcacc gtaggagggg catggccggc   19200
cacggcctga cgggcggcat gcgtcgtgcg caccaccggc ggcggcgcgc gtcgcaccgt   19260
cgcatgcgcg gcggtatcct gcccctcctt attccactga tcgccgcggc gattggcgcc   19320
gtgcccggaa ttgcatccgt ggccttgcag gcgcagagac actgattaaa acaagttgc    19380 atgtggaaaa atcaaaataa aaagtctgga ctctcacgct cgcttggtcc tgtaactatt   19440
```

```
ttgtagaatg gaagacatca actttgcgtc tctggccccg cgacacggct cgcgcccgtt   19500
catgggaaac tggcaagata tcggcaccag caatatgagc ggtggcgcct tcagctgggg   19560
ctcgctgtgg agcggcatta aaaatttcgg ttccaccgtt aagaactatg gcagcaaggc   19620
ctggaacagc agcacaggcc agatgctgag ggataagttg aaagagcaaa atttccaaca   19680
aaaggtggta gatggcctgg cctctggcat tagcggggtg gtggacctgg ccaaccaggc   19740
agtgcaaaat aagattaaca gtaagcttga tccccgccct cccgtagagg agcctccacc   19800
ggccgtggag acagtgtctc cagaggggcg tggcgaaaag cgtccgcgcc ccgacaggga   19860
agaaactctg gtgacgcaaa tagacgagcc tccctcgtac gaggaggcac taaagcaagg   19920
cctgcccacc acccgtccca tcgcgcccat ggctaccgga gtgctgggcc agcacacacc   19980
cgtaacgctg gacctgcctc cccccgccga cacccagcag aaacctgtgc tgccaggccc   20040
gaccgccgtt gttgtaaccc gtcctagccg cgcgtccctg cgccgcgccg ccagcggtcc   20100
gcgatcgttg cggcccgtag ccagtggcaa ctggcaaagc acactgaaca gcatcgtggg   20160
tctgggggtg caatccctga agcgccgacg atgcttctga tagctaacgt gtcgtatgtg   20220
tgtcatgtat gcgtccatgt cgccgccaga ggagctgctg agccgccgcg cgcccgcttt   20280
ccaagatggc tacccccttcg atgatgccgc agtggtctta catgcacatc tcgggccagg   20340
acgcctcgga gtacctgagc cccgggctgg tgcagtttgc ccgcgccacc gagacgtact   20400
tcagcctgaa taacaagttt agaaaccccca cggtggcgcc tacgcacgac gtgaccacag   20460
accggtccca gcgtttgacg ctgcggttca tccctgtgga ccgtgaggat actgcgtact   20520
cgtacaaggc gcggttcacc ctagctgtgg gtgataaccg tgtgctggac atggcttcca   20580
cgtactttga catccgcggc gtgctggaca ggggccctac ttttaagccc tactctggca   20640
ctgcctacaa cgccctggct cccaagggtg ccccaaatcc ttgcgaatgg gatgaagctg   20700
ctactgctct tgaaataaac ctagaagaag aggacgatga caacgaagac gaagtagacg   20760
agcaagctga gcagcaaaaa actcacgtat ttgggcaggc gccttattct ggtataaata   20820
ttacaaagga gggtattcaa ataggtgtcg aaggtcaaac acctaaatat gccgataaaa   20880
catttcaacc tgaacctcaa ataggagaat ctcagtggta cgaaacagaa attaatcatg   20940
cagctgggag agtcctaaaa aagactaccc caatgaaacc atgttacggt tcatatgcaa   21000
aacccacaaa tgaaaatgga gggcaaggca ttcttgtaaa gcaacaaaat ggaaagctag   21060
aaagtcaagt ggaaatgcaa ttttttctcaa ctactgaggc agccgcaggc aatggtgata   21120
acttgactcc taaagtggta ttgtacagtg aagatgtaga tatagaaacc ccagacactc   21180
atatttctta catgcccact attaaggaag gtaactcacg agaactaatg ggccaacaat   21240
ctatgcccaa caggcctaat tacattgctt ttagggacaa ttttattggt ctaatgtatt   21300
acaacagcac gggtaatatg ggtgttctgg cgggccaagc atcgcagttg aatgctgttg   21360
tagatttgca agacagaaac acagagcttt cataccagct tttgcttgat tccattggtg   21420
atagaaccag gtacttttct atgtggaatc aggctgttga cagctatgat ccagatgtta   21480
gaattattga aaatcatgga actgaagatg aacttccaaa ttactgcttt ccactgggag   21540
gtgtgattaa tacagagact cttaccaagg taaaacctaa aacaggtcag gaaaatggat   21600
gggaaaaaga tgctacagaa ttttcagata aaaatgaaat aagagttgga aataattttg   21660
ccatggaaat caatctaaat gccaacctgt ggagaaattt cctgtactcc aacatagcgc   21720
tgtatttgcc cgacaagcta agtacagtc cttccaacgt aaaaatttct gataacccaa   21780
acacctacga ctacatgaac aagcgagtgg tggctcccgg gctagtggac tgctacatta   21840
```

```
accttggagc acgctggtcc cttgactata tggacaacgt caacccattt aaccaccacc   21900
gcaatgctgg cctgcgctac cgctcaatgt tgctgggcaa tggtcgctat gtgcccttcc   21960
acatccaggt gcctcagaag ttctttgcca ttaaaaacct ccttctcctg ccgggctcat   22020
acacctacga gtggaacttc aggaaggatg ttaacatggt tctgcagagc tccctaggaa   22080
atgacctaag ggttgacgga gccagcatta agtttgatag catttgcctt tacgccacct   22140
tcttccccat ggcccacaac accgcctcca cgcttgaggc catgcttaga aacgacacca   22200
acgaccagtc ctttaacgac tatctctccg ccgccaacat gctctaccct atacccgcca   22260
acgctaccaa cgtgcccata tccatcccct cccgcaactg ggcggctttc cgcggctggg   22320
ccttcacgcg ccttaagact aaggaaaccc catcactggg ctcgggctac gacccttatt   22380
acacctactc tggctctata ccctacctag atggaacctt ttacctcaac cacacccttta  22440
agaaggtggc cattacccttt gactcttctg tcagctggcc tggcaatgac cgcctgctta   22500
cccccaacga gtttgaaatt aagcgctcag ttgacgggga gggttacaac gttgcccagt   22560
gtaacatgac caaagactgg ttcctggtac aaatgctagc taactataac attggctacc   22620
agggcttcta tcccagag agctacaagg accgcatgta ctccttcttt agaaacttcc   22680
agcccatgag ccgtcaggtg gtggatgata ctaaatacaa ggactaccaa caggtgggca   22740
tcctacacca acacaacaac tctggatttg ttggctacct tgcccccacc atgcgcgaag   22800
gacaggccta ccctgctaac ttcccctatc cgcttatagg caagaccgca gttgacagca   22860
ttacccagaa aaagttttctt tgcgatcgca ccctttggcg catcccattc tccagtaact   22920
ttatgtccat gggcgcactc acagacctgg gccaaaacct tctctacgcc aactccgccc   22980
acgcgctaga catgacttttt gaggtggatc ccatggacga gcccacccttt ctttatgttt   23040
tgtttgaagt ctttgacgtg gtccgtgtgc accagccgca ccgcggcgtc atcgaaaccg   23100
tgtacctgcg cacgcccttc tcggccggca acgccacaac ataaagaagc aagcaacatc   23160
aacaacagct gccgccatgg gctccagtga gcaggaactg aaagccattg tcaaagatct   23220
tggttgtggg ccatattttt tgggcaccta tgacaagcgc tttccaggct ttgtttctcc   23280
acacaagctc gcctgcgcca tagtcaatac ggccggtcgc gagactgggg gcgtacactg   23340
gatggccttt gcctggaacc cgcactcaaa aacatgctac ctctttgagc cctttggctt   23400
ttctgaccag cgactcaagc aggtttacca gtttgagtac gagtcactcc tgcgccgtag   23460
cgccattgct tcttccccg accgctgtat aacgctggaa aagtccaccc aaagcgtaca   23520
ggggcccaac tcggccgcct gtggactatt ctgctgcatg tttctccacg cctttgccaa   23580
ctggccccaa actcccatgg atcacaaccc caccatgaac cttattaccg gggtacccaa   23640
ctccatgctc aacagtcccc aggtacagcc caccctgcgt cgcaaccagg aacagctcta   23700
cagcttcctg gagcgccact cgccctactt ccgcagccac agtgcgcaga ttaggagcgc   23760
cacttctttt tgtcacttga aaacatgta aaaataatgt actagagaca ctttcaataa   23820
aggcaaatgc ttttatttgt acactctcgg gtgattattt ccccccaccc ttgccgtctg   23880
cgccgtttaa aaatcaaagg ggttctgccg cgcatcgcta tgcgccactg gcagggacac   23940
gttgcgatac tggtgtttag tgctccactt aaactcagga caaccatcc gcggcagctc   24000
ggtgaagttt tcactccaca ggctgcgcac catcaccaac gcgtttagca ggtcgggcgc   24060
cgatatcttg aagtcgcagt tggggcctcc gccctgcgcg cgcgagttgc gatacacagg   24120
gttgcagcac tggaacacta tcagcgccgg gtggtgcacg ctggccagca cgctcttgtc   24180
```

```
ggagatcaga tccgcgtcca ggtcctccgc gttgctcagg gcgaacggag tcaactttgg   24240
tagctgcctt cccaaaaagg gcgcgtgccc aggctttgag ttgcactcgc accgtagtgg   24300
catcaaaagg tgaccgtgcc cggtctgggc gttaggatac agcgcctgca taaaagcctt   24360
gatctgctta aaagccacct gagcctttgc gccttcagag aagaacatgc cgcaagactt   24420
gccggaaaac tgattggccg gacaggccgc gtcgtgcacg cagcaccttg cgtcggtgtt   24480
ggagatctgc accacatttc ggccccaccg gttcttcacg atcttggcct tgctagactg   24540
ctccttcagc gcgcgctgcc cgttttcgct cgtcacatcc atttcaatca cgtgctcctt   24600
atttatcata atgcttccgt gtagacactt aagctcgcct tcgatctcag cgcagcggtg   24660
cagccacaac gcgcagcccg tgggctcgtg atgcttgtag gtcacctctg caaacgactg   24720
caggtacgcc tgcaggaatc gccccatcat cgtcacaaag gtcttgttgc tggtgaaggt   24780
cagctgcaac ccgcggtgct cctcgttcag ccaggtcttg catacggccg ccagagcttc   24840
cacttggtca ggcagtagtt tgaagttcgc ctttagatcg ttatccacgt ggtacttgtc   24900
catcagcgcg cgcgcagcct ccatgccctt ctcccacgca gacacgatcg gcacactcag   24960
cgggttcatc accgtaattt cactttccgc ttcgctgggc tcttcctctt cctcttgcgt   25020
ccgcatacca cgcgccactg ggtcgtcttc attcagccgc cgcactgtgc gcttacctcc   25080
tttgccatgc ttgattagca ccggtgggtt gctgaaaccc accatttgta gcgccacatc   25140 ttctcttttct cctcgctgt ccacgattac ctctggtgat ggcgggcgct cgggcttggg   25200
agaagggcgc ttcttttttct tcttgggcgc aatggccaaa tccgccgccg aggtcgatgg   25260
ccgcgggctg ggtgtgcgcg gcaccagcgc gtcttgtgat gagtcttcct cgtcctcgga   25320
ctcgatacgc cgcctcatcc gcttttttgg gggcgcccgg ggaggcggcg cgacgggga   25380 cggggacgac acgtcctcca tggttggggg acgtcgcgcc gcaccgcgtc cgcgctcggg   25440
ggtggtttcg cgctgctcct cttcccgact ggccatttcc ttctcctata ggcagaaaaa   25500
gatcatggag tcagtcgaga agaaggacag cctaaccgcc ccctctgagt cgccaccac   25560 cgcctccacc gatgccgcca acgcgcctac caccttcccc gtcgaggcac cccgcttga   25620 ggaggaggaa gtgattatcg agcaggaccc aggttttgta agcgaagacg acgaggaccg   25680
ctcagtacca acagaggata aaaagcaaga ccaggacaac gcagaggcaa cgaggaaca   25740 agtcgggcgg ggggacgaaa ggcatggcga ctacctagat gtgggagacg acgtgctgtt   25800
gaagcatctg cagcgccagt gcgccattat ctgcgacgcg ttgcaagagc gcagcgatgt   25860 gccctcgcc atagcggatg tcagccttgc ctacgaacgc cacctattct caccgcgcgt   25920
accccccaaa cgccaagaaa acggcacatg cgagcccaac ccgcgcctca acttctaccc   25980
cgtatttgcc gtgccagagg tgcttgccac ctatcacatc ttttttccaaa actgcaagat   26040 accctatcc tgccgtgcca accgcagccg agcggacaag cagctggcct tgcggcaggg   26100
cgctgtcata cctgatatcg cctcgctcaa cgaagtgcca aaaatctttg agggtcttgg   26160
acgcgacgag aagcgcgcgg caaacgctct gcaacaggaa aacagcgaaa atgaaagtca   26220
ctctggagtg ttggtggaac tcgagggtga caacgcgcgc ctagccgtac taaaacgcag   26280
catcgaggtc acccactttg cctacccggc acttaaccta cccccaagg tcatgagcac   26340 agtcatgagt gagctgatcg tgcgccgtgc gcagccctg gagagggatg caaatttgca   26400
agaacaaaca gaggagggcc tacccgcagt tggcgacgag cagctagcgc gctggcttca   26460
aacgcgcgag cctgccgact tggaggagcg acgcaaacta atgatggccg cagtgctcgt   26520
taccgtggag cttgagtgca tgcagcggtt ctttgctgac ccggagatgc agcgcaagct   26580
```

```
agaggaaaca ttgcactaca cctttcgaca gggctacgta cgccaggcct gcaagatctc   26640
caacgtggag ctctgcaacc tggtctccta ccttggaatt ttgcacgaaa accgccttgg   26700
gcaaaacgtg cttcattcca cgctcaaggg cgaggcgcgc cgcgactacg tccgcgactg   26760
cgtttactta tttctatgct acacctggca gacggccatg ggcgtttggc agcagtgctt   26820
ggaggagtgc aacctcaagg agctgcagaa actgctaaag caaaacttga aggacctatg   26880
gacggccttc aacgagcgct ccgtggccgc gcacctggcg gacatcattt tccccgaacg   26940
cctgcttaaa accctgcaac agggtctgcc agacttcacc agtcaaagca tgttgcagaa   27000
ctttaggaac tttatcctag agcgctcagg aatcttgccc gccacctgct gtgcacttcc   27060
tagcgacttt gtgcccatta agtaccgcga atgccctccg ccgctttggg gccactgcta   27120
ccttctgcag ctagccaact accttgccta ccactctgac ataatggaag acgtgagcgg   27180
tgacggtcta ctggagtgtc actgtcgctg caacctatgc accccgcacc gctccctggt   27240
ttgcaattcg cagctgctta acgaaagtca aattatcggt acctttgagc tgcagggtcc   27300
ctcgcctgac gaaaagtccg cggctccggg gttgaaactc actccggggc tgtggacgtc   27360
ggcttacctt cgcaaatttg tacctgagga ctaccacgcc cacgagatta ggttctacga   27420
agaccaatcc cgcccgccta atgcggagct taccgcctgc gtcattaccc agggccacat   27480
tcttggccaa ttgcaagcca tcaacaaagc ccgccaagag tttctgctac gaaagggacg   27540 ggggggtttac ttggaccccc agtccggcga ggagctcaac ccaatccccc cgccgccgca   27600
gccctatcag cagcagccgc gggcccttgc ttcccaggat ggcacccaaa agaagctgc   27660 agctgccgcc gccacccacg gacgaggagg aatactggga cagtcaggca gaggaggttt   27720
tggacgagga ggaggaggac atgatggaag actgggagag cctagacgag gaagcttccg   27780
aggtcgaaga ggtgtcagac gaaacaccgt caccctcggt cgcattcccc tcgccggcgc   27840
cccagaaatc ggcaaccggt tccagcatgg ctacaacctc cgctcctcag gcgccgccgg   27900
cactgcccgt tcgccgaccc aaccgtagat gggacaccac tggaaccagg gccggtaagt   27960
ccaagcagcc gccgccgtta gcccaagagc aacaacagcg ccaaggctac cgctcatggc   28020
gcgggcacaa gaacgccata gttgcttgct tgcaagactg tggggggcaac atctccttcg   28080 cccgccgctt tcttctctac catcacggcg tggccttccc ccgtaacatc ctgcattact   28140
accgtcatct ctacagccca tactgcaccg gcggcagcgg cagcaacagc agcggccaca   28200
cagaagcaaa ggcgaccgga tagcaagact ctgacaaagc ccaagaaatc cacagcggcg   28260
gcagcagcag gaggaggagc gctgcgtctg gcgcccaacg aacccgtatc gacccgcgag   28320
cttagaaaca ggattttttcc cactctgtat gctatatttc aacagagcag gggccaagaa   28380
caagagctga aaataaaaaa caggtctctg cgatccctca cccgcagctg cctgtatcac   28440
aaaagcgaag atcagcttcg gcgcacgctg gaagacgcgg aggctctctt cagtaaatac   28500
tgcgcgctga ctcttaagga ctagtttcgc gccctttctc aaatttaagc gcgaaaacta   28560
cgtcatctcc agcggccaca cccggcgcca gcacctgttg tcagcgccat tatgagcaag   28620
gaaattccca cgccctacat gtggagttac cagccacaaa tgggacttgc ggctggagct   28680
gcccaagact actcaacccg aataaactac atgagcgcgg accccacat gatatcccgg   28740 gtcaacggaa tacgcgccca ccgaaaccga attctcctgg aacaggcggc tattaccacc   28800
acacctcgta ataaccttaa tccccgtagt tggcccgctg ccctggtgta ccaggaaagt   28860
cccgctccca ccactgtggt acttcccaga gacgcccagg ccgaagttca gatgactaac   28920
```

```
tcagggcgc agcttgcggg cggctttcgt cacagggtgc ggtcgcccgg gcagggtata  28980
actcacctga caatcagagg gcgaggtatt cagctcaacg acgagtcggt gagctcctcg  29040
cttggtctcc gtccggacgg gacatttcag atcggcggcg ccggccgctc ttcattcacg  29100
cctcgtcagg caatcctaac tctgcagacc tcgtcctctg agccgcgctc tggaggcatt  29160
ggaactctgc aatttattga ggagtttgtg ccatcggtct actttaaccc cttctcggga  29220
cctcccggcc actatccgga tcaatttatt cctaactttg acgcggtaaa ggactcggcg  29280
gacggctacg actgaatgtt aatatgactc tcttaaggta gccaaatagg gataattcga  29340
tttcgcgaag ggcccgagct cggtacccgg ggatctgcat tagttattaa tagtaatcaa  29400
ttacggggtc attagttcat agcccatata tggagttccg cgttacataa cttacggtaa  29460
atggcccgcc tggctgaccg cccaacgacc cccgcccatt gacgtcaata atgacgtatg  29520
ttcccatagt aacgccaata gggactttcc attgacgtca atgggtggag tatttacggt  29580
aaactgccca cttggcagta catcaagtgt atcatatgcc aagtacgccc cctattgacg  29640
tcaatgacgg taaatggccc gcctggcatt atgcccagta catgacctta tgggactttc  29700
ctacttggca gtacatctac gtattagtca tcgctattac catggtgatg cggttttggc  29760
agtacatcaa tgggcgtgga tagcggtttg actcacgggg atttccaagt ctccacccca  29820
ttgacgtcaa tgggagtttg ttttggcacc aaaatcaacg ggactttcca aaatgtcgta  29880
acaactccgc cccattgacg caaatgggcg gtaggcgtgt acggtgggag gtctatataa  29940
gcagagctgg tttagtgaac cgtcagatcc gctagccggt cgccaccatg gtgagcaagg  30000
gcgaggagct gttcaccggg gtggtgccca tcctggtcga gctggacggc gacgtaaacg  30060
gccacaagtt cagcgtgtcc ggcgagggcg agggcgatgc cacctacggc aagctgaccc  30120
tgaagttcat ctgcaccacc ggcaagctgc ccgtgccctg gcccaccctc gtgaccaccc  30180
tgacctacgg cgtgcagtgc ttcagccgct accccgacca catgaagcag cacgacttct  30240
tcaagtccgc catgcccgaa ggctacgtcc aggagcgcac catcttcttc aaggacgacg  30300
gcaactacaa gacccgcgcc gaggtgaagt tcgagggcga caccctggtg aaccgcatcg  30360
agctgaaggg catcgacttc aaggaggacg gcaacatcct ggggcacaag ctggagtaca  30420
actacaacag ccacaacgtc tatatcatgg ccgacaagca gaagaacggc atcaaggtga  30480
acttcaagat ccgccacaac atcgaggacg gcagcgtgca gctcgccgac cactaccagc  30540
agaacacccc catcggcgac ggccccgtgc tgctgcccga caaccactac ctgagcaccc  30600
agtccgccct gagcaaagac cccaacgaga gcgcgatca catggtcctg ctggagttcg  30660
tgaccgccgc cgggatcact ctcggcatgg acgagctgta caagtaaagc ggcctccata  30720
aagtaggaaa cactacacag ctccataaag taggaaacac tacattaatt ccataaagta  30780
ggaaacacta caggactcca taaagtagga aacactacat ctagatcata atcagccata  30840
ccacatttgt agaggtttta cttgctttaa aaaacctccc acacctcccc ctgaacctga  30900
aacataaaat gaatgcaatt gttgttgtta acttgtttat tgcagcttat aatggttaca  30960
aataaagcaa tagcatcaca aatttcacaa ataaagcatt ttttcactg cattctagtt  31020
gtggtttgtc caaactcatc aatgtatctt aagcttggta ccgagctcgg atcatccagc  31080
acagtggcgg ccgctcgacc tgcaggcatg gcggccgcat cgaaatcgcg atataacagg  31140
gtaatattaa gttcctgtcc atccgcaccc actatcttca tgttgttgca gatgaagcgc  31200
gcaagaccgt ctgaagatac cttcaacccc gtgtatccat atgacacgga aaccggtcct  31260
ccaactgtgc cttttcttac tcctccctt gtatccccca atgggttca agagagtccc  31320
```

```
cctggagttc ttactcttaa gtgtttaacc ccactaacaa ccacaggcgg atctctacag   31380
ctaaaagtgg gagggggact tacagtggat gacactgatg gtaccttaca agaaaacata   31440
cgtgctacag cacccattac taaaaataat cactctgtag aactatccat tggaaatgga   31500
ttagaaactc aaaacaataa actatgtgcc aaattgggaa atgggttaaa atttaacaac   31560
ggtgacattt gtataaagga tagtattaac accttatgga ctggaataaa ccctccacct   31620
aactgtcaaa ttgtggaaaa cactaataca aatgatggca aacttacttt agtattagta   31680
aaaaacggag ggcttgttaa tggctacgtg tctctagttg gtgtatcaga cactgtgaac   31740
caaatgttca cacaaaagac agcaaacatc caattaagat tatattttga ctcttctgga   31800
aatctattaa ctgatgaatc agacttaaaa attccactta aaataaaatc ttctacagcg   31860
accagtgaaa ctgtagccag cagcaaagcc tttatgccaa gtactacagc ttatcccttc   31920
aacaccacta ctagggatag tgaaaactac attcatggaa tatgttacta catgactagt   31980
tatgatagaa gtctatttcc cttgaacatt tctataatgc taaacagccg tatgatttct   32040
tccaatgttg cctatgccat acaatttgaa tggaatctaa atgcaagtga atctccagaa   32100
agcaacatag ctacgctgac cacatccccc tttttctttt cttacattac agaagacgac   32160
aactaaaatg aattcagaat cgtttgtgtt atgtttcaac gtgtttattt ttcaattgca   32220
gaaaatttca agtcattttt cattcagtag tatagcccca ccaccacata gcttatacag   32280
atcaccgtac cttaatcaaa ctcacagaac cctagtattc aacctgccac ctccctccca   32340
acacacagag tacacagtcc tttctccccg gctggcctta aaaagcatca tatcatgggt   32400
aacagacata ttcttaggtg ttatattcca cacggtttcc tgtcgagcca acgctcatc    32460 agtgatatta ataaactccc cgggcagctc acttaagttc atgtcgctgt ccagctgctg   32520
agccacaggc tgctgtccaa cttgcggttg cttaacgggc ggcgaaggag aagtccacgc   32580
ctacatgggg gtagagtcat aatcgtgcat caggatagg cggtggtgct gcagcagcgc    32640
gcgaataaac tgctgccgcc gccgctccgt cctgcaggaa tacaacatgg cagtggtctc   32700
ctcagcgatg attcgcaccg cccgcagcat aaggcgcctt gtcctccggg cacagcagcg   32760
caccctgatc tcacttaaat cagcacagta actgcagcac agcaccacaa tattgttcaa   32820
aatcccacag tgcaaggcgc tgtatccaaa gctcatggcg gggaccacag aacccacgtg   32880
gccatcatac cacaagcgca ggtagattaa gtggcgaccc ctcataaaca cgctggacat   32940
aaacattacc tcttttggca tgttgtaatt caccacctcc cggtaccata taaacctctg   33000
attaaacatg gcgccatcca ccaccatcct aaaccagctg ccaaaacct gcccgccggc    33060 tatacactgc agggaaccgg gactggaaca atgacagtgg agagcccagg actcgtaacc   33120
atggatcatc atgctcgtca tgatatcaat gttggcacaa cacaggcaca cgtgcataca   33180
cttcctcagg attacaagct cctcccgcgt tagaaccata tcccagggaa caacccattc   33240
ctgaatcagc gtaaatccca cactgcaggg aagacctcgc acgtaactca cgttgtgcat   33300
tgtcaaagtg ttacattcgg gcagcagcgg atgatcctcc agtatggtag cgcgggtttc   33360
tgtctcaaaa ggaggtagac gatccctact gtacggagtg cgccgagaca accgagatcg   33420
tgttggtcgt agtgtcatgc caaatggaac gccggacgta gtcatatttc ctgaagcaaa   33480
accaggtgcg ggcgtgacaa acagatctgc gtctccggtc tcgccgctta gatcgctctg   33540
tgtagtagtt gtagtatatc cactctctca aagcatccag gcgcccctg gcttcgggtt     33600 ctatgtaaac tccttcatgc gccgctgccc tgataacatc caccaccgca gaataagcca   33660
```

-continued

```
cacccagcca acctacacat tcgttctgcg agtcacacac gggaggagcg ggaagagctg    33720
gaagaaccat gtttttttt ttattccaaa agattatcca aaacctcaaa atgaagatct    33780
attaagtgaa cgcgctcccc tccggtggcg tggtcaaact ctacagccaa agaacagata    33840
atggcatttg taagatgttg cacaatggct tccaaaaggc aaacggccct cacgtccaag    33900
tggacgtaaa ggctaaaccc ttcagggtga atctcctcta taaacattcc agcaccttca    33960
accatgccca ataattctc atctcgccac cttctcaata tatctctaag caaatcccga    34020
atattaagtc cggccattgt aaaaatctgc tccagagcgc cctccacctt cagcctcaag    34080
cagcgaatca tgattgcaaa aattcaggtt cctcacagac ctgtataaga ttcaaaagcg    34140
gaacattaac aaaaataccg cgatcccgta ggtcccttcg cagggccagc tgaacataat    34200
cgtgcaggtc tgcacggacc agcgcggcca cttccccgcc aggaaccatg acaaaagaac    34260
ccacactgat tatgacacgc atactcggag ctatgctaac cagcgtagcc ccgatgtaag    34320
cttgttgcat gggcggcgat ataaaatgca aggtgctgct caaaaaatca ggcaaagcct    34380
cgcgcaaaaa agaaagcaca tcgtagtcat gctcatgcag ataaaggcag gtaagctccg    34440
gaaccaccac agaaaagac accattttc tctcaaacat gtctgcgggt ttctgcataa    34500
acacaaaata aaataacaaa aaaacattta aacattagaa gcctgtctta caacaggaaa    34560 aacaacccctt ataagcataa gacggactac ggccatgccg gcgtgaccgt aaaaaaactg    34620
gtcaccgtga ttaaaaagca ccaccgacag ctcctcggtc atgtccggag tcataatgta    34680
agactcggta aacacatcag gttgattcac atcggtcagt gctaaaaagc gaccgaaata    34740
gcccggggga atacataccc gcaggcgtag agacaacatt acagcccca taggaggtat    34800 aacaaaatta ataggagaga aaaacacata aacacctgaa aaaccctcct gcctaggcaa    34860
aatagcaccc tcccgctcca gaacaacata cagcgcttcc acagcggcag ccataacagt    34920
cagccttacc agtaaaaaag aaaacctatt aaaaaaacac cactcgacac ggcaccagct    34980
caatcagtca cagtgtaaaa aagggccaag tgcagagcga gtatatatag gactaaaaaa    35040
tgacgtaacg gttaaagtcc acaaaaaaca cccagaaaac cgcacgcgaa cctacgccca    35100
gaaacgaaag ccaaaaaacc cacaacttcc tcaaatcgtc acttccgttt tcccacgtta    35160
cgtcacttcc cattttaaga aaactacaat tcccaacacc tctagagaca agttactccg    35220
ccctaaaacc tacgtcaccc gccccgttcc cacgccccgc gccacgtcac aaactccacc    35280
ccctcattat catattggct tcaatccaaa ataaggtata ttat                     35324
```

```
<210> SEQ ID NO 52
<211> LENGTH: 105
<212> TYPE: DNA
<213> ORGANISM: Artificial Sequence
<220> FEATURE:
<223> OTHER INFORMATION: synthetic DNA

<400> SEQUENCE: 52
tccataaagt aggaaacact acacagctcc ataaagtagg aaacactaca ttaattccat    60
aaagtaggaa acactacagg actccataaa gtaggaaaca ctaca                    105

<210> SEQ ID NO 53
<211> LENGTH: 4059
<212> TYPE: DNA
<213> ORGANISM: Artificial Sequence
<220> FEATURE:
<223> OTHER INFORMATION: synthetic DNA
```

```
<400> SEQUENCE: 53
tggcccctcc ctcgggttac cccacagcct aggccgattc gacctctctc cgctggggcc      60
ctcgctggcg tccctgcacc ctgggagcgc gagcggcgcg cgggcgggga agcgcggccc     120
agacccccgg gtccgcccgg agcagctgcg ctgtcgggc caggccggc tcccagtgga      180 ttcgcgggca cagacgccca ggaccgcgct ccccacgtgg cggagggact ggggacccgg     240
gcacccgtcc tgccccttca ccttccagct ccgcctcctc cgcgcggacc ccgcccgtc     300 ccgacccctc ccgggtcccc ggcccagccc cctccgggcc ctcccagccc ctcccccttcc    360 tttccgcggc cccgccctct cctcgcgcg cgagtttcag gcagcgctgc gtcctgctgc     420
gcacgtggga agccctggcc ccggccaccc ccgcgataga tctcgagaat tcacgcgaat    480
tcggcttaca ccgggactga aaatgagaca tattatctgc cacggagtg ttattaccga      540 agaaatggcc gccagtctt tggaccagct gatcgaagag gtactggctg ataatcttcc     600
acctcctagc cattttgaac cacctaccct tcacgaactg tatgatttag acgtgacggc    660
ccccgaagat cccaacgagg aggcggtttc gcagattttt ccgactctg taatgttggc     720 ggtgcaggaa gggattgact tactcacttt tccgccggcg cccggttctc cggagccgcc    780
tcacctttcc cggcagcccg agcagccgga gcagagagcc ttgggtccgg tttctatgcc    840
aaaccttgta ccggaggtga tcgatcttac ctgccacgag gctggctttc cacccagtga    900
cgacgaggat gaagagggtg aggagtttgt gttagattat gtggagcacc ccgggcacgg    960
ttgcaggtct tgtcattatc accggaggaa tacgggggac ccagatatta tgtgttcgct   1020
ttgctatatg aggacctgtg gcatgtttgt ctacagtcct gtgtctgaac ctgagcctga   1080
gcccgagcca gaaccggagc ctgcaagacc tacccgccgt cctaaaatgg cgcctgctat    1140
cctgagacgc ccgacatcac ctgtgtctag agaatgcaat agtagtacgg atagctgtga   1200
ctccggtcct tctaacacac ctcctgagat acaccggtg gtcccgctgt gccccattaa    1260
accagttgcc gtgagagttg gtgggcgtcg ccaggctgtg gaatgtatcg aggacttgct   1320
taacgagcct gggcaacctt tggacttgag ctgtaaacgc cccaggccat aaggtgtaaa   1380
cctgtgaagc cgaattcgcg tcgagcatgc atctagggcg gccaattccg ccctctcccc    1440
ccccccccct ctccctcccc cccccccctaa cgttactggc cgaagccgct tggaataagg    1500
ccggtgtgcg tttgtctata tgttattttc caccatattg ccgtcttttg gcaatgtgag    1560
ggcccggaaa cctggccctg tcttcttgac gagcattcct aggggtcttt ccctctcgc    1620 caaaggaatg caaggtctgt tgaatgtcgt gaaggaagca gttcctctgg aagcttcttg    1680
aagacaaaca acgtctgtag cgaccctttg caggcagcgg aaccccccac ctggcgacag    1740
gtgcctctgc ggccaaaagc cacgtgtata agatacacct gcaaaggcgg cacaaccca    1800 gtgccacgtt gtgagttgga tagttgtgga aagagtcaaa tggctctcct caagcgtatt    1860
caacaagggg ctgaaggatg cccagaaggt accccattgt atgggatctg atctggggcc   1920
tcggtgcaca tgctttacat gtgtttagtc gaggttaaaa aaacgtctag gcccccgaa    1980 ccacggggac gtggttttcc tttgaaaaac acgatgataa gcttgccaca acccgggatc   2040
ctctagagtc gaaattcggc ttctgacctc atggaggctt gggagtgttt ggaagatttt   2100
tctgctgtgc gtaacttgct ggaacagagc tctaacagta cctcttggtt ttggaggttt   2160
ctgtggggct catcccaggc aaagttagtc tgcagaatta aggaggatta caagtgggaa   2220
tttgaagagc ttttgaaatc ctgtggtgag ctgtttgatt ctttgaatct gggtcaccag   2280
gcgcttttcc aagagaaggt catcaagact ttggattttt ccacaccggg gcgcgctgcg   2340
```

-continued

```
gctgctgttg cttttttgag ttttataaag gataaatgga gcgaagaaac ccatctgagc    2400
gggggtacc tgctggattt tctggccatg catctgtgga gagcggttgt gagacacaag     2460
aatcgcctgc tactgttgtc ttccgtccgc ccggcgataa taccgacgga ggagcagcag    2520
cagcagcagg aggaagccag gcggcggcgg caggagcaga gcccatggaa cccgagagcc    2580
ggcctggacc ctcgggaatg aatgttgtac aggtggctga actgtatcca gaactgagac    2640
gcattttgac aattacagag gatgggcagg ggctaaaggg ggtaaagagg gagcgggggg    2700
cttgtgaggc tacagaggag gctaggaatc tagcttttag cttaatgacc agacaccgtc    2760
ctgagtgtat tacttttcaa cagatcaagg ataattgcgc taatgagctt gatctgctgg    2820
cgcagaagta ttccatagag cagctgacca cttactggct gcagccaggg gatgattttg    2880
aggaggctat tagggtatat gcaaaggtgg cacttaggcc agattgcaag tacaagatca    2940
gcaaacttgt aaatatcagg aattgttgct acatctctgg gaacggggcc gaggtggaga    3000
tagatacgga ggatagggtg gcctttagat gtagcatgat aaatatgtgg ccggggtgc    3060
ttggcatgga cggggtggtt attatgaatg taaggtttac tggccccaat tttagcggta    3120
cggttttcct ggccaatacc aaccttatcc tacacggtgt aagcttctat gggtttaaca    3180
atacctgtgt ggaagcctgg accgatgtaa gggttcgggg ctgtgccttt tactgctgct    3240
ggaaggggt ggtgtgtcgc cccaaaagca gggcttcaat taagaaatgc ctctttgaaa     3300
ggtgtacctt gggtatcctg tctgagggta actccagggt gcgccacaat gtggcctccg    3360
actgtggttg cttcatgcta gtgaaaagcg tggctgtgat taagcataac atggtatgtg    3420
gcaactgcga ggacagggcc tctcagatgc tgacctgctc ggacggcaac tgtcacctgc    3480
tgaagaccat tcacgtagcc agccactctc gcaaggcctg gccagtgttt gagcataaca    3540
tactgacccg ctgttccttg catttgggta acaggagggg ggtgttccta ccttaccaat    3600
gcaatttgag tcacactaag atattgcttg agcccgagag catgtccaag gtgaacctga    3660
acggggtgtt tgacatgacc atgaagatct ggaaggtgct gaggtacgat gagacccgca    3720
ccaggtgcag accctgcgag tgtggcggta acatattag gaaccagcct gtgatgctgg     3780
atgtgaccga ggagctgagg cccgatcact tggtgctggc ctgcacccgc gctgagtttg    3840
gctctagcga tgaagataca gattgaggta ctgaaatatg tgggcaagcc gaatttcgac    3900
ccgggcggcc tagcgtttct agcgtttaaa cgggccctct agactcgagc ggcctccata    3960
aagtaggaaa cactacacag ctccataaag taggaaacac tacattaatt ccataaagta    4020
ggaaacacta caggactcca taaagtagga aacactaca                           4059
```

<210> SEQ ID NO 54
<211> LENGTH: 1439
<212> TYPE: DNA
<213> ORGANISM: Artificial Sequence
<220> FEATURE:
<223> OTHER INFORMATION: synthetic DNA

<400> SEQUENCE: 54

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
```

```
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagccggt    600
cgccaccatg gtgagcaagg gcgaggagct gttcaccggg gtggtgccca tcctggtcga    660
gctggacggc gacgtaaacg gccacaagtt cagcgtgtcc ggcgagggcg agggcgatgc    720
cacctacggc aagctgaccc tgaagttcat ctgcaccacc ggcaagctgc ccgtgccctg    780
gcccaccctc gtgaccaccc tgacctacgg cgtgcagtgc ttcagccgct accccgacca    840
catgaagcag cacgacttct tcaagtccgc catgcccgaa ggctacgtcc aggagcgcac    900
catcttcttc aaggacgacg gcaactacaa gacccgcgcc gaggtgaagt tcgagggcga    960
caccctggtg aaccgcatcg agctgaaggg catcgacttc aaggaggacg gcaacatcct   1020
ggggcacaag ctggagtaca actacaacag ccacaacgtc tatatcatgg ccgacaagca   1080
gaagaacggc atcaaggtga acttcaagat ccgccacaac atcgaggacg gcagcgtgca   1140
gctcgccgac cactaccagc agaacacccc catcggcgac ggccccgtgc tgctgcccga   1200
caaccactac ctgagcaccc agtccgccct gagcaaagac cccaacgaga agcgcgatca   1260
catggtcctg ctggagttcg tgaccgccgc cgggatcact ctcggcatgg acgagctgta   1320
caagtaaagc ggcctccata aagtaggaaa cactacacag ctccataaag taggaaacac   1380
tacattaatt ccataaagta ggaaacacta caggactcca taaagtagga aacactaca    1439

<210> SEQ ID NO 55
<211> LENGTH: 105
<212> TYPE: DNA
<213> ORGANISM: Artificial Sequence
<220> FEATURE:
<223> OTHER INFORMATION: synthetic DNA

<400> SEQUENCE: 55
tccataaagt aggaaacact acacagctcc ataaagtagg aaacactaca ttaattccat     60
aaagtaggaa acactacacc actccataaa gtaggaaaca ctaca                    105
```

CONDITIONALLY REPLICATING ADENOVIRUS

This application is a continuation-in-part application of U.S. application Ser. No. 14/240,216 filed on Mar. 12, 2014, which is the U.S. National Phase of International Patent Application No. PCT/JP2012/053814, filed on Feb. 17, 2012, and claims the benefit of the filing date of JP application 2011-181414 filed on Aug. 23, 2011. These documents are hereby incorporated by reference for all purposes.

REFERENCE TO SEQUENCE LISTING SUBMITTED VIA EFS-WEB

This application includes an electronically submitted sequence listing in .txt format. The .txt file contains a sequence listing entitled "2016-06-15_Sequence Listing_4456-0189PUS2.txt" created on Jun. 15, 2016 and is 137,556 bytes in size. The sequence listing contained in this .txt file is part of the specification and is hereby incorporated by reference herein in its entirety.

TECHNICAL FIELD

The present invention relates to a novel conditionally replicating adenovirus and a reagent comprising the same for cancer cell detection or for cancer diagnosis.

BACKGROUND ART

Techniques currently used for cancer diagnosis mainly include (i) those using large-sized testing instruments (e.g., MRI) and (ii) those for measuring tumor markers or the like in blood, and expectations are now focused on (ii) which are simple techniques with less burden on patients. In particular, cancer cells circulating in the peripheral blood of cancer patients (i.e., circulating tumor cells (CTCs)) show a close relationship with clinical symptoms because these cells increase the risk of systemic metastasis and because the prognosis of patients with CTCs is significantly poor. Thus, it has been expected to develop a technique for simple and highly sensitive detection of CTCs as a predictive factor or surrogate marker for prognosis.

Techniques used for CTC detection include detection with a cancer-related antigen such as EpCAM (epithelial cell adhesion molecule) or cytokeratin-8 (e.g., CellSearch system) and detection by means of RT-PCR, etc. However, these cancer-related antigens are also expressed on normal epithelial cells and hence are highly likely to cause false positive detection, while cell morphology characteristic of cancer cells cannot be observed at the same time in the case of PCR detection. For these reasons. there has been a demand for a new technique in terms of sensitivity, simplicity, accuracy and costs.

On the other hand, the inventors of the present invention have already developed a conditionally replicating adenovirus which grows specifically in cancer cells and expresses GFP (GFP-expressing conditionally replicating adenovirus: GFP-CRAd) (which is referred to as TelomeScan®, OBP-401 or Telomelysin-GFP) (Patent Document 1: WO2006/036004). Moreover, the inventors of the present invention have also developed a simple technique for CTC detection using this TelomeScan (Non-patent Document 1: Kojima T, et al, J. Clin. Invest., 119: 3172, 2009).

However, since TelomeScan has the fiber protein of adenovirus type 5 and infects via coxsackievirus and adenovirus receptor (CAR) in target cells, TelomeScan may not infect cells which do not express CAR. In particular, it is known that CAR expression is reduced in highly malignant cancer cells which are highly invasive. metastatic and proliferative (Non-patent Document 2: Okegawa T., et al, Cancer Res., 61: 6592-6600, 2001); and hence TelomeScan may not detect these highly malignant cancer cells. Moreover, although less likely. TelomeScan may give false positive results by infecting and growing in normal blood cells (e.g., leukocytes) to cause GFP expression.

For these reasons, there has been a demand for a reagent for cancer cell detection and a reagent for cancer diagnosis, each of which detects almost all cancer cells including CAR-negative ones and does not give any false positive results in normal blood cells.

PRIOR ART DOCUMENTS

Patent Documents

Patent Document 1: WO2006/036004
Non-patent Document 1: Kojima T., et al, J. Clin. Invest., 119: 3172, 2009
Non-patent Document 2: Okegawa T., et al, Cancer Res., 61: 6592-6600, 2001

SUMMARY OF THE INVENTION

Problem to be Solved by the Invention

The present invention has been made under these circumstances, and the problem to be solved by the present invention is to provide a reagent for cancer cell detection and a reagent for cancer diagnosis, each of which detects almost all cancer cells including CAR-negative ones and does not give any false positive results in blood cells, as well as to provide a conditionally replicating recombinant adenovirus which is useful as such a reagent.

Means to Solve the Problem

As a result of extensive and intensive efforts made to solve the above problem, the inventors of the present invention have found that not only CAR-positive cells, but also CAR-negative cells can be detected when the fiber of adenovirus type 5 in TelomeScan is replaced with another adenovirus fiber binding to CD46, which is highly expressed on almost all human cells, particularly cancer cells in general. Moreover, the inventors of the present invention have succeeded in avoiding any false positive results in blood cells by integration of a microRNA (miRNA)-mediated gene regulatory system into TelomeScan, which led to the completion of the present invention.

Namely, the present invention is as follows.

(1) A polynucleotide, which comprises human telomerase reverse transcriptase promoter, E1A gene, IRES sequence and E1B gene in this order and which comprises a target sequence of a first microRNA.

(2) The polynucleotide according to (1) above, wherein the first microRNA is expressed in non-cancer cells.

(3) The polynucleotide according to (1) or (2) above, wherein the first microRNA is at least one selected from the group consisting of miR-142, miR-15, miR-16, miR-21, miR-126, miR-181, miR-223, miR-296, miR-125, miR-143, miR-145, miR-199 and let-7.

(4) A recombinant adenovirus, which comprises a replication cassette comprising the polynucleotide according to any one of (1) to (3) above, wherein the replication cassette is integrated into the E1 region of the adenovirus genome.

(5) The recombinant adenovirus according to (4) above, which further comprises a labeling cassette comprising a reporter gene and a promoter capable of regulating the expression of the gene, wherein the labeling cassette is integrated into the E3 region of the adenovirus genome.

(6) The recombinant adenovirus according to (5) above, wherein the labeling cassette further comprises a target sequence of a second microRNA.

(7) The recombinant adenovirus according to (4) above, wherein a cell death-inducing cassette comprising a gene encoding a cell death induction-related protein and a promoter capable of regulating the expression of the gene is further integrated into the E3 region of the adenovirus genome.

(8) The recombinant adenovirus according to (7) above, wherein the cell death-inducing cassette further comprises a target sequence of a second microRNA.

(9) The recombinant adenovirus according to (6) or (8) above, wherein the second microRNA is expressed in non-cancer cells.

(10) The recombinant adenovirus according to (9) above, wherein the second microRNA is at least one selected from the group consisting of miR-142, miR-15, miR-16, miR-21, miR-126, miR-181, miR-223, miR-296, miR-125, miR-143, miR-145, miR-199 and let-7.

(11) The recombinant adenovirus according to (5) or (6) above, wherein the reporter gene is a gene encoding a protein which emits fluorescence or a gene encoding an enzyme protein which generates a luminophore or a chromophore upon enzymatic reaction.

(12) The recombinant adenovirus according to any one of (5) to (10) above, wherein the promoter is human telomerase reverse transcriptase promoter or cytomegalovirus promoter.

(13) The recombinant adenovirus according to any one of (4) to (12) above, which further comprises a gene encoding a CD46-binding fiber protein.

(14) The recombinant adenovirus according to (13) above, wherein the CD46-binding fiber protein comprises at least the fiber knob region in the fiber protein of adenovirus type 34 or 35.

(15) A reagent for cancer cell detection, which comprises the recombinant adenovirus according to any one of (4) to (14) above.

(16) A reagent for cancer diagnosis, which comprises the recombinant adenovirus according to any one of (4) to (14) above.

(17) The reagent according to (15) above, wherein the cancer cells are derived from a biological sample taken from a subject.

(18) The reagent according to (17) above, wherein the biological sample is blood.

(19) The reagent according to (15) or (18) above, wherein the cancer cells are circulating tumor cells.

(20) The reagent according to any one of (15) and (17) to (19) above, wherein the cancer cells are drug-resistant cancer cells.

(21) The reagent according to any one of (15) and (17) to (20) above, wherein the cancer cells are cancer stem cells.

(22) The reagent according to any one of (15) and (17) to (21) above, wherein the cancer cells are cancer cells having undergone epithelial-mesenchymal transition or mesenchymal-epithelial transition.

(23) A method for cancer cell detection, which comprises contacting cancer cells with the recombinant adenovirus according to (11) above and detecting the fluorescence or color produced by the cancer cells.

(24) The method according to (23) above, wherein the cancer cells are derived from a biological sample taken from a subject.

(25) The method according to (24) above, wherein the biological sample is blood.

(26) The method according to (25) above, wherein the cancer cells are circulating tumor cells.

(27) A recombinant adenovirus, which comprises:
a replication cassette comprising a polynucleotide comprising a human telomerase reverse transcriptase promoter, E1A gene, IRES sequence and E1B gene in this order, and a target sequence of a first microRNA, wherein the first microRNA is miR-142 and the target sequence comprises a nucleotide sequence having at least 98% identity to the nucleotide sequence consisting of SEQ ID NO: 52, and wherein the replication cassette is integrated into the E1 region of the adenovirus genome;
a labeling cassette comprising a reporter gene, a promoter capable of regulating the expression of the reporter gene, and a target sequence of a second microRNA, wherein the second microRNA is miR-142 and the target sequence comprises a nucleotide sequence having at least 98% identity to the nucleotide sequence consisting of SEQ ID NO: 52, and wherein the labeling cassette is integrated into the E3 region of the adenovirus genome; and
a gene encoding a CD46-binding fiber protein comprising at least the fiber knob region in the fiber protein of adenovirus type 34 or 35, which comprises a nucleotide sequence having at least 99% identity to the nucleotide sequence consisting of SEQ ID NO: 50 and is integrated into the adenovirus genome.

(28) The recombinant adenovirus according to (27) above, wherein the reporter gene is a gene encoding a protein which emits fluorescence or a gene encoding an enzyme protein which generates a luminophore or a chromophore upon enzymatic reaction.

(29) The recombinant adenovirus according to (27) above, wherein the promoter capable of regulating the expression of the reporter gene is a human telomerase reverse transcriptase promoter or cytomegalovirus promoter.

(30) The recombinant adenovirus according to (27) above, wherein the replication cassette comprises a nucleotide sequence having at least 99% identity to the nucleotide sequence consisting of SEQ ID NO: 53.

(31) The recombinant adenovirus according to (27) above, wherein the labeling cassette comprises a nucleotide sequence having at least 99% identity to the nucleotide sequence consisting of SEQ ID NO: 54.

(32) A recombinant adenovirus, which comprises:
a replication cassette comprising a nucleotide sequence having at least 99% identity to the nucleotide sequence consisting of SEQ ID NO: 53 and is integrated into the E1 region of the adenovirus genome:
a labeling cassette comprising a nucleotide sequence having at least 99% identity to the nucleotide sequence consisting of SEQ ID NO: 54 and is integrated into the E3 region of the adenovirus genome; and
a gene encoding a CD46-binding fiber protein comprising a nucleotide sequence having at least 99% identity to the nucleotide sequence consisting of SEQ ID NO: 50 and is integrated into the adenovirus genome.

(33) A recombinant adenovirus, which comprises a nucleotide sequence having at least 99% identity to the nucleotide sequence consisting of SEQ ID NO: 51.

Effects of the Invention

The present invention enables simple and highly sensitive detection of CAR-negative cancer cells without detection of normal blood cells (e.g., leukocytes).

DESCRIPTION OF EMBODIMENTS

The present invention will be described in more detail below. The following embodiments are illustrated to describe the present invention, and it is not intended to limit the present invention only to these embodiments. The present invention can be implemented in various modes, without departing from the spirit of the present invention. Moreover, this specification incorporates the contents disclosed in the specification and drawings of Japanese Patent Application No. 2011-181414 (filed on Aug. 23, 2011), based on which the present application claims priority.

1. SUMMARY

TelomeScan (i.e., a conditionally replicating adenovirus comprising hTERT promoter, E1A gene, IRES sequence and E1B gene integrated in this order into the E1-deficient region of adenovirus type 5 and comprising cytomegalovirus (CMV) promoter and GFP integrated in this order into the E3-deficient region of adenovirus type 5), which has been previously developed by the inventors of the present invention, has problems in that: (i) TelomeScan may not detect highly malignant cancer cells where CAR expression is reduced; and (ii) TelomeScan may detect normal blood cells as false positive. As a result of extensive and intensive efforts made to solve these problems, the inventors of the present invention have found that highly malignant CAR-negative cancer cells can be detected when the fiber of adenovirus type 5 in TelomeScan is replaced with another adenovirus fiber binding to CD46, which is highly expressed on almost all human cells, particularly cancer cells in general. Moreover, the inventors of the present invention have also found that when a target sequence of miR-142-3p, which is miRNA, is integrated into each of the replication and labeling cassettes in TelomeScan, virus growth and labeling protein expression can be prevented in normal blood cells to thereby prevent the occurrence of false positive results in normal blood cells.

Figure 1:
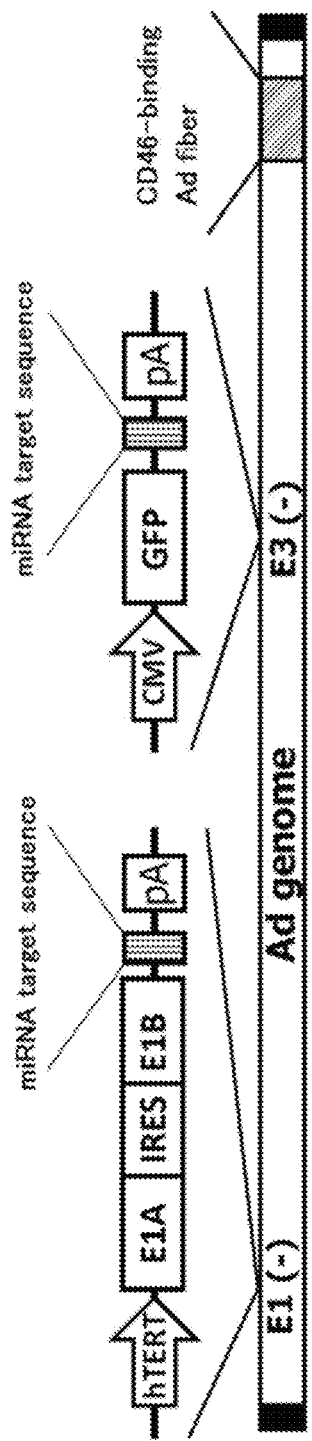
FIG. 1 is a schematic view showing an example of the structure of the recombinant adenovirus of the present invention.

Namely, in a preferred embodiment of the present invention, the recombinant adenovirus of the present invention is a recombinant adenovirus, in which a replication cassette comprising hTERT promoter, E1A gene, IRES sequence, E1B gene and a target sequence of microRNA is integrated into the E1 region of the adenovirus genome and a labeling cassette comprising a reporter gene, a promoter capable of regulating the expression of the gene and a target sequence of microRNA is integrated into the E3 region of the adenovirus genome, and which comprises a gene encoding a CD46-binding adenovirus fiber protein (FIG. 1). This recombinant adenovirus has the following features.

(i) Because of comprising a gene encoding a CD46-binding adenovirus fiber protein, this recombinant adenovirus is able to infect almost all cells including CAR-negative cells.

(ii) Because of comprising hTERT promoter, this recombinant adenovirus grows specifically in hTERT-expressing cancer cells and also increases reporter gene expression upon growth, whereby the production of a labeling protein, a chromophore or the like can be increased to detectable levels.

(iii) Because of comprising a target sequence of miRNA, this recombinant adenovirus can prevent the occurrence of false positive results even when the virus infects normal cells having hTERT promoter activity, because expression of this miRNA prevents not only growth of the virus but also expression of the reporter gene. In particular, because of comprising a target sequence of miRNA which is expressed specifically in blood cells, this recombinant adenovirus can prevent the occurrence of false positive results even when the virus infects normal blood cells having hTERT promoter activity, because expression of this miRNA prevents not only growth of the virus in blood cells but also expression of the reporter gene.

The present invention has been completed on the basis of these findings.

2. RECOMBINANT ADENOVIRUS (1) Replication Cassette

The present invention relates to a polynucleotide, which comprises human telomerase reverse transcriptase (hTERT) promoter, E1A gene, IRES sequence and E1B gene in this order and which comprises a target sequence of microRNA. In addition, the present invention relates to a recombinant adenovirus, which comprises a replication cassette comprising the above polynucleotide, wherein the replication cassette is integrated into the E1 region of the adenovirus genome.

By the action of the above polynucleotide (or a replication cassette comprising the same), the recombinant adenovirus of the present invention can grow specifically in cancer cells and can also be prevented from growing in cells which express the desired miRNA. For example, if the target sequence of miRNA contained in the replication cassette of the present invention is a target sequence of miRNA which is expressed specifically in blood cells, the recombinant adenovirus of the present invention grows specifically in hTERT-expressing cancer cells and is prevented from growing in blood cells.

Human telomerase reverse transcriptase (hTERT) promoter is a promoter for reverse transcriptase which is an element of human telomerase. Although human telomerase activity will be increased by splicing of hTERT mRNA, post-translational modification of hTERT protein and other events, enhanced hTERT gene expression, i.e., increased hTERT promoter activity is thought to be the most important molecular mechanism. Human telomerase has been confirmed to show increased activity in 85% or more of human cancers, whereas it shows no activity in most normal cells. Thus, the use of hTERT promoter allows a gene downstream thereof to be expressed specifically in cancer cells. In the present invention, the hTERT promoter is located upstream of E1A gene, IRES sequence and E1B gene, whereby the virus can grow specifically in hTERT-expressing cancer cells.

hTERT has been confirmed to have many transcription factor binding sequences in a 1.4 kbp region upstream of its 5'-terminal end, and this region is regarded as hTERT promoter. In particular, a 181 bp sequence upstream of the translation initiation site is a core region important for expression of its downstream genes. In the present invention, although any sequence may be used as long as it includes this core region, an upstream sequence of approximately 378 bp which covers this core region in its entirety is preferred for use as the hTERT promoter. This sequence of approximately 378 bp has been confirmed to have the same efficiency of gene expression as the 181 bp core region alone. The nucleotide sequence of a 455 bp long hTERT promoter is shown in SEQ ID NO: 1.

In addition to the sequence shown in SEQ ID NO: 1, the nucleotide sequence of hTERT promoter includes the nucleotide sequences of polynucleotides which are hybridizable under stringent conditions with DNA consisting of a nucleotide sequence complementary to DNA consisting of SEQ ID NO: 1 and which have hTERT promoter activity. Such polynucleotides may be obtained from cDNA and genomic libraries by known hybridization techniques (e.g., colony hybridization, plaque hybridization, Southern blotting) using a polynucleotide which consists of the nucleotide sequence shown in SEQ ID NO: 1 or a fragment thereof as a probe.

For preparation of cDNA libraries, reference may be made to "Molecular Cloning, A Laboratory Manual 2nd ed." (Cold Spring Harbor Press (1989)). Alternatively, commercially available cDNA and genomic libraries may also be used for this purpose.

Stringent conditions in the above hybridization include, for example, conditions of 1×SSC to 2×SSC, 0.1% to 0.5% SDS and 42° C. to 68° C., more specifically prehybridization at 60° C. to 68° C. for 30 minutes or longer and the subsequent 4 to 6 washings in 2×SSC, 0.1% SDS at room temperature for 5 to 15 minutes.

As to detailed procedures for hybridization, reference may be made to "Molecular Cloning, A Laboratory Manual 2nd ed." (Cold Spring Harbor Press (1989); particularly Section 9.47-9.58), etc.

In a preferred embodiment of the invention, the hTERT promoter comprises the nucleotide sequence of SEQ ID NO: 1 or a variant thereof. The variant of the hTERT promoter comprises the nucleotide sequence having at least 90%, preferably at least 95%, more preferably at least 96%, and even more preferably at least 97%, 98%, or 99% identity to that of SEQ ID NO: 1, wherein the nucleotide sequence has an hTERT promoter activity.

E1A and E1B genes are both included in the E1 gene of adenovirus. This E1 gene refers to one of the early genes among the virus early (E) and late (L) genes related to DNA replication, and it encodes a protein related to the regulation of viral genome transcription. E1A protein encoded by the E1A gene of adenovirus activates the transcription of a group of genes (e.g., E1B, E2, E4) required for infectious virus production. E1B protein encoded by the E1B gene of adenovirus assists late gene (L gene) mRNAs to accumulate into the cytoplasm of infected host cells and inhibits protein synthesis in the host cells, thereby facilitating virus replication. The nucleotide sequences of the E1A and E1B genes are shown in SEQ ID NO: 2 and SEQ ID NO: 3, respectively. In addition to the sequences shown in SEQ ID NO: 2 and SEQ ID NO: 3, the nucleotide sequences of the E1A and E1B genes include nucleotide sequences which are hybridizable under stringent conditions with DNA consisting of a nucleotide sequence complementary to DNA consisting of SEQ ID NO: 2 or SEQ ID NO: 3 and which encode a protein having E1A or E1B activity. Procedures and stringent conditions for hybridization are the same as those described above for the hTERT promoter.

In a preferred embodiment of the invention, the E1A gene comprises the nucleotide sequence of SEQ ID NO: 2 or a variant thereof. The variant of E1A gene comprises the nucleotide sequence having at least 90%, preferably at least 95%, more preferably at least 96%, and even more preferably at least 97%, 98%, or 99% identity to that of SEQ ID NO: 2, wherein the nucleotide sequence encodes a polypeptide having an E1A activity.

In a preferred embodiment of the invention, the E1B gene comprises the nucleotide sequence of SEQ ID NO: 3 or a variant thereof. The variant of E1B gene comprises the nucleotide sequence having at least 90%, preferably at least 95%, more preferably at least 96%, and even more preferably at least 97%, 98%, or 99% identity to that of SEQ ID NO: 3, wherein the nucleotide sequence encodes a polypeptide having an E1B activity.

Identity of any two nucleotide sequences can be determined by those skilled in the art based, for example, on a BLAST 2.0 computer alignment. BLAST 2.0 searching is known in the art and is publicly available, for example, at ncbi.nlm.nih.gov/BLAST/.

IRES (internal ribosome entry site) sequence is a protein synthesis initiation signal specific to the picornavirus family and is considered to serve as a ribosomal binding site because of having a sequence complementary to the 3'-terminal end of 18S ribosomal RNA. It is known that translation of mRNAs derived from viruses of the picornavirus family is mediated by this sequence. The efficiency of translation from the IRES sequence is high and protein synthesis occurs even from the middle of mRNA in a manner not dependent on the cap structure. Thus, in the virus of the present invention, the E1A gene and the E1B gene, which is located downstream of the IRES sequence, are both translated independently by the action of hTERT promoter. With the use of the IRES sequence, hTERT promoter-mediated expression regulation occurs independently in both the E1A gene and the E1B gene, and hence virus growth can be more strictly limited to cells having telomerase activity when compared to the case where any one of the E1A gene or the E1B gene is regulated by the hTERT promoter. Moreover, the IRES sequence inserted between the E1A gene and the E1B gene can increase the growth capacity of the virus in host cells. The nucleotide sequence of the IRES sequence is shown in SEQ ID NO: 4. In addition to the sequence shown in SEQ ID NO: 4, the nucleotide sequence of the IRES sequence includes nucleotide sequences which are hybridizable under stringent conditions with DNA consisting of a nucleotide sequence complementary to DNA consisting of SEQ ID NO: 4 and which encode a protein having IRES activity. Procedures and stringent conditions for hybridization are the same as those described above for the hTERT promoter.

In a preferred embodiment of the invention, the IRES sequence comprises the nucleotide sequence of SEQ ID NO: 4 or a variant thereof. The variant of the IRES sequence comprises the nucleotide sequence having at least 90%, preferably at least 95%, more preferably at least 96%, and even more preferably at least 97%, 98%, or 99% identity to that of SEQ ID NO: 4, wherein the nucleotide sequence has an IRES activity.

miRNA generally refers to short single-stranded RNA of approximately 15 to 25 nucleotides and is considered to regulate the translation of various genes upon binding to its target sequence present in mRNA. Thus, for example, when miRNA-expressing cells are infected with a recombinant adenovirus comprising a desired gene and a target sequence of the miRNA, the desired gene is prevented from being expressed in these cells. Such a target sequence of miRNA may be inserted into any site as long as a desired gene is prevented from being expressed, but it preferably inserted into an untranslated region of the desired gene, more preferably downstream of the desired gene.

The target sequence of miRNA to be used in the present invention includes target sequences of miRNAs which are expressed in non-cancer cells. Non-cancer cells are intended to mean cells that are not malignant tumor cells, and examples include normal cells, benign tumor cells and so on. Normal cells include, for example, normal blood cells, normal endothelial cells, normal fibroblasts, normal stem cells and so on. On the other hand, circulating tumor cells are regarded as cells originating from malignant tumors, and hence they fall within malignant tumor cells in the present invention.

The target sequence of miRNA to be used in the present invention also includes target sequences of miRNAs which are expressed specifically in blood cells. In the present invention, "blood cells" may include not only normal blood cells, but also cancerous blood cells. Namely, in the present invention. "miRNA which is expressed specifically in blood cells" may be expressed specifically in normal blood cells or may be expressed specifically in both normal blood cells and cancerous blood cells. Even when expressed specifically in both normal blood cells and cancerous blood cells, miRNA can also reduce false positive cases of normal blood cells during detection of circulating tumor cells and thereby ensures accurate detection of circulating tumor cells released from solid cancers. In the present invention, "miRNA which is expressed specifically in blood cells" is more preferably miRNA which is expressed in normal blood cells but is not expressed in cancerous blood cells.

In the present invention, blood cells include, but are not limited to, leukocytes (i.e., neutrophils, eosinophils, basophils, lymphocytes (T cells and B cells), monocytes, dendritic cells), CD34-positive cells, hematopoietic cells, hematopoietic stem cells, hematopoietic progenitor cells, peripheral blood mononuclear cells (PBMCs) and so on. Likewise, cancerous blood cells include leukemia cells, lymphoma cells and so on. In the present invention, being "expressed specifically" in certain cells is intended to mean not only that expression is limited only to the intended cells, but also that expression levels are higher in the intended cells than in other cells. For example, being "expressed specifically in blood cells" is intended to mean not only that expression is limited only to blood cells, but also that expression levels are higher in blood cells than in any cells other than blood cells.

miRNA which is expressed specifically in blood cells includes, for example, miR-142, miR-15, miR-16, miR-21, miR-126, miR-181, miR-223, miR-296 and so on, with miR-142, miR-15 and miR-16 being preferred.

Although miRNA is single-stranded RNA, it is possible to use a target sequence of either strand of premature double-stranded RNA as long as a desired gene can be prevented from being expressed. For example, there are miR-142-3p and miR-142-5p for miR-142, and a target sequence of either miRNA may be used in the present invention. Namely, in the present invention, "miR-142" includes both miR-142-3p and miR-142-5p, with miR-142-3p being preferred. Likewise, in the present invention. "miR-15" includes the sense strand (referred to as "miR-15S") and antisense strand (referred to as "miR-15AS") of premature double-stranded RNA. The same applies to other miRNAs.

miR-142-3p gene is located at a site where translocation occurs in B cell leukemia (aggressive B cell leukemia), and is known to be expressed in hematopoietic tissues (e.g., bone marrow, spleen, thymus), but not expressed in other tissues. Moreover, miR-142-3p has been observed to be expressed in mouse fetal liver (fetal hematopoietic tissue) and hence is considered to be involved in differentiation of the hematopoietic system (Chang-Zheng Chen, et al., Science, 2004).

In this embodiment, gene expression is regulated in two stages in a selective manner, because specific gene expression is caused in cancer cells by the action of hTERT promoter and gene expression in blood cells is regulated by the action of miRNA.

In another embodiment, the target sequence of miRNA to be used in the present invention includes a target sequence of miRNA whose expression is suppressed in cancer cells. miRNA whose expression is suppressed in cancer cells includes, for example, miR-125, miR-143, miR-145, miR-199, let-7 and so on. In this embodiment, specific gene expression in cancer cells is doubly regulated by the action of hTERT promoter and miRNA.

Although miRNA molecules have been initially found in nematodes, yeast and other organisms, there are currently found several hundreds of miRNAs in humans and mice. The sequences of these miRNAs are known, and sequence information and so on can be obtained by access to public DBs (e.g., miR Base: the microRNA database (world wide web.mirbase.org), microRNA.org—Targets and Expression (world wide web.microrna.org/microrna/home.do)).

The sequences of miR-142, miRNA-15, miRNA-16, miR-21, miR-126, miR-181, miR-223, miR-296, miR-125, miR-143, miR-145, miR-199 and let-7 are shown below.

```
miR-142-3p:
                                            (SEQ ID NO: 5)
5'-UGUAGUGUUUCCUACUUUAUGGA miR-142-5p:
                                            (SEQ ID NO: 6)
5'-CAUAAAGUAGAAAGCACUACU miR-15S:
                                            (SEQ ID NO: 7)
5'-UAGCAGCACAUAAUGGUUUGUG miR-15AS:
                                            (SEQ ID NO: 8)
5'-CAGGCCAUAUUGUGCUGCCUCA
```

-continued miR-16S:
(SEQ ID NO: 9)
5'-UAGCAGCACGUAAAUAUUGGCG miR-16AS:
(SEQ ID NO: 10)
5'-CCAGUAUUAACUGUGCUGCUGA miR-21S:
(SEQ ID NO: 11)
5'-UAGCUUAUCAGACUGAUGUUGA miR-21AS:
(SEQ ID NO: 12)
5'-CAACACCAGUCGAUGGGCUGU miR-126S:
(SEQ ID NO: 13)
5'-UCGUACCGUGAGUAAUAAUGCG miR-126AS:
(SEQ ID NO: 14)
5'-CAUUAUUACUUUUGGUACGCG miR-181:
(SEQ ID NO: 15)
5'-AACAUUCAACGCUGUCGGUGAGU miR-223S:
(SEQ ID NO: 16)
5'-UGUCAGUUUGUCAAAUACCCCA rniR-223AS:
(SEQ ID NO: 17)
5'-CGUGUAUUUGACAAGCUGAGUU miR-296-3p:
(SEQ ID NO: 18)
5'-GAGGGUUGGGUGGAGGCUCUCC miR-296-5p:
(SEQ ID NO: 19)
5'-AGGGCCCCCCCUCAAUCCUGU miR-125:
(SEQ ID NO: 20)
5'-UCCCUGAGACCCUUUAACCUGUGA miR-143S:
(SEQ ID NO: 21)
5'-UGAGAUGAAGCACUGUAGCUC miR-143AS:
(SEQ ID NO: 22)
5'-GGUGCAGUGCUGCAUCUCUGGU miR-145S:
(SEQ ID NO: 23)
5'-GUCCAGUUUUCCCAGGAAUCCCU miR-145AS
(SEQ ID NO: 24)
5'-GGAUUCCUGGAAAUACUGUUCU miR-199:
(SEQ ID NO: 25)
5'-CCCAGUGUUCAGACUACCUGUUC let-7:
(SEQ ID NO: 26)
5'-UGAGGUAGUAGGUUGUAUAGUU In the present invention, a single unit of a target sequence of miRNA is composed of a sequence complementary to the whole or part of the miRNA, and has a nucleotide length of 7 to 30 nucleotides, preferably 19 to 25 nucleotides, more preferably 21 to 23 nucleotides. In the present invention, a single unit of a target sequence of miRNA is intended to mean a nucleotide sequence having the minimum length required for serving as a target of certain miRNA. More specifically, it is intended to mean an oligonucleotide of at least 7 nucleotides in length selected from complementary sequences of the nucleotide sequences shown in SEQ ID NOs: 5 to 26, and such an oligonucleotide may comprise substitution, deletion, addition or removal of one or several nucleotides at any site(s).

The target sequence as a whole to be integrated into the polynucleotide or recombinant adenovirus of the present invention may comprise several copies of a single unit of target sequence in order to ensure effective interaction between miRNA and the target sequence. The target sequence as a whole to be integrated into the recombinant adenovirus may be of any length as long as it can be integrated into the viral genome. For example, it may comprise 1 to 10 copies, preferably 2 to 6 copies, and more preferably 2 or 4 copies of a single unit of target sequence (John G. Doench, et al., Genes Dev. 2003 17:438-442). An oligonucleotide of appropriate length may be inserted between single units of target sequence contained in the target sequence as a whole. The length of such an oligonucleotide of appropriate length is not limited in any way as long as the target sequence as a whole can be integrated into the recombinant adenovirus genome. For example, such an oligonucleotide may be of 0 to 8 nucleotides in length. Moreover, in the case of comprising several units of a target sequence of miRNA, the target sequences in the respective units may be those toward the same miRNA or those toward different miRNAs. Furthermore, in the case of comprising target sequences toward the same miRNA, the target sequences in the respective units may have different lengths and/or different nucleotide sequences.

The target sequence of miRNA to be contained in the polynucleotide of the present invention (or a replication cassette comprising the same) can also be referred to as a "target sequence of a first microRNA" in order that the polynucleotide, when integrated into the recombinant adenovirus, should be distinguished from other miRNA target sequences present in the recombinant adenovirus.

When miR-142-3p is used as miRNA in the present invention, a target sequence thereof may be exemplified by sequences comprising the following sequences, by way of example.

(i) Sequence comprising two units of a target sequence of miR-142-3p:

(SEQ ID NO: 27)
5'-gcggcctccataaagtaggaaacactacacagctccataaagtagga
aacactacattataagcggtac, each underline represents a single unit of a target sequence of miR-142-3p)

(ii)-1. Sequence comprising four units of a target sequence of miR-142-3p:

(SEQ ID NO: 28)
5'-ggcctccataaagtaggaaacactacacagctccataaagtaggaaa
cactacattaattccataaagtaggaaacactacaccactccataaagta
ggaaacactacagtac, each underline represents a single unit of a target sequence of miR-142-3p)

(ii)-2. Sequence comprising four units of a target sequence of miR-142-3p:

(SEQ ID NO: 55)
5'-tccataaagtaggaaacactacacagctccataaagtaggaaacact
acattaattccataaagtaggaaacactacaccactccataaagtaggaa
acactaca, each underline represents a single unit of a target sequence of miR-142-3p)

The nucleotide sequence of SEQ ID NO: 55 corresponds to the sequence from position 5 to 109 in the nucleotide sequence of SEQ ID NO: 28.

(ii)-3. Sequence comprising four units of a target sequence of miR-142-3p:

(SEQ ID NO: 52)
5'-<u>tccataagtaggaaacactacac</u>agc<u>tccataagtacgaaacactac</u>
attaat<u>tccataaagtaggaaacactac</u>agga<u>ctccataaagtaggaaac
actaca</u>-3', each underline represents a single unit of a target sequence of miR-142-3p)

In a preferred embodiment of the invention, the sequence comprising four units of a target sequence of miR-142-3p comprises the nucleotide sequence of SEQ ID NO: 52 or 55, or a variant thereof. The variant of the sequence comprising four units of a target sequence of miR-142-3p comprises the nucleotide sequence having at least 90/%, preferably at least 95%, more preferably at least 96%, and even more preferably at least 97%, 98%, or 99% identity to that of SEQ ID NO: 52 or 55.

The nucleotide sequence of SEQ ID NO: 55 has 98.1% (103/105) identity to the nucleotide sequence of SEQ ID NO: 52. The nucleotide sequence of SEQ ID NO: 52 has 98.1% identity to the nucleotide sequence of SEQ ID NO: 55. That is, the nucleotide sequences of SEQ ID NOs: 52 and 55 have 98.1% (103/105) nucleotide identity each other.

In the present invention, a target sequence of miRNA is placed downstream of the construct of hTERT promoter-E1A gene-IRES sequence-E1B gene, and the resulting polynucleotide comprising the hTERT promoter, the E1A gene, the IRES sequence, the E1B gene and the target sequence of miRNA in this order (which polynucleotide is referred to as a replication cassette) is integrated into the adenovirus genome, whereby E1 gene expression and virus growth can be prevented in cells expressing the miRNA.

In the present invention, a target sequence of miRNA is integrated downstream of the E1B gene or the reporter gene described later, whereby a gene located upstream thereof is prevented from being expressed. Although the details of this mechanism are not clear, a possible mechanism is as follows. First, miRNA-RISC (RNA-induced silencing complex) cleaves a target sequence on mRNA to thereby remove polyA from the mRNA. This would reduce the stability of the mRNA to cause degradation of the mRNA and hence prevention of gene expression. Alternatively, miRNA-RISC would recruit polyA ribonuclease, as in the case of normal miRNA, to cause polyA degradation, as a result of which the stability of mRNA would be reduced and gene expression would be prevented.

It should be noted that there are previous reports showing that the miRNA-induced inhibitory effect against gene expression was not obtained for the expression (translation) of a gene inserted downstream of the IRES sequence (Ramesh S. Pillai et al., Science 309, 1573(2005): Geraldine Mathonnet, et al., Science 317, 1764 (2007)). However, when the inventors of the present invention confirmed gene expression for the recombinant adenovirus of the present invention comprising hTERT promoter, E1A gene, IRES sequence, E1B gene and a target sequence of miRNA in this order, the miRNA was found to sufficiently prevent the expression of the E1B gene inserted downstream of the IRES sequence. This is a new finding in the present invention.

The genes to be contained in the replication cassette of the present invention can be obtained by standard genetic engineering techniques. For example, it is possible to use nucleic acid synthesis with a DNA synthesizer, which is commonly used as a genetic engineering technique. Alternatively, it is also possible to use PCR techniques in which gene sequences serving as templates are isolated or synthesized, and primers specific to each gene are then designed to amplify the gene sequence with a PCR system (Current Protocols in Molecular Biology, John Wiley & Sons (1987) Section 6.1-6.4) or gene amplification techniques using a cloning vector. The above techniques can be easily accomplished by those skilled in the art in accordance with Molecular cloning $2^{nd}$ Edt. Cold Spring Harbor Laboratory Press (1989), etc. For purification of the resulting PCR product, known techniques can be used. If necessary, conventionally used sequencing techniques may be used to confirm whether the intended gene has been obtained, as expected. For example, dideoxynucleotide chain termination sequencing (Sanger et al. (1977) Proc. Natl. Acad. Sci. USA 74: 5463) or the like may be used for this purpose. Alternatively, an appropriate DNA sequencer (e.g., ABI PRISM (Applied Biosystems)) may also be used for sequence analysis.

In the present invention, the target sequence of miRNA can be obtained by being designed and synthesized such that each single unit of target sequence is complementary to the whole or part of the nucleotide sequence of the miRNA. For example, a target sequence of miR-142-3p can be obtained by synthesizing DNA such that it is complementary to the nucleotide sequence of miR-142-3p.

Then, the respective genes obtained as above are ligated in a given order. First, the above genes are each cleaved with known restriction enzymes or the like, and the cleaved DNA fragment of each gene is inserted into and ligated to a known vector in accordance with known procedures. As a known vector, pIRES vector may be used, by way of example. The pIRES vector comprises the IRES (internal ribosome entry site) sequence of encephalonmyocarditis virus (ECMV) and is capable of translating two open reading frames (ORFs) from one mRNA. With the use of the pIRES vector, it is possible to prepare a "polynucleotide which comprises hTERT promoter, E1A gene. IRES sequence and E1B gene in this order and which comprises a target sequence of microRNA" by sequentially inserting the required genes into a multicloning site. Such a target sequence of miRNA may be inserted into any site, but it is preferably inserted downstream of the hTERT promoter-E1A-IRES-E1B construct. For DNA ligation, DNA ligase may be used. Alternatively, CMV promoter contained in a known vector (e.g., pShuttle) may be removed with known restriction enzymes and a sequence cleaved from the hTERT promoter-E1A-IRES-E1B-miRNA target sequence with appropriate restriction enzymes may then be inserted into this site, if necessary. Once the E1 gene required for adenovirus growth is allowed to be expressed under the control of the hTERT promoter, the virus can be grown specifically in cancer cells.

In a preferred embodiment of the invention, hTERT promoter and E1A gene, E1A and IRES sequence. IRES sequence and E1B gene, and E1B gene and miRNA target sequence may be linked by spacer sequences.

In another preferred embodiment of the invention, the replication cassette comprises the nucleotide sequence of SEQ ID NO: 53 or a variant thereof. The variant of the polynucleotide cassette comprises the nucleotide sequence having at least 90%, preferably at least 95%, more preferably at least 96%, and even more preferably at least 97%, 98%, or 99% identity to that of SEQ ID NO: 53, wherein the nucleotide sequence encodes a polypeptide having an activity to enable an adenovirus to replicate selectively in tumor cells. The activity can be determined by infecting the adenovirus comprising the replication cassette to tumor cells and measuring viral titer of the adenovirus.

(2) Labeling Cassette

In yet another embodiment, the present invention relates to a recombinant adenovirus in which the above replication cassette is integrated into the E1 region of the adenovirus genome and a labeling cassette is further integrated into the E3 region of the adenovirus genome. Such a labeling cassette comprises a reporter gene and a promoter capable of regulating the expression of the gene, and may further comprise a target sequence of miRNA.

The adenovirus E3 region contains 11.6 kDa ADP (adenovirus death protein), and ADP has the function of promoting cell damage and virus diffusion. The recombinant adenovirus of the present invention is designed to eliminate any viral genome region like the E3 region containing ADP, which encodes a protein having the function of promoting cell damage and virus diffusion, so that the timing of cell death is delayed to facilitate identification of cancer tissues by production (emission, expression) of fluorescence (e.g., GFP). This is also effective in that circulating tumor cells (CTCs) described later can be detected alive over a long period of time.

The reporter gene to be contained in the labeling cassette in the recombinant adenovirus of the present invention is not limited in any way, and examples include a gene encoding a protein which emits fluorescence, a gene encoding an enzyme protein which generates a luminophore or a chromophore upon enzymatic reaction, a gene encoding an antibiotic, a gene encoding a tag-fused protein, a gene encoding a protein which is expressed on the cell surface and binds to a specific antibody, a gene encoding a membrane transport protein, and so on. Examples of a protein which emits fluorescence (i.e., a labeling protein) include a green fluorescent protein (GFP) derived from luminous jellyfish such as *Aequorea victorea*, its variants EGFP (enhanced-humanized GFP) and rsGFP (red-shift GFP), a yellow fluorescent protein (YFP), a cyan fluorescent protein (CFP), a blue fluorescent protein (BFP). GFP derived from *Renilla reniformis* and so on, and genes encoding these proteins can be used in the present invention. The above protein which emits fluorescence is preferably GFP or EGFP.

Likewise, examples of an enzyme protein which generates a luminophore or a chromophore upon enzymatic reaction include β-galactosidase, luciferase and so on. β-Galactosidase generates a blue chromophore from 5-bromo-4-chloro-3-indolyl-β-D-galactopyranoside (X-gal) upon enzymatic reaction. On the other hand, luciferase generates a luminophore upon enzymatic reaction with luciferin. Firefly luciferase, bacterial luciferase, *Renilla* luciferase and so on are known as members of luciferase, and those skilled in the art would be able to select an appropriate enzyme from known luciferase members.

Moreover, the promoter capable of regulating the expression of the above gene is not limited in any way as long as it is a suitable promoter compatible with the virus used for the expression of the above desired gene. Examples include, but are not limited to, CMV promoter, hTERT promoter, SV40 late promoter, MMTV LTR promoter, RSV LTR promoter, SRα promoter, β-actin promoter, PGK promoter, EF-1a promoter and so on. Preferably, CMV promoter or hTERT promoter can be used for this purpose.

The target sequence of miRNA to be integrated into the labeling cassette may be either the same or different from the target sequence of miRNA to be integrated into the replication cassette.

In the present invention, the target sequence of miRNA is placed within the untranslated region of the reporter gene, preferably downstream of this gene, whereby the reporter gene can be prevented from being expressed. Namely, in the present invention, the labeling cassette preferably comprises a promoter capable of regulating the reporter gene, the reporter gene and the target sequence of microRNA in this order. The target sequence of miRNA to be integrated into the labeling cassette is referred to as a "target sequence of a second microRNA" in order that it should be distinguished from the target sequence of miRNA to be contained in the replication cassette. Other explanations on miRNA are the same as described above.

In a preferred embodiment of the invention, the labeling cassette preferably comprises the sequence comprising four units of a target sequence of miR-142-3p. The sequence comprises the nucleotide sequence of SEQ ID NO: 52 or 55, or a variant thereof. The variant of the sequence comprising four units of a target sequence of miR-142-3p comprises the nucleotide sequence having at least 90%, preferably at least 95%, more preferably at least 96%, and even more preferably at least 97%, 98%, or 99% identity to that of SEQ ID NO: 52 or 55.

In a preferred embodiment of the invention, examples of a replication cassette include a replication cassette comprising CMV promoter, EGFP gene and a target sequence of miR-142p. In a preferred embodiment of the invention, the replication cassette comprising CMV promoter, EGFP gene and a target sequence of miR-142p comprises the nucleotide sequence of SEQ ID NO: 54 or a variant thereof. The variant of the polynucleotide cassette comprises the nucleotide sequence having at least 90%, preferably at least 95%, more preferably at least 96%, and even more preferably at least 97%, 98%, or 99% identity to that of SEQ ID NO: 54.

Details on how to obtain, purify and sequence the recombinant genes to be contained in the labeling cassette of the present invention are the same as described above for the replication cassette.

(3) Cell Death-Inducing Cassette

In yet another embodiment, the present invention relates to a recombinant adenovirus in which the above replication cassette is integrated into the E1 region of the adenovirus genome and a cell death-inducing cassette is integrated into the E3 region of the adenovirus genome. Such a cell death-inducing cassette comprises a gene encoding a cell death induction-related protein and a promoter capable of regulating the expression of the gene, and may further comprise a target sequence of microRNA.

The cell death-inducing cassette used in the recombinant adenovirus of the present invention comprises a gene encoding a cell death induction-related protein and a promoter capable of regulating the expression of the gene. Thus, for example, when the recombinant adenovirus of the present invention is infected into cancer cells, the virus grows specifically in the cancer cells to thereby increase the intracellular expression level of the cell death induction-related protein and induce cell death only in the cancer cells without damaging other normal cells.

Such a gene encoding a cell death induction-related protein is intended to mean a gene encoding a protein related to the induction of cell death in specific cells. Examples of a cell death induction-related protein include immunological proteins such as PA28. PA28 is a protein which activates intracellular proteasomes and which elicits immune reactions and also induces cell death when overexpressed. Moreover. TRAIL can also be exemplified as an apoptosis-inducing protein. TRAIL refers to a molecule which induces apoptotic cell death upon binding to its receptor on the cell surface.

Moreover, another example of the gene encoding a cell death induction-related protein is a tumor suppressor gene, which has the function of suppressing the growth of cancer cells. Examples of such a tumor suppressor gene include the following genes used in conventional gene therapy. SEQ ID NO (nucleotide sequence) and GenBank Accession No. are shown below for each gene.

p53 (SEQ ID NO: 29: Accession No. M14694): multiple types of cancer p15 (SEQ ID NO: 30: Accession No. L36844): multiple types of cancer p16 (SEQ ID NO: 31; Accession No. L27211): multiple types of cancer APC (SEQ ID NO: 32; Accession No. M74088): colorectal cancer, gastric cancer, pancreatic cancer BRCA-1 (SEQ ID NO: 33; Accession No. U14680): ovarian cancer, breast cancer DPC-4 (SEQ ID NO: 34: Accession No. U44378): colorectal cancer, pancreatic cancer FHIT (SEQ ID NO: 35: Accession No. NM 112012): gastric cancer, lung cancer, uterine cancer p73 (SEQ ID NO: 36: Accession No. Y11416): neuroblastoma PATCHED (SEQ ID NO: 37; Accession No. U59464): basal cell carcinoma Rbp1110 (SEQ ID NO: 38; Accession No. M15400): lung cancer, osteosarcoma DCC (SEQ ID NO: 39; Accession No. X76132): colorectal cancer NF1 (SEQ ID NO: 40; Accession No. NM 000267): neurofibroma type 1

NF2 (SEQ ID NO: 41: Accession No. L11353): neurofibroma type 2

WT-1 (SEQ ID NO: 42; Accession No. NM 000378): Wilms tumor

The target sequence of miRNA to be contained in the cell death-inducing cassette may be either the same or different from the target sequence of miRNA to be integrated into the replication cassette. In the present invention, the target sequence of miRNA is placed within the untranslated region of the gene encoding a cell death induction-related protein, preferably downstream of this gene, whereby the cell death induction-related protein can be prevented from being expressed. Namely, in the present invention, the cell death-inducing cassette preferably comprises a promoter capable of regulating the gene encoding a cell death induction-related protein, the gene encoding a cell death induction-related protein and the target sequence of microRNA in this order. Other explanations on miRNA are the same as described above.

Details on how to obtain, purify and sequence the recombinant genes to be contained in the cell death-inducing cassette of the present invention are the same as described above for the replication cassette.

To determine whether or not cell death has been induced, morphological observation described below may be conducted for this purpose. Namely, once cells adhered onto the bottom surface of a culture vessel have been infected with the recombinant virus of the present invention and incubated for a given period, the cells will be rounded and detached from the bottom surface and then will float as shiny cells in the culture solution, as observed under an inverted microscope. At this stage, the cells have lost their vital mechanism and hence a determination can be made that cell death has been induced. Alternatively, cell death can also be confirmed with a commercially available kit for living cell assay which uses a tetrazolium salt (e.g., MTT, XTT).

(4) CD46-Binding Fiber Protein

In yet another embodiment, the recombinant adenovirus of the present invention may comprise a gene encoding a CD46-binding adenovirus fiber protein.

Adenovirus vectors which are now commonly used are prepared structurally based on adenovirus type 5 (or type 2) belonging to Subgroup C among 51 serotypes of human adenovirus. Although adenovirus type 5 is widely used because of its excellent gene transfer properties, adenovirus of this type has a problem of being difficult to infect cells with low expression of coxsackievirus and adenovirus receptor (CAR) because its infection is mediated by binding to CAR on target cells. In particular, CAR expression is reduced in highly malignant cancer cells which are highly invasive, metastatic and proliferative, and hence an adenovirus having the fiber protein of adenovirus type 5 may not infect such highly malignant cancer cells.

In contrast, CD46 is expressed on almost all cells except for erythrocytes in humans and is also expressed on highly malignant cancer cells. Thus, a recombinant adenovirus comprising a gene encoding a CD46-binding adenovirus fiber protein can also infect CAR-negative and highly malignant cancer cells. For example, adenovirus types 34 and 35 bind to CD46 as their receptor and thereby infect cells (Marko Marttila, et al., J. Virol. 2005, 79(22):14429-36). As described above, CD46 is expressed on almost all cells except for erythrocytes in humans, and hence adenovirus types 34 and 35 are able to infect a wide range of cells including CAR-negative cells. Moreover, the fiber of adenovirus consists of a knob region, a shaft region and a tail region, and adenovirus infects cells through binding of its fiber knob region to the receptor. Thus, at least the fiber knob region in the fiber protein is replaced from adenovirus type 5 origin to adenovirus type 34 or 35 origin, % hereby the virus will be able to infect CAR-negative cells via CD46.

Because of comprising a gene encoding a CD46-binding adenovirus fiber protein, the recombinant adenovirus of the present invention is able to infect almost all cells except for erythrocytes and thus able to infect highly malignant CAR-negative cancer cells which are highly invasive, metastatic and proliferative. In the present invention, "CAR-negative" cells are intended to mean cells where CAR expression is low or cells where CAR is not expressed at all.

57 serotypes have now been identified for human adenovirus, and these serotypes are classified into six groups, i.e., Groups A to F. Among them, adenovirus types belonging to Group B have been reported to bind to CD46. Adenovirus types belonging to Group B include adenovirus types 34 and 35, as well as adenovirus types 3, 7, 11, 16, 21 and 50, by way of example.

For use as a CD46-binding adenovirus fiber protein in the present invention, preferred is the fiber protein of adenovirus belonging to Group B, more preferred is the fiber protein of adenovirus type 3, 7, 34, 35, 11, 16, 21 or 50, and even more preferred is the fiber protein of adenovirus type 34 or 35.

The nucleotide sequence of a gene encoding the fiber protein of adenovirus type 34, 35, 3, 7, 11, 16, 21 or 50 is available from a known gene information database. e.g., the GenBank of NCBI (The National Center for Biotechnology Information). Moreover, in the present invention, the nucleotide sequence of a gene encoding the fiber protein of adenovirus type 34, 35, 3, 7, 11, 16, 21 or 50 includes not only the nucleotide sequence of each gene available from a database as described above, but also nucleotide sequences which are hybridizable under stringent conditions with DNA consisting of a nucleotide sequence complementary to DNA consisting of each nucleotide sequence available from a database and which encode a protein with binding activity to CD46.

The binding activity to CD46 can be evaluated when a recombinant adenovirus having DNA comprising the nucleotide sequence is measured for its infectivity to CD46-expressing cells. The infectivity of such a recombinant adenovirus may be measured in a known manner, for example, by detecting GFP expressed by the virus infected into CD46-expressing cells under a fluorescence microscope or by flow cytometry, etc. Procedures and stringent conditions for hybridization are the same as described above.

The recombinant adenovirus of the present invention may comprise the entire or partial region of a CD46-binding adenovirus fiber protein, such that at least the fiber knob region in the fiber protein binds to CD46. Namely, in the present invention, the CD46-binding adenovirus fiber protein may comprise at least the fiber knob region in the fiber protein of adenovirus belonging to Group B, more preferably at least the fiber knob region in the fiber protein of adenovirus of any type selected from the group consisting of type 34, type 35, type 3, type 7, type 11, type 16, type 21 and type 50, and even more preferably at least the fiber knob region in the fiber protein of adenovirus type 34 or 35. Moreover, the technical idea of the present invention is not limited to these fiber proteins as long as the intended protein binds to CD46, and it also covers various proteins capable of binding to CD46 as well as proteins having a motif capable of binding to CD46.

Alternatively, in the present invention, the CD46-binding fiber protein may comprise a region consisting of the fiber knob region and the fiber shaft region in the fiber protein of adenovirus belonging to Group B, more preferably a region consisting of the fiber knob region and the fiber shaft region in the fiber protein of adenovirus of any type selected from the group consisting of type 34, type 35, type 3, type 7, type 11, type 16, type 21 and type 50, and even more preferably a region consisting of the fiber knob region and the fiber shaft region in the fiber protein of adenovirus type 34 or 35.

In the present invention, the CD46-binding fiber protein may comprise the fiber shaft region or the fiber tail region in the fiber protein of adenovirus of any type (e.g., type 2, type 5) other than the above types, as long as it comprises at least the fiber knob region in the fiber protein of adenovirus belonging to Group B.

Examples of such a fiber protein include, but are not limited to, fiber proteins which comprise a region consisting of not only the fiber knob region and the fiber shaft region in the fiber protein of adenovirus of any type selected from the group consisting of type 34, type 35, type 3, type 7, type 11, type 16, type 21 and type 50, but also the fiber tail region in the fiber protein of adenovirus type 5.

The nucleotide sequences of a gene encoding the fiber knob region in the fiber protein of adenovirus type 34, a gene encoding the fiber shaft region in the fiber protein of adenovirus type 34 and a gene encoding a region consisting of the fiber knob region and the fiber shaft region in the fiber protein of adenovirus type 34 are shown in SEQ ID NOs: 47, 48 and 49, respectively.

Likewise, the nucleotide sequence of a gene encoding a region consisting of not only the fiber knob region and the fiber shaft region in the fiber protein of adenovirus type 34, but also the fiber tail region in the fiber protein of adenovirus type 5 is shown in SEQ ID NO: 50. In the present invention, the nucleotide sequence of such a gene includes not only the nucleotide sequence shown in SEQ ID NO: 50, but also nucleotide sequences which are hybridizable under stringent conditions with DNA consisting of a nucleotide sequence complementary to DNA consisting of the nucleotide sequence shown in SEQ ID NO: 50 and which encode a protein with binding activity to CD46. Procedures for evaluation of the binding activity to CD46, procedures and stringent conditions for hybridization are the same as described above.

In a preferred embodiment of the invention, the gene encoding a CD46-binding adenovirus fiber protein comprises the nucleotide sequence of SEQ ID NO: 50 or a variant thereof. The variant of the gene encoding a CD46-binding adenovirus fiber protein comprises the nucleotide sequence having at least 90%, preferably at least 95%, more preferably at least 96%, and even more preferably at least 97%, 98%, or 99% identity to the nucleotide sequence of SEQ ID NO: 50.

To prepare the recombinant adenovirus of the present invention, a polynucleotide comprising the replication cassette, the labeling cassette and/or the cell death-inducing cassette may be excised with appropriate restriction enzymes and inserted into an appropriate virus expression vector. A preferred virus expression vector is an adenovirus vector, more preferably an adenovirus type 5 vector, and particularly preferably an adenovirus type 5 vector which comprises a gene encoding a CD46-binding adenovirus fiber protein (e.g., the fiber protein of adenovirus type 34 or 35).

As shown in Example 2 described later, GFP expression in blood cells was sufficiently suppressed in both cases where a miRNA target sequence was inserted downstream of the replication cassette and where a miRNA target sequence was inserted downstream of the labeling cassette, whereas GFP expression in blood cells was unexpectedly significantly suppressed in a case where miRNA target sequences were simultaneously inserted downstream of the replication cassette and downstream of the labeling cassette, respectively. This is a new finding in the present invention.

In the present invention, the recombinant adenovirus may be obtained in the following manner, by way of example.

First, pHMCMV5 (Mizuguchi H. et al., Human Gene Therapy, 10: 2013-2017, 1999) is treated with restriction enzymes and a target sequence of miRNA is inserted to prepare a vector having the target sequence of miRNA. Next, pSh-hAIB comprising a construct of hTERT promoter-E1A-IRES-E1B (WO2006/036004) is treated with restriction enzymes and the resulting fragment comprising the hTERT promoter-E1A-IRES-E1B construct is inserted into the above vector having the target sequence of miRNA to obtain a vector comprising hTERT promoter-E1A-IRES-E1B-miRNA target sequence. On the other hand, pHMCMVGFP-1 (pHMCMV5 comprising EGFP gene) is treated with restriction enzymes to obtain a fragment comprising CMV promoter and EGFP gene, and this fragment is inserted into the above vector having the target sequence of miRNA to obtain a vector comprising a construct of CMV-EGFP-miRNA target sequence. Then, the vector comprising hTERT promoter-E1A-IRES-E1B-miRNA target sequence and the vector comprising CMV-EGFP-miRNA target sequence are each treated with restriction enzymes and ligated together to obtain a vector in which hTERT promoter-E1A-IRES-E1B-miRNA target sequence is integrated into the E1-deficient region of the adenovirus genome and CMV-EGFP-miRNA target sequence is integrated into the E3-deficient region of the adenovirus genome. Alternatively, when a vector comprising a gene encoding a CD46-binding adenovirus fiber protein is used as a vector to be inserted with the DNA fragments comprising the respective constructs, it is possible to obtain a vector in which hTERT promoter-E1A-IRES-E1B-miRNA target sequence is integrated into the E1-deficient region of the adenovirus genome and CMV-EGFP-miRNA target sequence is integrated into the E3-deficient region of the adenovirus genome and which comprises a gene encoding a CD46-binding adenovirus fiber protein. Moreover, this vector may be linearized with a known restriction enzyme and then transfected into cultured cells (e.g., 293 cells) to thereby prepare an infectious recombinant adenovirus. It should be noted that those skilled in the art would be able to easily prepare all viruses falling within the present invention by making minor modifications to the above preparation procedures.

In a preferred embodiment of the invention, the recombinant adenovirus comprises a nucleotide sequence comprising:

a replication cassette comprising a polynucleotide comprising a human telomerase reverse transcriptase promoter, E1A gene, IRES sequence and E1B gene in this order, and a target sequence of a first microRNA, wherein the first microRNA is miR-142, and wherein the replication cassette is integrated into the E1 region of the adenovirus genome:

a labeling cassette comprising a reporter gene, a promoter capable of regulating the expression of the reporter gene, and a target sequence of a second microRNA, wherein the second microRNA is miR-142, and wherein the labeling cassette is integrated into the E3 region of the adenovirus genome; and a gene encoding a CD46-binding fiber protein comprising at least the fiber knob region in the fiber protein of adenovirus type 34 or 35, which is integrated into the adenovirus genome:

wherein the recombinant adenovirus comprises the nucleotide sequence of SEQ ID NO: 51 or a variant thereof. The variant comprises the nucleotide sequence having at least 90%, preferably at least 95%, more preferably at least 96%, and even more preferably at least 97%, 98%, or 99% identity to the nucleotide sequence of SEQ ID NO: 51.

3. REAGENT FOR CANCER CELL DETECTION OR REAGENT FOR CANCER DIAGNOSIS

As described above, the recombinant adenovirus of the present invention has the following features.
(i) This recombinant adenovirus infects almost all cells except for erythrocytes, and is also able to infect highly malignant CAR-negative cancer cells.
(ii) This recombinant adenovirus grows specifically in hTERT-expressing cancer cells and also increases the expression level of a reporter gene upon growth, whereby the production of a labeling protein, a chromophore or the like can be increased to detectable levels.
(iii) This recombinant adenovirus can prevent the occurrence of false positive results even when the virus infects normal cells having hTERT promoter activity, because miRNA expression prevents not only growth of the virus, but also expression of a reporter gene. In particular, because of comprising a target sequence of miRNA which is expressed specifically in blood cells, this recombinant adenovirus can prevent the occurrence of false positive results even when the virus infects normal blood cells having hTERT promoter activity, because expression of this miRNA prevents not only growth of the virus in blood cells but also expression of a reporter gene.

Thus, the recombinant adenovirus of the present invention can be used as a reagent for cancer cell detection or as a reagent for cancer diagnosis. In particular, because of having the above features, the recombinant virus of the present invention is extremely effective for detection of circulating tumor cells (CTCs) present in blood.

On the other hand, since 2004 when CTCs, which are cancer cells present in blood, were reported to serve as a prognostic factor for post-operative breast cancer patients in the New England Journal of Medicine (Cristofanilli M. et al., The New England Journal of Medicine, 2004, 781-791), CTCs have been measured as a biomarker in many clinical trials conducted in Europe and North America. Particularly in breast cancer, prostate cancer and skin cancer, CTCs have been proven to be an independent factor which determines the prognosis of these cancers. Moreover, in Europe, in the clinical trial in adjuvant setting of prostate cancer (SUCCESS), the number of CTCs counted is added to the inclusion criteria and only patients in whom one or more cells have been detected are included. This trial is a large-scale clinical trial including 2000 cases or more, and attention is being given to the results. Moreover, there is also a clinical trial in which an increase or decrease per se in CTCs is one of the clinical endpoints (MDV3100).

In recent years, the FDA in the United States has issued guidelines for approval and authorization of molecular-targeted anticancer agents, and hence the CTC test has become more important in cancer diagnosis. The guidelines issued by the FDA define that genetic changes in molecular targets in tumors should be tested before selection of molecular-targeted anticancer agents. When attempting to achieve the guidelines by conventional techniques, there arises a need for surgical biopsy from tumor tissues in patients to conduct genetic testing, which will impose a very strong burden on the patients. To solve this problem, efforts are now made to conduct genetic testing on CTCs collected from blood, and this strategy is referred to as "liquid biopsy" in contrast to the conventional "biopsy." Once this strategy has been achieved, genetic testing of tumor tissues can be conducted simply by blood collection and the burden on patients can be reduced greatly. For these reasons, the CTC test is receiving great attention as a highly useful testing technique in the clinical setting.

The CellSearch System of Veridex LLC is the only CTC detection device currently approved by the FDA, and most of the CTC detection methods used in clinical trials are accomplished by this CellSearch System. The CellSearch System is based on techniques to detect cancer cells with EpCAM antibody and cytokeratin antibody.

However, CTC detection techniques are designed to detect several to several tens of cells from among a billion of blood cells, and it is therefore very difficult to improve their sensitivity and accuracy. Thus, some problems are also pointed out in CTC detection methods based on the CellSearch System. For example, it is pointed out that cancer cells which are negative in the CTC test based on the CellSearch System are detected as being positive in another test, and that there are great differences in sensitivity and accuracy, depending on the cancer type (Allard W. J. et al., Clinical Cancer Research, 2004, 6897-6904). Moreover, the CellSearch System is also pointed out to have a problem of low CTC detection rate for lung cancer in the clinical setting (ibid).

Likewise, the CellSearch System is also pointed out to have a problem of reduced CTC detection rate because the expression of cell surface antigens including EpCAM is reduced in cancer cells having undergone epithelial-mesenchymal transition (EMT) (Anieta M. et. al., J Natl Cancer Inst, 101, 2009, 61-66, Janice Lu et. al., Int J Cancer, 126(3), 2010, 669-683).

Further, to conduct the above "liquid biopsy," additional steps are required for concentration and phenotyping or genotyping of CTCs, which require more sensitive and more accurate CTC detection techniques than simply counting the number of CTCs.

In contrast to this, because of having the above features (i) to (iii), the recombinant adenovirus of the present invention allows simple, highly sensitive and highly accurate detection of CTCs in blood without detection of leukocytes and other normal blood cells. Further, the reagent of the present invention allows detection of CTCs alive, so that the source organ of the detected CTCs can be identified upon analyzing surface antigens or the like present on the cell surface of the CTCs. Thus, the recombinant adenovirus of the present invention is useful for CTC detection and cancer diagnosis.

Moreover, the recombinant adenovirus or reagent for cancer cell detection of the present invention can be used to detect cancer cells having undergone EMT or mesenchymal-epithelial transition (MET). EMT is a phenomenon in which cancer cells lose their properties as epithelium and acquire features as mesenchymal lineage cells tending to migrate into surrounding tissues, and EMT is also involved in invasion and/or metastasis of cancer cells. On the other hand, mesenchymal-epithelial transition (MET) is a phenomenon in which mesenchymally derived cells acquire features as epithelium. As described above, it is difficult to detect cancer cells having undergone EMT by known techniques including the CellSerch System. In contrast, the present invention allows detection of cancer cells having undergone EMT or MET. The recombinant adenovirus of the present invention is therefore useful for cancer cell detection and for cancer diagnosis.

Further, the recombinant adenovirus of the present invention can also be used to detect drug-resistant cancer cells. Drugs intended in the present invention are those used for cancer chemotherapy. Examples of such drugs include, but are not limited to, adriamycin, carboplatin, cisplatin, 5-fluorouracil, mitomycin, bleomycin, doxorubicin, daunorubicin, methotrexate, paclitaxel, docetaxel and actinomycin D, etc. Moreover, the recombinant virus of the present invention can also be used to detect cancer stem cells. In the present invention, cancer stem cells refer to cells (stem cells) serving as the origin of cancer cells. Cancer stem cells also include those having drug resistance.

In the present invention, the type of cancer or tumor to be detected or diagnosed is not limited in any way, and cells of all cancer types can be used. Examples include solid cancers or blood tumors, more specifically brain tumor, cervical cancer, esophageal cancer, tongue cancer, lung cancer, breast cancer, pancreatic cancer, gastric cancer, small intestinal cancer, duodenal cancer, colorectal cancer, bladder cancer, kidney cancer, liver cancer, prostate cancer, uterine cancer, uterine cervical cancer, ovarian cancer, thyroid cancer, gallbladder cancer, pharyngeal cancer, sarcoma, melanoma, leukemia, lymphoma and multiple myeloma (MM). Most (85% or more) of the cancer cells derived from human tissues show increased telomerase activity, and the present invention allows detection of such telomerase-expressing cancer cells in general.

Moreover, in the present invention, CTCs are not limited in any way as long as they are cancer cells present in blood, and they include not only cancer cells released from solid cancers, but also blood tumor cells such as leukemia cells and lymphoma cells as mentioned above. However, in cases where CTCs are blood tumor cells, the miRNA target sequence contained in the adenovirus of the present invention is preferably a target sequence of miRNA which is expressed specifically in normal blood cells.

To prepare the reagent of the present invention, the recombinant adenovirus may be treated, e.g., by freezing for easy handling and then used directly or mixed with known pharmaceutically acceptable carriers (e.g., excipients, extenders, binders, lubricants) and/or known additives (including buffering agents, isotonizing agents, chelating agents, coloring agents, preservatives, aromatics, flavorings, sweeteners).

4. METHOD FOR CANCER CELL DETECTION OR METHOD FOR CANCER DIAGNOSIS

Furthermore, the recombinant adenovirus of the present invention can be used for cancer cell detection or cancer diagnosis by contacting the same with cancer cells and detecting the fluorescence or color produced by the cancer cells.

In the present invention, the term "contact(ing)" is intended to mean that cancer cells and the recombinant adenovirus of the present invention are allowed to exist in the same reaction system, for example, by adding the recombinant adenovirus of the present invention to a sample containing cancer cells, by mixing cancer cells with the recombinant adenovirus, by culturing cancer cells in the presence of the recombinant adenovirus, or by infecting the recombinant adenovirus into cancer cells. Moreover, in the present invention, "fluorescence or color" is not limited in any way as long as it is light or color produced from a protein expressed from a reporter gene, and examples include fluorescence emitted from a labeling protein (e.g., GFP), light emitted from a luminophore generated by luciferase-mediated enzymatic reaction, blue color produced from a chromophore generated by enzymatic reaction between β-galactosidase and X-gal, etc.

Cancer cells for use in the method for cancer cell detection or in the method for cancer diagnosis may be derived from a biological sample taken from a subject. Such a biological sample taken from a subject is not limited in any way as long as it is a tissue suspected to contain cancer cells, and examples include blood, tumor tissue, lymphoid tissue and so on. Alternatively, cancer cells may be circulating tumor cells (CTCs) in blood, and explanations on CTCs are the same as described above.

Cancer cell detection and cancer diagnosis using the reagent of the present invention may be accomplished as follows, by way of example.

In cases where the biological sample taken from a subject is blood, the blood sample is treated by addition of an erythrocyte lysis reagent to remove erythrocytes and the remaining cell suspension is mixed in a test tube with the reagent of the present invention at a given ratio (0.01 to 1000 MOI (multiplicity of infection), preferably 0.1 to 100 MOI, more preferably 1 to 10 MOI). The test tube is allowed to stand or rotated for culture at room temperature or 37° C. for a given period of time (e.g., 4 to 96 hours, preferably 12 to 72 hours, more preferably 18 to 36 hours) to facilitate virus infection into cancer cells and virus growth. GFP fluorescence production in the cell fraction is quantitatively analyzed by flow cytometry. Alternatively, GFP-expressing cells are morphologically analyzed by being observed under a fluorescence microscope. This system allows highly sensitive detection of CTCs present in peripheral blood. This method can be used for detection of CTCs which are present in trace amounts in peripheral blood.

In cases where flow cytometry is used for CTC detection, CTCs may be detected by determining whether each cell is GFP-positive or GFP-negative, e.g., in accordance with the following criteria.

First, groups of cells in a sample which is not infected with any virus are analyzed to obtain a background fluorescence value. A threshold is set to the maximum fluorescence value. Subsequently, groups of cells in samples which have been infected with the virus of the present invention are analyzed and groups of cells in a sample showing a fluorescence value equal to or greater than the threshold are determined to be GFP-positive. In the case of using a blood sample taken from a subject, GFP-positive cells can be detected as CTCs. Further, these GFP-positive cells (CTCs) may be concentrated for phenotyping or genotyping.

In the present invention, examples of a subject include mammals such as humans, rabbits, guinea pigs, rats, mice, hamsters, cats, dogs, goats, pigs, sheep, cows, horses, monkeys and so on.

The amount of the reagent of the present invention to be used is selected as appropriate, depending on the state and amount of a biological sample to be used for detection and the type of detection method to be used, etc. For example, in the case of a blood sample, the reagent of the present invention can be used in an amount ranging from about 0.01 to 1000 MOI, preferably 0.1 to 100 MOI, and more preferably 1 to 10 MOI per 1 to 50 ml, preferably 3 to 25 ml, and more preferably 5 to 15 ml of the blood sample. MOI refers to the ratio between the amount of virus (infectious unit) and the number of cells when a given amount of cultured cells are infected with a given amount of virus particles, and is used as an index when viruses are infected into cells.

To infect the recombinant virus into cells, the following procedures may be used for this purpose. First, cells are seeded in a culture plate containing an appropriate culture medium and cultured at 37° C. in the presence of carbon dioxide gas. The culture medium is selected from DMEM, MEM, RPMI-1640 and others commonly used for animal cell culture, and may be supplemented with serum, antibiotics, vitamins and so on, if necessary. The cultured cells are inoculated with a given amount of the virus, for example, at 0.1 to 10 MOI.

For confirmation of virus growth, the virus-infected cells are collected and treated to extract their DNA, followed by real-time PCR with primers targeting an appropriate gene possessed by the virus of the present invention, whereby virus growth can be quantitatively analyzed.

In cases where GFP gene is used as a reporter gene, labeled cells may be detected as follows: cells showing virus growth will emit a given fluorescence (e.g., a green fluorescence for GFP) upon irradiation with an excitation light, so that cancer cells can be visualized by the fluorescence. For example, when the virus-infected cells are observed under a fluorescence microscope, GFP fluorescence production can be seen in the cells. Moreover, to observe the virus-infected cells over time, GFP fluorescence production can be monitored over time with a CCD camera.

Moreover, the reagent of the present invention also allows real-time detection of cancer cells present in vivo. To label and detect cells in vivo in a real-time manner, the recombinant adenovirus of the present invention may be administered in vivo.

The reagent of the present invention may be applied directly to the affected area or may be introduced in vivo (into target cells or organs) in any known manner, e.g., by injection into vein, muscle, peritoneal cavity or subcutaneous tissue, inhalation from nasal cavity, oral cavity or lungs, oral administration, catheter-mediated intravascular administration and so on, as preferably exemplified by local injection into muscle, peritoneal cavity or elsewhere, injection into vein, etc.

When the reagent of the present invention is administered to a subject, the dose may be selected as appropriate, depending on the type of active ingredient, the route of administration, a target to be administered, the age, body weight, sex and/or symptoms of a patient, and other conditions. As a daily dose, the amount of the virus of the present invention serving as an active ingredient may usually be set to around $10^6$ to $10^{11}$ PFU (plaque forming units), preferably around $10^9$ to $10^{11}$ PFU, given once a day or in divided doses.

Real-time in vivo monitoring of fluorescence from cancer cells has the advantage of being used for in vivo diagnostic agents. This is useful for so-called navigation surgery and so on. Details on navigation surgery can be found in WO2006/036004.

Further, the reagent of the present invention is useful for detection of CTCs as a biomarker, and hence the reagent of the present invention can be used to determine prognosis.

For example, in cases where GFP is used as a labeling protein in the virus of the present invention, a biological sample taken from a cancer patient before being treated by any cancer therapy (e.g., chemotherapy, radiation therapy, surgical operation) and a biological sample taken at a time point after a certain period (e.g., 1 to 90 days) has passed from the treatment are each infected with the virus of the present invention. Next, GFP-positive cells contained in the sample taken before the treatment and GFP-positive cells contained in the sample taken at a certain time point after the treatment are compared for their number under the same conditions. As a result, if the number of GFP-positive cells after the treatment becomes smaller than the number of GFP-positive cells before the treatment, a determination can be made that prognosis has been improved.

The present invention will be further described in more detail by way of the following illustrative examples, which are not intended to limit the scope of the invention.

Example 1

Preparation of Ad34 Fiber 142-3pT (1) Preparation of pHMCMV5-miR-142-3pT pHMCMV5 (Mizuguchi H. et al., Human Gene Therapy, 10: 2013-2017, 1999) was treated with NotI/KpnI and the resulting fragment was ligated to a double-stranded oligo, which had been prepared by annealing the following synthetic oligo DNAs, to thereby prepare pHMCMV5-miR-142-3pT(pre).

miR-142-3pT-S1:

(SEQ ID NO: 43)
5'-GGCCTCCATAAAGTAGGAAACACTACACAGCTCCATAAAGTAGGAA
ACACTACATTAATTAAGCGGTAC-3', each underline represents a miR-142-3p target sequence)

miR-142-3pT-AS1:

(SEQ ID NO: 44)
5'-CGCTTAATTAATGTAGTGTTTCCTACTTTATGGAGCTGTGTAGTGTT
TCCTACTTTATGGA-3', each underline represents a miR-142-3p target sequence)

Then, pHMCMV5-miR-142-3pT(pre) was treated with PacI/KpnI and the resulting fragment was ligated to a double-stranded oligo, which had been prepared by annealing the following synthetic oligo DNAs, to thereby obtain pHMCMV5-miR-142-3pT having 4 repeats of a miR-142-3p target sequence.

miR-142-3pT-S2:

(SEQ ID NO: 45)
5'-TCCATAAAGTAGGAAACACTACAGGACTCCATAAAGTAGGAAACA
CTACAGTAC-3', each underline represents a miR-142-3p target sequence)

(SEQ ID NO: 46)
5'-TGTAGTGTTTCCTACTTTATGGAGTCCTGTAGTGTTTCCTACTTTAT
GGAAT-3', miR-142-3pT-AS2:
each underline represents a miR-142-3p target sequence)

(2) Preparation of E1 Shuttle Plasmid pHM5-hAIB-miR-142-3pT pSh-hAIB (WO2006/036004) was digested with I-CeuI/PmeI and the digested product was electrophoresed on an agarose gel. A band of approximately 4.5 kbp (hAIB cassette) was excised from the gel and treated with GENECLEAN II (Q-Biogene) to purify and collect a DNA fragment. The purified DNA fragment (hAIB cassette) was ligated to a fragment which had been obtained from pHMCMV5-miR-142-3pT by being digested with NheI, treated with Klenow Fragment and further digested with I-CeuI, thereby obtaining pHM5-hAIB-miR-142-3pT having hTERT promoter, E1A gene. IRES (internal ribosomal entry site) sequence, E1B gene and a miR-142-3pT target sequence.

(3) Preparation of E3 Shuttle Plasmid pHM13CMV-EGFP-miR-142-3pT pEGFP-NI (Clontech) was digested with ApaI and NotI, and the resulting digested product was inserted into the ApaI/NotI site of pHMCMV5 to obtain pHMCMVGFP-1. pHMCMVGFP-1 was digested with PmeI/HindIII, and the digested product was electrophoresed on an agarose gel. A band of approximately 750 bp (EGFP) was excised from the gel and treated with GENECLEAN II to purify and collect a DNA fragment. The purified DNA fragment (EGFP) was ligated to a fragment which had been obtained from pBluescriptII KS+ by being digested with HindII/HindIII, thereby preparing pBSKS-EGFP. pBSKS-EGFP was digested with ApaI/XbaI, and the digested product was electrophoresed on an agarose gel. A band of approximately 750 bp (EGFP) was excised from the gel and treated with GENECLEAN II to purify and collect a DNA fragment. The purified DNA fragment (EGFP) was ligated to a fragment which had been obtained from pHMCMV5-miR-142-3pT by being digested with ApaI/XbaI, thereby obtaining pHMCMV5-EGFP-miR-142-3pT. pHMCMV5-EGFP-miR-142-3pT was digested with BglII, and the digested product was electrophoresed on an agarose gel. A band of approximately 2 kbp (CMV-EGFP-miR-142-3pT) was excised from the gel and treated with GENECLEAN II to purify and collect a DNA fragment. The purified DNA fragment (CMV-EGFP-miR-142-3pT) was ligated to a fragment which had been obtained from pHM13 (Mizuguchi et al., Biotechniques, 30: 1112-1116, 2001) by being digested with BamHI and treated with CIP (Alkaline Phosphatase, Calf Intest), thereby obtaining pHM13CMV-EGFP-miR-142-3pT.

(4) Preparation of pAdHM49-hAIB142-3pT-CG142-3pT
pAdHM49 (Mizuguchi et al, J. Controlled Release 110; 202-211, 2005) was treated with I-CeuI/PI-SceI and the resulting fragment was ligated to pHM5-hAIB-miR-142-3pT which had also been treated with I-CeuI/PI-SceI, thereby preparing pAdHM49-hAIB142-3pT in which hTERT promoter, E1A gene, IRES sequence, E1B gene and a miR-142-3pT target sequence were integrated into the E1-deficient region of the Ad vector. pAdHM49 is a recombinant adenovirus in which a region covering genes encoding the fiber knob and fiber shaft of the adenovirus type 5 fiber is replaced with a region covering genes encoding the fiber knob and fiber shaft of the adenovirus type 34 fiber, and hence pAdHM49 comprises the nucleotide sequence (SEQ ID NO: 49) of a gene encoding a region consisting of the fiber knob region and the fiber shaft region in the fiber protein of adenovirus type 34. The nucleotide sequence of a gene encoding the pAdHM49 fiber protein (i.e., the fiber knob region and fiber shaft region of the adenovirus type 34 fiber and the fiber tail region of the adenovirus type 5 fiber) is shown in SEQ ID NO: 50. In the nucleotide sequence shown in SEQ ID NO: 50, the nucleotide sequence of a gene encoding the fiber tail region of the adenovirus type 5 fiber is located at nucleotides 1 to 132, the nucleotide sequence of a gene encoding the fiber shaft region of the adenovirus type 34 fiber is located at nucleotides 133 to 402, and the nucleotide sequence of a gene encoding the fiber knob region of the adenovirus type 34 fiber is located at nucleotides 403 to 975. Namely, in the nucleotide sequence shown in SEQ ID NO: 50, the nucleotide sequence of a region derived from the adenovirus type 5 fiber is located at nucleotides 1 to 132, while the nucleotide sequence of a region derived from the adenovirus type 34 fiber is located at nucleotides 133 to 975.

Then, pAdHM49-hAIB142-3pT was digested with Csp45I and the resulting fragment was ligated to a fragment which had been obtained from pHM13CMV-EGFP-miR-142-3pT by being digested with ClaI, thereby obtaining pAdHM49-hAIB142-3pT-CG142-3pT in which hTERT promoter, E1A gene, IRES sequence, E1B gene and a miR-142-3pT target sequence were integrated into the E1-deficient region of the adenovirus vector and CMV promoter. EGFP and a miR-142-3pT target sequence were integrated into the E3-deficient region of the adenovirus vector, and which further comprised a gene encoding the fiber protein of adenovirus type 34.

(5) Preparation of Ad34 Fiber 142-3pT(E1,E3)
pAdHM49-hAIB142-3pT-CG142-3pT was linearized by being cleaved with a restriction enzyme PacI whose recognition site was present at each end of the adenovirus genome therein, and the linearized product was transfected into 293 cells seeded in a 60 mm culture dish by using Lipofectamine 2000 (Invitrogen). After about 2 weeks, a recombinant adenovirus Ad34 fiber 142-3pT(E1,E3) was obtained (FIG. 1).

The Ad34 fiber 142-3pT(E1, E3) corresponds to the Adenovirus type 5; TelomeScan F35 strain, which was deposited on Feb. 6, 2014, with the American Type Culture Collection (ATCC®) (10801 University Boulevard, Manassas, Va., 20110), and was provided with the deposit Accession No. PTA-120968. Please note that the depository ATCC® is an International Depository Authority (IDA) under the Budapest Treaty located in the USA.

Example 2

Activity Measurement of Ad34 Fiber 142-3pT(E1,E3)

(1) Cells

HeLa (derived from human uterine cancer cells) and LN319 (derived from human glioma cells) were used as CAR-positive cells, while LNZ308 (derived from human glioma cells), LN444 (derived from human glioma cells) and K562 (derived from human myelogenous leukemia cells) were used as CAR-negative cells. K562 cells are expressing miR-142-3p. DMEM (10% FCS, supplemented with antibiotics) was used for HeLa, LN319. LNZ308 and LN444 cells, while RPMI-1640 medium (10% FCS, supplemented with antibiotics) was used for K562 cells. These cells were cultured at 37° C. under saturated vapor pressure in the presence of 5% $CO_2$.

(2) Activity Measurement of Ad34 Fiber 142-3pT(E1,E3) by Flow Cytometry

Cells of each line were seeded in a 24-well plate at $5 \times 10^4$ cells/500 ul/well and treated with Ad34 fiber 142-3pT(E1, E3) at an MOI of 10. As a control, TelomeScan (i.e., a conditionally replicating adenovirus comprising hTERT promoter, E1A gene, IRES sequence and E1B gene integrated in this order into the E1-deficient site of adenovirus type 5 and comprising CMV promoter and GFP integrated in this order into the E3-deficient site of adenovirus type 5) was used. After culture for 24 hours, the cells were collected and the number of GFP-positive cells was measured using a flow cytometer MACSQuant (Miltenyi Biotec).

Figure 2:
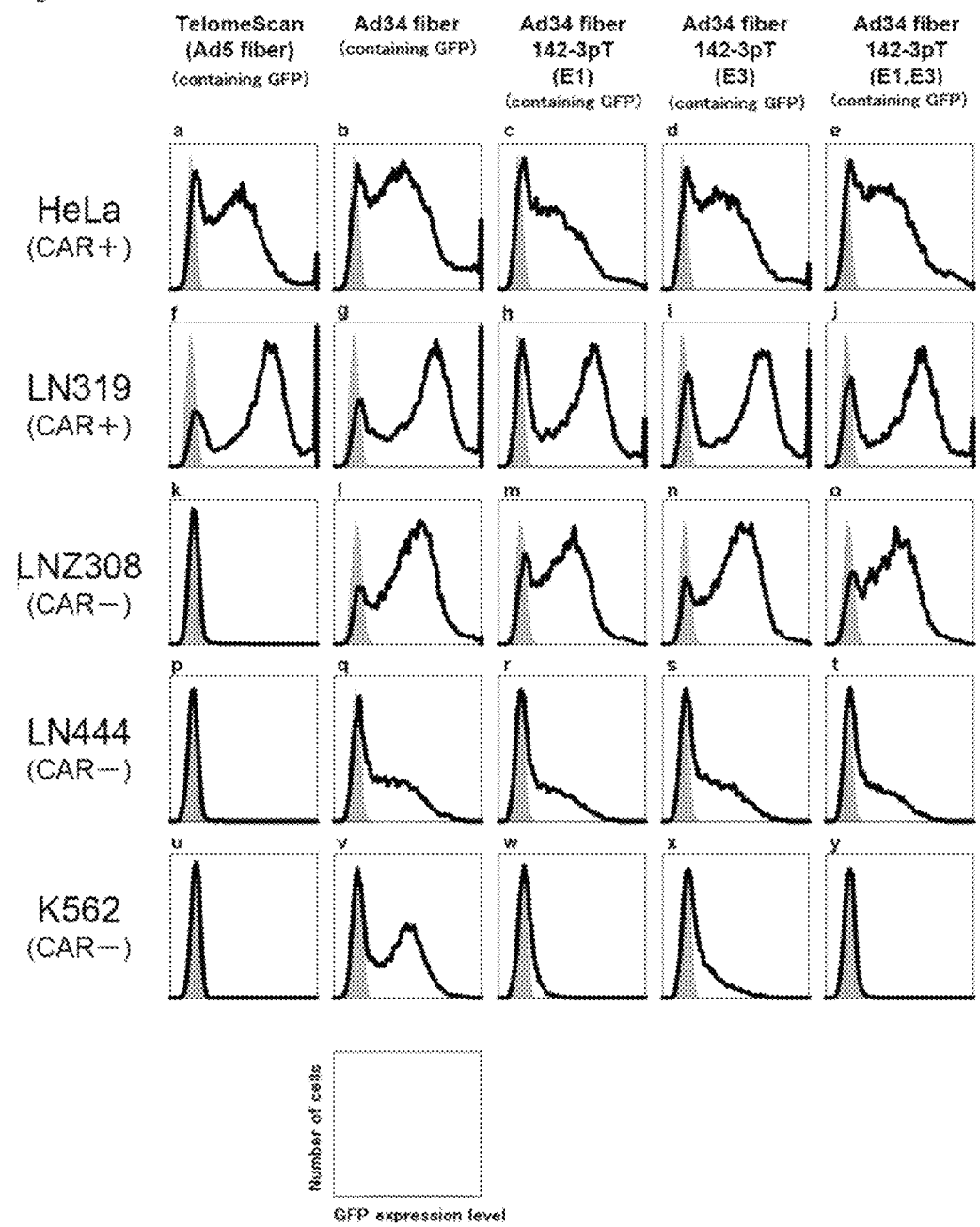
FIG. 2 shows the results measured for activity of recombinant adenoviruses by flow cytometry.

The results obtained are shown in FIG. 2. In the specification and FIG. 2, "TelomeScan (Ad5 fiber)" represents TelomeScan, while "Ad34 fiber" represents a recombinant adenovirus which comprises hTERT promoter, E1A gene, IRES sequence and E1B gene integrated in this order into the E1-deficient site of the adenovirus genome and also comprises CMV promoter and GFP integrated in this order into the E3-deficient site of the adenovirus genome and which comprises a gene encoding a fiber protein derived from adenovirus type 34. Likewise, "Ad34 fiber 142-3pT (E1)" represents a recombinant adenovirus which further comprises a target sequence of miR-142-3p integrated into the E1-deficient region (downstream of the E1B gene) in the above Ad34 fiber, while "Ad34 fiber 142-3pT(E3)" represents a recombinant adenovirus which further comprises a target sequence of miR-142-3p integrated into the E3-deficient region (downstream of the GFP gene) in the above Ad34 fiber. Likewise, "Ad34 fiber 142-3pT(E1,E3)" represents a recombinant adenovirus which further comprises a target sequence of miR-142-3p integrated into each of the E1- and E3-deficient regions (downstream of the E1B gene and downstream of the GFP gene, respectively) in the above Ad34 fiber. Moreover, in FIG. 2 and the subsequent figures. "(containing GFP)" is intended to mean that the GFP gene is inserted into each viral genome.

As a result of activity measurement, when LNZ308, LN444 and K562, which are CAR-negative cells, were infected with TelomeScan (Ad5 fiber), no GFP-positive cell was detected (FIG. 2, panels k, p and u). In contrast, when these cells were infected with Ad34 fiber, GFP-positive cells were detected (85.5% positive in LNZ308, 58.4% positive in LN444, and 63.7% positive in K562) (panels l, q and v).

This result indicated that the recombinant adenovirus of the present invention having a gene encoding the fiber protein of adenovirus type 34 allowed significant detection of CAR-negative cells.

Further, in the case of K562 cells which are CAR-negative and are expressing miR-142-3p, GFP-positive cells were 63.7% upon infection with Ad34 fiber (panel v), whereas GFP-positive cells were 12.2% upon infection with Ad34 fiber 142-3pT(E1) and 34.8% upon infection with Ad34 fiber 142-3pT(E3), and no GFP-positive cell was detected upon infection with Ad34 fiber 142-3pT(E1,E3) (panels w, x and y). Namely, the detection rate of K562 cells was significantly reduced when using an adenovirus comprising a target sequence of miR-142-3p integrated into either the E1- or E3-deficient region of the adenovirus genome, and K562 cells were no longer detected when using an adenovirus comprising a target sequence of miR-142-3p integrated into each of the E1- and E3-deficient regions.

This result indicated that the recombinant virus of the present invention comprising a target sequence of miR-142-3p did not detect highly miR-142-3p-expressing cells, such as normal blood cells.

Moreover, the above result was further investigated. When the case of infecting K562 cells with Ad34 fiber (panel v) was compared with the case of infecting the same cells with Ad34 fiber 142-3pT(E1) (panel w), the rate (%) of GFP-positive cells in the case of the infection with Ad34 fiber 142-3pT(E1) was decreased by 19% (12.2%/63.7%). This result shows an effect based on miR-142-3pT (target sequence of miR-142-3p) integrated into the E1-deficient region. On the other hand, when the case of infecting K562 cells with Ad34 fiber (panel v) was compared with the case of infecting the same cells with Ad34 fiber 142-3pT(E3) (panel x), the rate (%) of GFP-positive cells in the case of the infection with Ad34 fiber 142-3pT (E3) was decreased by 54% (34.8%/63.7%). This result shows an effect based on miR-142-3pT integrated into the E3-deficient region. These results indicate that, in the case of using an adenovirus wherein miR-142-3pT has been integrated into both E1- and E3-deficient regions in this experiment, if the result obtained shows an additive effect based on two sequences of miR-142-3pT integrated into both E1- and E3-deficient regions, the rate (%) of GFP-positive cells would be expected to be about 10% (19%×54%).

However, contrary to the above expectation, in this Example, in the case (panel y) of infecting K562 cells with Ad34 fiber 142-3pT (E1, E3) wherein miR-142-3pT had been integrated into both E1- and E3-deficient regions, almost no GFP-positive cells were detected.

This fact indicates that, in the effects exerted by the present invention, the effect based on two sequences of miR-142-3pT integrated was not an additive effect but a synergistic effect.

As described herein above, CTC detection techniques are required to detect several to several tens of cells among a billion of blood cells, and therefore desired to have a high accuracy in the detection of CTC. In addition, in order to increase the CTC detection accuracy, the CTC detection techniques are desired to bring the number of cells detected as false positive boundlessly close to zero. In general, 1 μL of blood is known to contain thousands of white blood cells, and these white blood cells are desired not to be detected as false positive.

In the CTC detection techniques, even the presence of several false positive cells has a great influence on the determination of whether a subject has CTC.

As described above, in this Example, contrary to the expectation, in the case of infecting K562 cells with Ad34 fiber 142-3pT (E1, E3) wherein miR-142-3pT had been integrated into both E1- and E3-deficient regions, almost no GFP-positive cells were detected. This result shows unexpectedly remarkable effect according to the present invention.

Example 3

Detection of Cancer Cells in Blood Samples Using Ad34 Fiber 142-3pT(E1,E3)

$5 \times 10^4$ H1299 cells (CAR-positive) were suspended in 5 mL blood and erythrocytes were lysed to collect PBMCs. To these PBMCs, a virus was added in an amount of $1\times10^9$, $1\times10^{10}$ or $1\times10^{11}$ VPs (virus particles) and infected at 37° C. for 24 hours while rotating with a rotator. The cells were collected and immunostained with anti-CD45 antibody, and GFP-positive cells were observed under a fluorescence microscope. CD45 is known to be a surface antigen of blood cell lineage cells except for erythrocytes and platelets. "GFP Positive Cancer cells (%)" found in the vertical axis of FIGS. 3 and 4 represents the "number of GFP-positive and CD45-negative cells (%) among GFP-positive cells."

As a result, many false positive cells (GFP-positive and CD45-positive cells) were observed upon infection with TelomeScan (Ad5 fiber), whereas false positive cells were very few upon infection with Ad34 fiber 142-3pT(E1,E3), so that cancer cells were able to be specifically detected.

Figure 3:
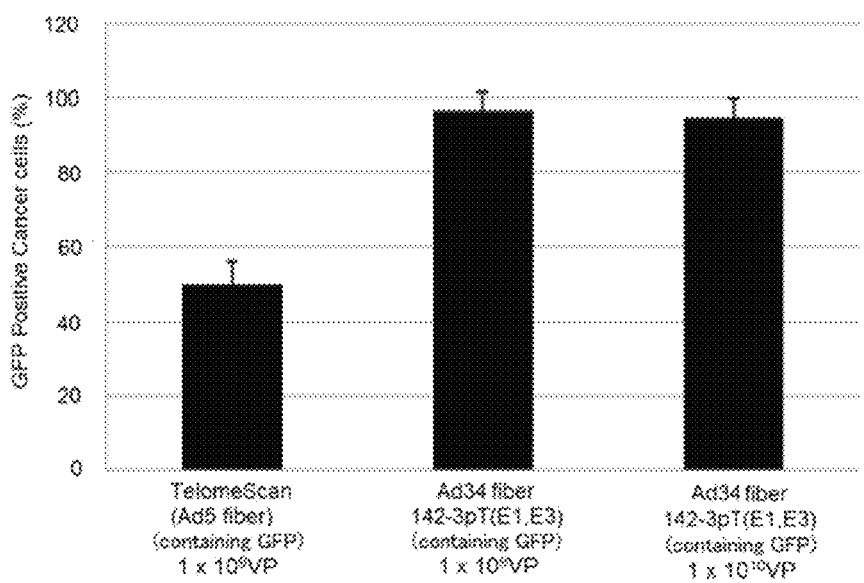
FIG. 3 shows the results detected for H1299 cells contained in blood samples.
Figure 4:
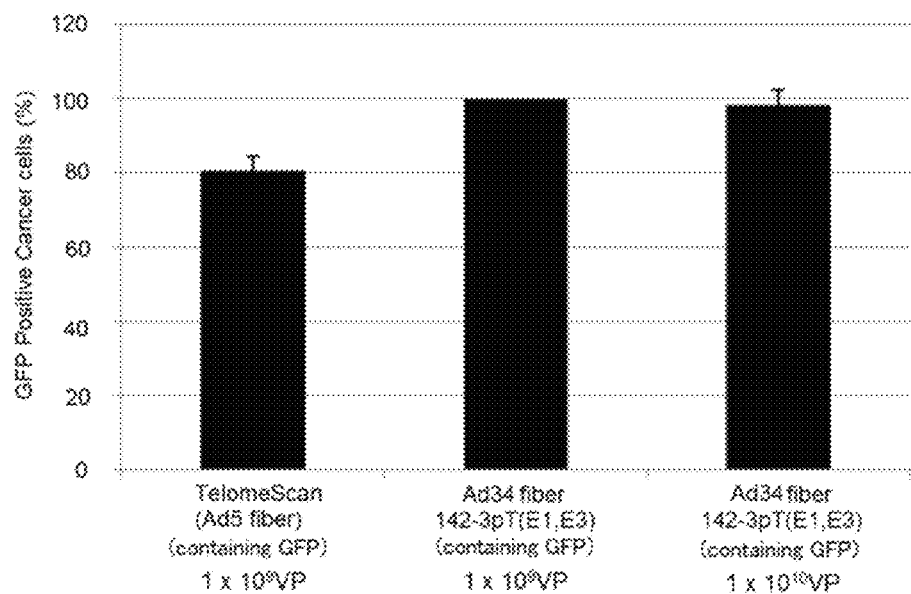
FIG. 4 shows the results detected for A549 cells contained in blood samples.

Moreover, as a result of quantitative analysis on the detection specificity of H1299 cells, many false positive cells were detected in the case of TelomeScan (Ad5 fiber) upon virus infection at $1\times10^9$ VPs, whereas the detection specificity was 90% or higher and some samples showed 100% detection specificity in the case of Ad34 fiber 142-3pT(E1,E3) even when the amount of virus infection was increased (FIG. 3). Likewise, quantitative analysis was also performed on A549 cells (CAR-positive cells) in the same manner, indicating that the detection specificity was 100% upon virus infection at $1\times10^9$ VPs (FIG. 4). These results indicated that the recombinant virus of the present invention allowed specific detection of cancer cells contained in the PBMC fraction.

In view of the foregoing, the detection reagent and diagnostic reagent of the present invention were demonstrated to allow detection of highly malignant CAR-negative cancer cells and, on the other hand, to ensure no false positive detection of highly miR-142-3p-expressing normal blood cells (e.g., leukocytes), etc.; and hence they were shown to be very effective for detection of circulating tumor cells (CTCs) in blood.

Example 4

Activity Measurement of Ad34 Fiber 142-3pT(E1,E3) in Various Human Cancer Cell Lines (1) Cells The cancer cells used in this example were human non-small cell lung cancer-derived H1299 cells, human lung cancer-derived A549 cells, human breast cancer-derived MCF7 cells, human breast cancer-derived MDA-MB-231 cells, human bladder cancer-derived KK47 cells, human gastric cancer-derived MKN45 cells, human colorectal cancer-derived SW620, human liver cancer-derived Huh7 cells, human pancreatic cancer-derived Panel cells, human glioma-derived LN319 cells, human bladder cancer-derived T24 cells, human glioma-derived LNZ308 cells, and human glioma-derived LN444 cells.

(2) Activity Measurement of Ad34 Fiber 142-3pT(E1,E3) by Flow Cytometry $5\times10^4$ cancer cells of each line were suspended in 500 μl medium, to which 100 μl of a conditionally replicating Ad suspension prepared at $5\times10^5$ or $5\times10^6$ pfu/ml was then added. The resulting mixture of the cells and the conditionally replicating Ad was seeded in a 24-well plate and cultured at 37° C. for 24 hours. The cells were collected and centrifuged at 1500 rpm for 5 minutes. After removal of the medium, the cells were suspended in 300 μl of 2% FCS-containing PBS and measured for GFP-positive rate using a flow cytometer (MACS Quant Analyzer. Miltenyi Biotec). The data obtained were analyzed by FCS multi-color data analysis software (Flowjo).

Figure 5:
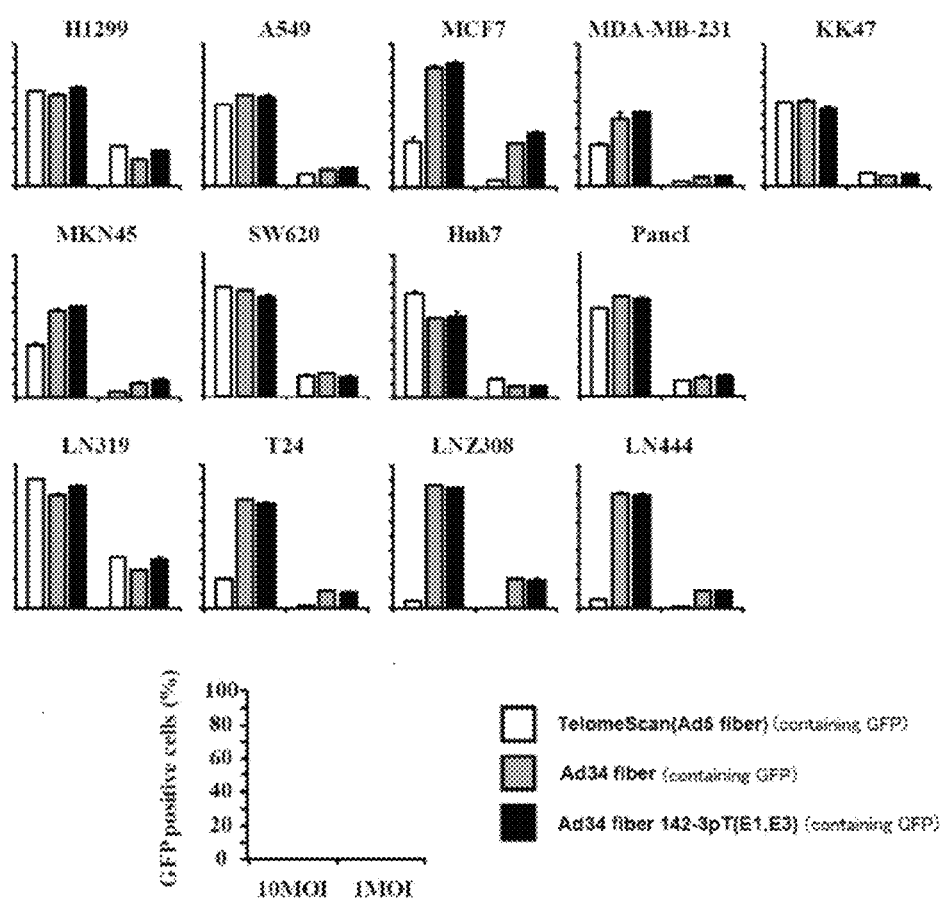
FIG. 5 shows the results measured for activity of the recombinant adenovirus of the present invention in various types of cancer cells.

As a result, Ad34 fiber 142-3pT(E1,E3) was found to efficiently infect almost all cancer cells, and 60% or more of the cancer cells were GFP-positive. Particularly in the case of CAR-negative cells (T24, LNZ308, LN444), their GFP-positive rate was significantly improved when compared to conventionally used TelomeScan (FIG. 5).

This result indicated that the recombinant virus of the present invention allowed efficient detection of not only CAR-positive cells but also CAR-negative cells.

Example 5

Detection of Cancer Cells Having Undergone Epithelial-Mesenchymal Transition (EMT)

Human pancreatic cancer PancI cells were cultured for 6 days in the presence of 10 ng/mL recombinant TGF-β1 to thereby induce epithelial-mesenchymal transition (EMT). After induction of EMT, relative expression of mRNAs encoding E-cadherin, EpCAM, hTERT, N-cadherin, Slug and Snail was measured by real-time RT-PCR. In addition, CAR and CD46 expression in the Panc I cells was analyzed by flow cytometry. The virus of the present invention was infected into the cells in the same manner as shown in Example 4.

Figure 6:
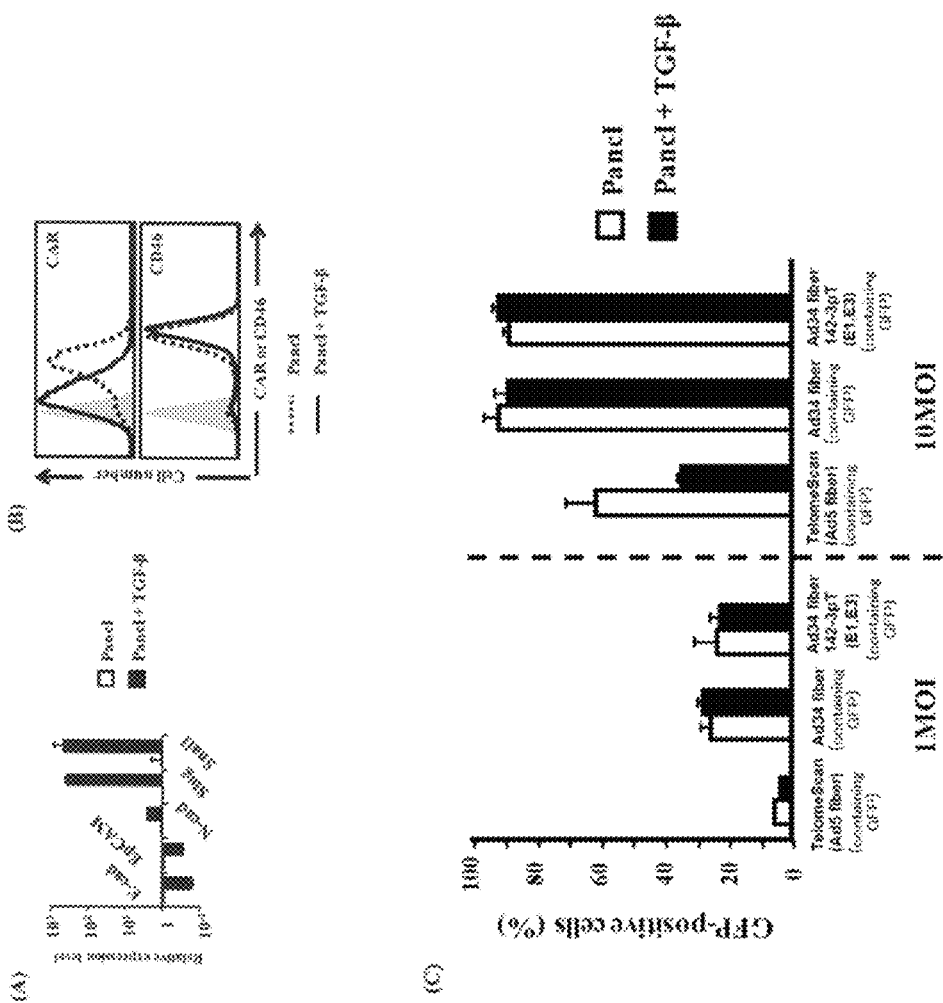
FIG. 6 shows the results detected for cancer cells having undergone epithelial-mesenchymal transition (EMT).

As a result, upon culture in a TGF-3-containing medium, the expression of EMT marker genes Slug, Snail and N-cadherin were increased, while the expression of epithelial markers E-cadherin and EpCAM was reduced, thus indicating that EMT has been induced (FIG. 6A). Moreover, upon EMT induction, CAR expression was reduced whereas CD46 expression was not reduced at all (FIG. 6B). Further, when conventionally used TelomeScan was used for PancI cells having undergone EMT only about 35% of these cells were GFP-positive, whereas almost 90% or more of the cells were GFP-positive in the case of Ad34 fiber 142-3pT(E1, E3) (FIG. 6C).

These results indicated that the recombinant virus of the present invention allowed highly sensitive detection of cancer cells having undergone epithelial-mesenchymal transition (EMT).

Example 6

Detection of Cancer Stem Cells

MCF7 cells and MCF7-ADR cells (cancer cells resistant to the anticancer agent adriamycin) were each seeded in a 96-well plate at $1\times10^3$ cells/well, and on the following day, adriamycin was added thereto at 0.2, 1, 5, 25 or 125 μg/mL. After 24 hours from the addition of adriamycin, an alamar-Blue® cell viability reagent was used to measure cell viability (value: mean±S.D. (n=6)).

MCF7 cells and MCF7-ADR cells were also analyzed by flow cytometry for expression of CAR, CD46, P-glycoprotein (MDR), CD24 and CD44. $5\times10^5$ MCF7-ADR cells were suspended in 100 μl of 2% FCS-containing PBS, and FITC-labeled mouse anti-human CD24 antibody and PE-labeled mouse anti-human CD44 antibody were each added thereto in a volume of 1 μl, followed by reaction for 1 hour on ice under light-shielded conditions. After washing with 4 ml of 2% FCS-containing PBS, the suspension was centrifuged at 1500 rpm for 5 minutes to remove the supernatant by aspiration. The cells were suspended again in 100 μl of 2%

FCS-containing PBS and subjected to a cell sorter (FACS Aria II cell sorter; BD Biosciences) to sort a CD24-negative and CD44-positive cell fraction. The data obtained were analyzed by FCS multi-color data analysis software (Flowjo). In human breast cancer cells, a fraction having the characteristics of CD24-negative and CD44-positive cells is known to be cancer stem cells (Al-Hajj M., et al., Proc Natl Acad Sci USA, 100; 3983-3988, (2003)). The virus of the present invention was infected into the cells in the same manner as shown in Example 4.

Figure 7:
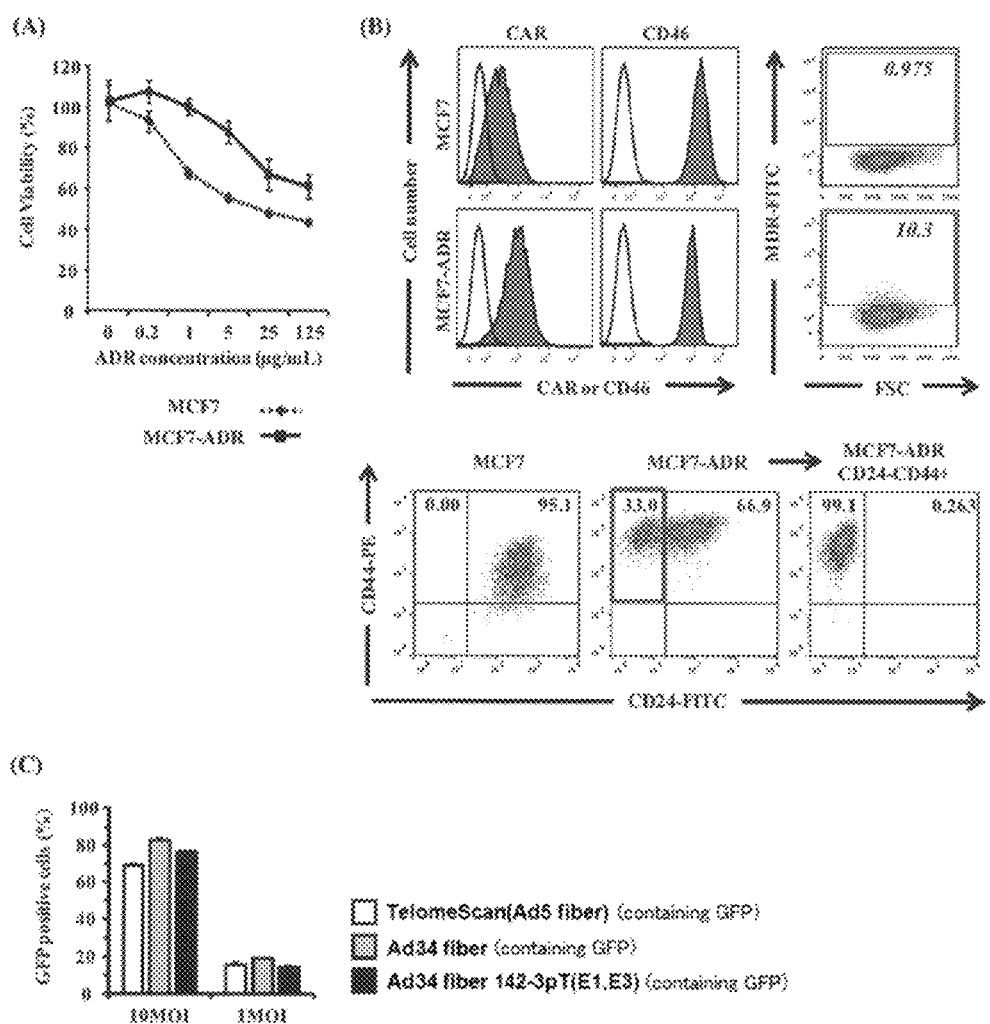
FIG. 7 shows the results detected for cancer stem cells.

As a result, MCF7-ADR cells showed significantly high viability even in the presence of adriamycin when compared to MCF7 cells and hence were found to have drug resistance ability (FIG. 7A). MCF7-ADR cells were also found to highly express CAR and CD46 as in the case of MCF7 cells. Moreover, MCF7-ADR cells were also found to highly express MDR, which is a membrane protein responsible for drug elimination ability (FIG. 7B). Further, when Ad34 fiber 142-3pT(E1,E3) was infected into CD24-negative and CD44-positive cells among MCF-ADR cells, 80% or more of the cells were GFP-positive. In contrast, about 70% of the cells were GFP-positive in the case of conventionally used TelomeScan (FIG. 7C).

These results indicated that the recombinant virus of the present invention allowed detection of drug-resistant cancer cells. Moreover, it was also indicated that the recombinant virus of the present invention allowed detection of cancer stem cells.

Example 7

Detection of Cancer Cells in Blood Samples Using Ad34 Fiber 142-3pT(E1,E3)

H1299 cells or T24 cells were infected with a lentivirus vector expressing a red fluorescent protein (monomeric red fluorescent protein; RFP) at an MOI of 100 and cultured. To obtain cell clones, the cells were then seeded in a 96-well plate at 0.1 cells/well and cultured until colonies were formed. RFP-expressing cells were selected under a fluorescence microscope and subjected to extended culture, followed by flow cytometry to measure the intensity of RFP expression. Then, cells showing high intensity of RFP expression were identified as RFP-expressing cells.

Human peripheral blood mononuclear cells (hPBMCs) obtained from 1.0 mL of human peripheral blood were suspended in 800 µL of RPMI-1640 medium (10% FCS, supplemented with antibiotics). To the hPBMC suspension, cancer cells prepared at $1.0 \times 10^5$ or $5.0 \times 10^{-5}$ cells/mL were added in a volume of 100 µL (in FIG. 8, "spiked cancer cells" represents the number of cancer cells added to the hPBMC suspension). Further, a conditionally replicating Ad suspension prepared at $2 \times 10^8$ pfu/mL was added in a volume of 100 µL to give a total volume of 1 mL, followed by culture at 37° C. for 24 hours while slowly rotating with a rotator.

The cell suspension cultured for 24 hours after virus infection was centrifuged at 300×g for 5 minutes to remove the supernatant. A cell fixative was added in a volume of 200 µL and reacted at 4° C. under light-shielded conditions for 15 minutes. After addition of 1 mL PBS, the suspension was centrifuged at 300×g for 5 minutes to remove the supernatant. The cells were suspended in 2% FCS-containing PBS and measured for GFP-positive rate using a flow cytometer (MACS Quant Analyzer: Miltenyi Biotec). The data obtained were analyzed by FCS multi-color data analysis software (Flowjo).

Figure 8:
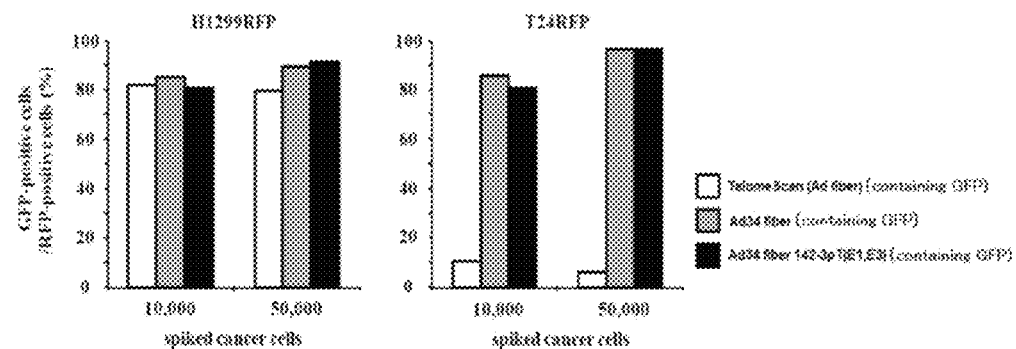
FIG. 8 shows the results detected for H1299 and T24 cells contained in blood samples by using a red fluorescent protein.

In this study, cancer cells labeled with RFP (red fluorescent protein) were mixed into hPBMCs to examine whether the cancer cells in hPBMCs were able to be detected. As a result, in the case of CAR-positive cancer cells (H1299), TelomeScan (Ad5 fiber) and Ad34 fiber 142-3pT(E1,E3) were both able to detect 80% or more of the cancer cells. On the other hand, in the case of CAR-negative cancer cells (T24), TelomeScan (Ad5 fiber) achieved very low detection efficiency (about 10% of the cells were detected as being GFP-positive), whereas Ad34 fiber 142-3pT(E1,E3) was able to detect 80% or more of the cancer cells (FIG. 8).

This result indicated that the recombinant adenovirus of the present invention allowed efficient detection of not only CAR-positive cancer cells but also CAR-negative cancer cells.

Example 8

Full Sequencing of Ad34 Fiber 142-3pT (E1,E3) Genome

In the present example, a full sequencing of Ad34 Fiber 142-3pT (E1,E3) genome was acquired by constructing a shotgun library using the Nextera XT DNA Library Preparation Kit and the Nextera XT Index kit (illumina, Inc.), followed by sequencing the clones using MiSeq System (illumina, Inc.) to provide 2,412,121 base pairs sequencing data.

Method
(1) Test Samples

In this Example, adenoviral genome DNA was prepared from the test article using a Qiagen viral DNA extraction method and final concentration was 8.1 ng/µL and the total amount was 10 µL.

(2) Shotgun Library Construction and DNA Sequencing
(2-1) Tagment Genomic DNA and Amplify Libraries One ng of purified Ad34 Fiber 142-3pT (E1,E3) was used for generating the library by applying the Nextera XT DNA Library Preparation Kit according to the manufacturer's instructions with the exception of using the primers of the Nextera XT Index kit. In brief, DNA sample was fragmented and tagged with adapter sequences by Nextera XT transposase and tagged with Index sequence.

(2-2) Clean Up Libraries

The resulting fragments were purified by using Agencourt AMPure XP beads (Beckman Coulter), separated by agarose gel electrophoresis and extracted from the gel in the range of 350-600 bases. The fragments were size-selected by a High Sensitivity DNA Chip on the Bioanalyzer 2100 (Agilent Technologies, Inc.) and quantified by Qubit 3.0 Fluorometer (Thermo Fisher Scientific, Inc.) before loading on the sequencing chip. The final concentration of the resulted library was 1.3 ng/µL and total amount was 10 µL.

(2-3) Sequencing and Assembly

The resulted clean up library was denatured by 0.2N NaOH for 5 min. After denaturation, it was diluted into 12 pM by hybridization buffer before loading on the MiSeq chip. After 300-bp paired-end read sequencing on the MiSeq platform (Illumina), the data were base called and reads with the same barcode were collected and assigned to a sample on the sequencing instrument. The uncallable ends of the MiSeq reads (B in input file) were automatically trimmed by the Sickle: sliding-window, adaptive, quality-based trimming tool for FastQ files (Version 1.33) software (Joshi N A, Fass J N (2011)) and Fastx tool kit (Ver 0.0.13). De novo assembly was performed as follows: the failed reads (Y in header information for the quality score) were removed by using Bayes hammer implemented, the resulted sequences were assembled at parameter k=21, 33, 55, 77, 99, 127 and repaired mismatches by SPAdes Genome Assembler (Ver 3.6.0) (J. Comp. Biol. 19(5) (2012): 455-77.). The assemble data was aligned to reference sequence by Bowtie2 (Ver 2.2.4).

Result

The assembly resulted in a contig length of 35,324 bp (SEQ ID NO: 51), in the range of 20,000-2000,000 reads. The sequences of genes or regulatory elements were aligned for the resulting full sequence of Ad34 Fiber 142-3pT (E1,E3).

The location thereof at SEQ ID NO: 51 as follows:

The human telomerase reverse transcriptase promoter starts at position 554 and ends at position 1008, therefore consisting of 455 nucleotides.

The E1A gene starts at position 1041 and ends at position 1939, therefore consisting of 899 nucleotides.

The E1B gene starts at position 2616 and ends at position 4438, therefore consisting of 1823 nucleotides.

The IRES sequence starts at position 1961 and ends at position 2581, therefore consisting of 621 nucleotides.

The first microRNA sequence (SEQ ID NO: 52) starts at position 4508 and ends at position 4612, therefore consisting of 105 nucleotides.

The second microRNA sequence (SEQ ID NO: 52) starts at position 30715 and ends at position 30819, therefore consisting of 105 nucleotides.

The cytomegalovirus (CMV) promoter starts at position 29,381 and ends at position 29,966, therefore consisting of 586 nucleotides.

The GFP gene starts at position 29,988 and ends at position 30,704, therefore consisting of 717 nucleotides.

The replication cassette (SEQ ID NO: 53) starts at position 554 and ends at position 4612, therefore consisting of 4059 nucleotides.

The labeling cassette (SEQ ID NO: 54) starts at position 29381 and ends at position 30819, therefore consisting of 1439 nucleotides.

The gene encoding a CD46-binding fiber protein (SEQ ID NO: 50) starts at position 31192 and ends at position 32166, therefore consisting of 975 nucleotides.

The sequence comprising four units of a target sequence of miR-142-3p was determined as follow:

(SEQ ID NO: 52)
5'-tccataaagtaggaaacactacacagctccataaagtaggaaacact
acattaattccataaagtaggaaacactacaggactccataaagtaggaa
acactaca-3', each underline represents a single unit of a target sequence of miR-142-3p).

Example 9

Detection of Cancer Cells in Blood Samples Using Ad34 Fiber 142-3pT(E1,E3)

(1) Cells

H661 (derived from human lung cancer cells) was used as a CAR-positive cell without expression of miR-142-3p.

(2) Detection of Cancer Cells Infected with the Ad34 Fiber 142-3pT(E1,E3) Sequenced at Example 8 by Fluorescence Microscope Observation One hundred of H661 cells were suspended in 7.5 mL blood and erythrocytes were lysed to collect PBMCs. To these PBMCs, a virus was added in an amount of $1\times10^9$ VPs (virus particles) for Ad34 fiber 142-3pT(E1,E3) or $3\times10^6$ for TelomeScan (Ad5 fiber) and infected at 37° C. for 24 hours while rotating with a rotator. The cells were collected and immunostained with anti-CD45 antibody, and GFP-positive cells were observed under a fluorescence microscope. CD45 is known to be a surface antigen of blood cell lineage cells except for erythrocytes and platelets. "GFP Positive Cancer cells (%)" found in the vertical axis of FIG. 9 represents the "number of GFP-positive and CD45-negative cells (%) among GFP-positive cells."

As a result, many false positive cells (GFP-positive and CD45-positive cells) were observed upon infection with TelomeScan (Ad5 fiber), whereas false positive cells were not observed upon infection with Ad34 fiber 142-3pT(E1, E3), so that cancer cells were able to be specifically detected.

Figure 9:
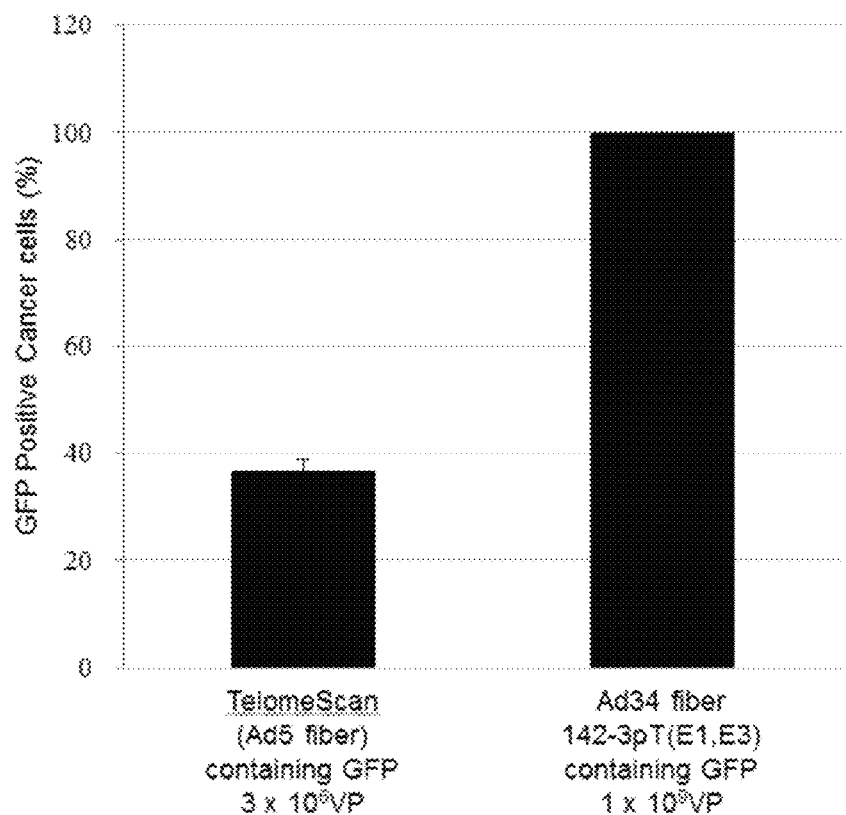
FIG. 9 shows the results detected for H661 cells contained in blood samples.

Moreover, as a result of quantitative analysis on the detection specificity of H661 cells, many false positive cells were detected in the case of TelomeScan (Ad5 fiber) upon virus infection at $3\times10^6$ VPs, whereas the detection specificity was showed 100% detection specificity in the case of Ad34 fiber 142-3pT(E1,E3) even when the amount of virus infection was increased ($1\times10^9$ VPs) (FIG. 9). These results indicated that the recombinant virus of the present invention allowed specific detection of cancer cells contained in the PBMC fraction.

Example 10

Activity Measurement of Ad34 Fiber 142-3pT(E1,E3)

(1) Cells

HeLa (derived from human uterine cancer cells) was used as a CAR-positive cell without expression of miR-142-3p, while K562 (derived from human myelogenous leukemia cells) was used as a CAR-negative cell expressing miR-142-3p. CD293 medium without phenol containing DMEM (10% FCS, supplemented with antibiotics) was used for HeLa cell, while RPMI-1640 medium (10% FCS, supplemented with antibiotics) was used for K562 cell. These cells were cultured at 37° C. under saturated vapor pressure in the presence of 5% $CO_2$.

(2) Activity Measurement of Ad34 Fiber 142-3pT(E1,E3) Sequenced at Example 8 by Multi-Plate Reader Cells of each line were seeded in a 12-well plate at $8\times10^5$ cells/well and treated with Ad34 fiber 142-3pT(E1,E3) at an MOI of 400. As a control, Ad34 fiber was used at an MOI of 150, which can produce the same intensity of GFP fluorescence using Ad34 fiber 142-3pT(E1,E3) at an MOI of 400 in HeLa cells. After culture for 24 hours, the cells were collected and lysed by GLO lysis buffer (Promega Corporation).

The fluorescence intensity of the lysate was measured using a multi-plate reader, PowerScan HT (DS Pharma Biomedical Co., Ltd.).

Figure 10:
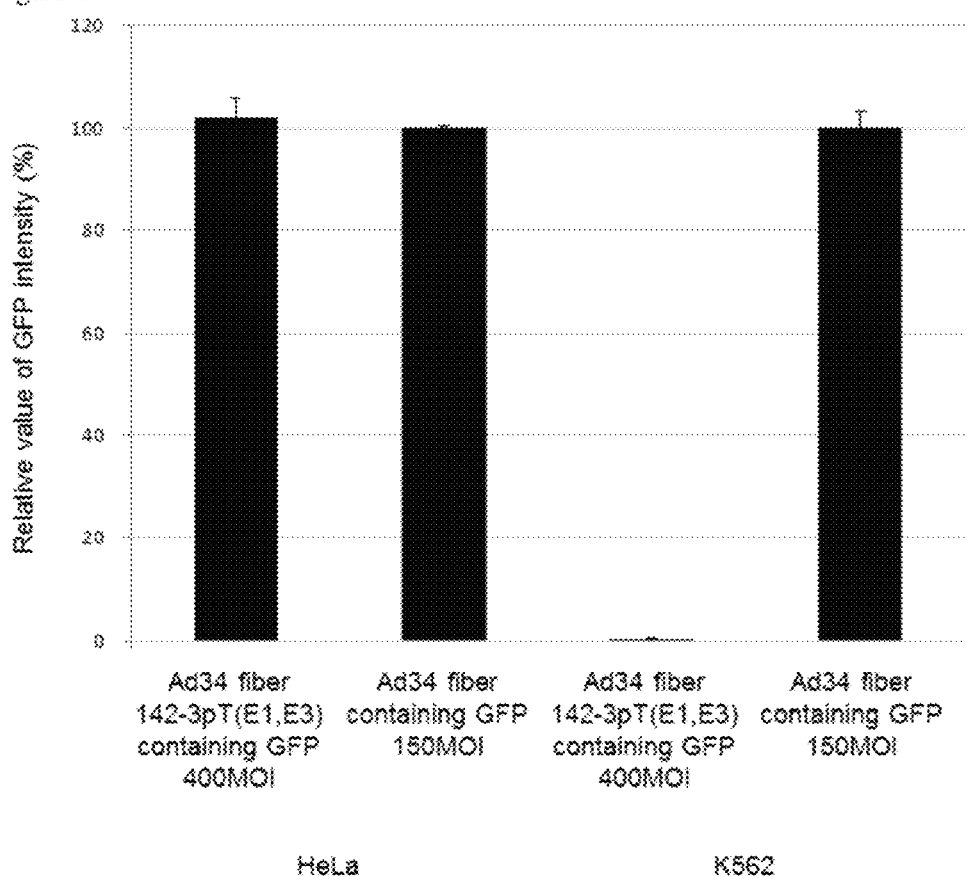
FIG. 10 shows the results measured for activity of the recombinant adenovirus of the present invention in HeLa and K562 cells.

The results obtained are shown in FIG. 10. In FIG. 10, the fluorescence intensity of each cell infected with Ad34 fiber 142-3pT(E1,E3) was shown as a relative value against those of the cell infected with Ad34 fiber, assuming the latter was 100%.

As a result of activity measurement, when K1562 (miR-142-3p-negative cells) were infected with Ad34 fiber 142-3pT(E1,E3), the detected intensity of GFP fluorescence was very little (0.45%) as compared to those of Ad34 fiber (FIG. 10).

This result indicated that the recombinant virus of the present invention comprising a target sequence of miR-142-3p did not detect highly miR-142-3p-expressing cells, such as normal blood cells.

INDUSTRIAL APPLICABILITY

Reagents comprising the recombinant adenovirus of the present invention enable simple and highly sensitive detection of CAR-negative cancer cells without detection of normal blood cells (e.g., leukocytes).

SEQUENCE LISTING FREE TEXT

SEQ ID NO: 4: synthetic DNA
SEQ ID NOs: 5 to 26: synthetic RNA
SEQ ID NOs: 27 to 28: synthetic DNA
SEQ ID NOs: 43 to 46: synthetic DNA
SEQ ID NOs: 50 to 55: synthetic DNA

The invention claimed is:

1. A recombinant adenovirus, which comprises:
a replication cassette comprising a polynucleotide comprising a human telomerase reverse transcriptase promoter, E1A gene, IRES sequence and E1B gene in this order, and a target sequence of a first microRNA, wherein the first microRNA is miR-142 and the target sequence comprises a nucleotide sequence having at least 98% identity to the nucleotide sequence consisting of SEQ ID NO: 52, and wherein the replication cassette is integrated into the E1 region of the adenovirus genome;
a labeling cassette comprising a reporter gene, a promoter capable of regulating the expression of the reporter gene, and a target sequence of a second microRNA, wherein the second microRNA is miR-142 and the target sequence comprises a nucleotide sequence having at least 98% identity to the nucleotide sequence consisting of SEQ ID NO: 52, and wherein the labeling cassette is integrated into the E3 region of the adenovirus genome; and
a gene encoding a CD46-binding fiber protein comprising at least the fiber knob region in the fiber protein of adenovirus type 34 or 35, which comprises a nucleotide sequence having at least 99% identity to the nucleotide sequence consisting of SEQ ID NO: 50 and is integrated into the adenovirus genome.

2. The recombinant adenovirus according to claim 1, wherein the reporter gene is a gene encoding a protein which emits fluorescence or a gene encoding an enzyme protein which generates a luminophore or a chromophore upon enzymatic reaction.

3. The recombinant adenovirus according to claim 1, wherein the promoter capable of regulating the expression of the reporter gene is a human telomerase reverse transcriptase promoter or cytomegalovirus promoter.

4. The recombinant adenovirus according to claim 1, wherein the replication cassette comprises a nucleotide sequence having at least 99%0 identity to the nucleotide sequence consisting of SEQ ID NO: 53.

5. The recombinant adenovirus according to claim 1, wherein the labeling cassette comprises a nucleotide sequence having at least 99% identity to the nucleotide sequence consisting of SEQ ID NO: 54.

6. A recombinant adenovirus, which comprises:
a replication cassette comprising a nucleotide sequence having at least 99% identity to the nucleotide sequence consisting of SEQ ID NO: 53 that is integrated into the E1 region of the adenovirus genome;

a labeling cassette comprising a nucleotide sequence having at least 99% identity to the nucleotide sequence consisting of SEQ ID NO: 54 and is integrated into the E3 region of the adenovirus genome; and a gene encoding a CD46-binding fiber protein comprising a nucleotide sequence having at least 99% identity to the nucleotide sequence consisting of SEQ ID NO: 50 and is integrated into the adenovirus genome.

7. A recombinant adenovirus, which comprises a nucleotide sequence having at least 99% identity to the nucleotide sequence consisting of SEQ ID NO: 51.

* * * * *